(12) United States Patent
Blanchetot et al.

(10) Patent No.: US 11,447,544 B2
(45) Date of Patent: Sep. 20, 2022

(54) ANTI-IL-22R ANTIBODIES

(71) Applicant: argenx BV, Zwijnaarde (BE)

(72) Inventors: Christophe Frederic Jerome Blanchetot, Ghent (BE); Birgitte Ursø, Ballerup (DK); Tine Skak-Nielsen, Ballerup (DK); Malene Bertelsen, Ballerup (DK); Sebastian Van Der Woning, Ghent (BE); Michael Saunders, Ghent (BE); Johannes Joseph Wilhelmus De Haard, Ghent (BE)

(73) Assignee: argenx BV, Ghent (BE)

( * ) Notice: Subject to any disclaimer, the term of this patent is extended or adjusted under 35 U.S.C. 154(b) by 4 days.

(21) Appl. No.: 16/661,783

(22) Filed: Oct. 23, 2019

(65) Prior Publication Data

US 2020/0216528 A1   Jul. 9, 2020

Related U.S. Application Data

(60) Division of application No. 16/242,760, filed on Jan. 8, 2019, now Pat. No. 10,696,741, which is a continuation of application No. PCT/EP2017/067923, filed on Jul. 14, 2017.

(30) Foreign Application Priority Data

Jul. 15, 2016 (GB) .................................... 1612337

(51) Int. Cl.

| C07K 16/28 | (2006.01) |
| A61P 17/06 | (2006.01) |
| A61P 19/02 | (2006.01) |
| A61P 17/02 | (2006.01) |
| C07K 16/24 | (2006.01) |
| C07K 14/54 | (2006.01) |
| C12N 15/62 | (2006.01) |

(52) U.S. Cl.
CPC ............ *C07K 16/244* (2013.01); *A61P 17/02* (2018.01); *A61P 17/06* (2018.01); *A61P 19/02* (2018.01); *C07K 14/54* (2013.01); *C07K 16/2866* (2013.01); *C12N 15/62* (2013.01); *C07K 2317/22* (2013.01); *C07K 2317/33* (2013.01); *C07K 2317/34* (2013.01); *C07K 2317/515* (2013.01); *C07K 2317/565* (2013.01); *C07K 2317/732* (2013.01); *C07K 2317/92* (2013.01)

(58) Field of Classification Search
CPC .......... C07K 16/2866; C07K 2317/565; C07K 2317/515; C07K 2317/22; A61K 2039/505
See application file for complete search history.

(56) References Cited

U.S. PATENT DOCUMENTS

| 5,892,019 A | 4/1999 | Schlom et al. |
| 2015/0191548 A1 | 7/2015 | De Haard et al. |

FOREIGN PATENT DOCUMENTS

| WO | WO 2004/085476 A2 | 10/2004 |
| WO | WO 2006/047249 A1 | 5/2006 |
| WO | WO 2010/001251 A1 | 1/2010 |
| WO | WO 2011/061119 A1 | 5/2011 |
| WO | WO 2011/080350 A1 | 7/2011 |
| WO | WO 2014/033252 A1 | 3/2014 |

OTHER PUBLICATIONS

Paul, "Structure and Function of Immunoglobulins", Fundamental Immunology, $3^{rd}$ Edition, Raven Press, New York, 1993, pp. 292-295.
Vajdos et al., "Comprehensive Functional Maps of the Antingen-Binding Site of an Anti-ErbB2 Antibody Obtained with Shotgun Scanning Mutagenesis", Journ Mol Biol., 2002, 320: 415-428.
Boniface et al. (2007) "A role for T cell-derived interleukin 22 in psoriatic skin inflammation," Clin Exp Immunol. 150:407-415.
Caron et al. (1992) "Engineered humanized dimeric forms of IgG are more effective antibodies," J. Exp. Med. 176:1191-1195.
Chan et al. (2010) "Therapeutic antibodies for autoimmunity and inflammation," Nat. Rev. Immunol. 10:301-316.
Dondelinger et al. (Oct. 2018) "Understanding the Significance and Implications of Antibody Numbering and Antigen-Binding Surface/Residue Definition", Frontiers in Immunology, vol. 9.
Dumoutier et al. (2009) "New activation modus of STAT3: a tyrosine-less region of the interleukin-22 receptor recruits STAT3 by interacting with its coiled-coil domain," J Biol Chem. 284(39):26377-84.
Graham et al. (1977) "Characteristics of a human cell line transformed by DNA from human adenovirus type 5," J. Gen. Virol. 36:59-74.
Harlow et al. (1988) Antibodies, A Laboratory Manual. Cold Spring Harbor Laboratory Press. Cold Spring Harbor, New York. pp. 567-569.
Holliger et al. (2005) "Engineered antibody fragments and the rise of single domains," Nature Biotechnol. 23:1126-36.

(Continued)

*Primary Examiner* — Ruixiang Li
(74) *Attorney, Agent, or Firm* — Lathrop GPM LLP; James H. Velema, Esq.

(57) ABSTRACT

The present invention relates to antibodies and antigen binding fragments thereof which bind to the cytokine receptor IL-22R, particularly human IL-22R. The invention also relates to pharmaceutical compositions comprising said antibodies or antigen binding fragments thereof, and methods of treating psoriasis, psoriatic arthritis or atopic dermatitis.

26 Claims, 18 Drawing Sheets
Specification includes a Sequence Listing.

(56) References Cited

OTHER PUBLICATIONS

Honegger (2001) "Human Vλ Germline Sequences (VBase)," University of Zurich. Accessible on the Internet at URL: http://www.bioc.uzh.ch/antibody/Sequences/Germlines/VBase_hVL.html. [Last Accessed Dec. 4, 2017].
Jones et al. (2008) "Structure of IL-22 bound to its high-affinity IL-22R1 chain," Structure. 16(9):1333-1344.
Kabat et al. (1977) "Unusual distributions of amino acids in complementarity-determining (hypervariable) segments of heavy and light chains of immunoglobulins and their possible roles in specificity of antibody-combining sites," J. Biol. Chem. 252:6609-6616.
Lefranc et al. (1999) "IMGT, the international ImMunoGeneTics database," Nucleic Acids Res. 27:209-212.
Ma et al. (2008) "IL-22 is required for Th17 cell-mediated pathology in a mouse model of psoriasis-like skin inflammation," J Clin. Invest. 118:597-607.
MacCallum et al. (1996) "Antibody-antigen interactions: contact analysis and binding site topography," J. Mol. Biol. 262:732-745.
Martin et al. (1996) "Structural Families in Loops of Homologous Proteins: Automatic Classification, Modelling and Application to Antibodies," J. Mol. Biol. 263(5):800-15.
Mather et al. (1982) "Culture of testicular cells in hormone-supplemented serum-free medium," Annals N.Y. Acad. Sci. 383:44-68.
Mather (1980) "Establishment and Characterization of Two Distinct Mouse Testicular Epithelial Cell Line," Biol. Reprod. 23:243-251.
Morea et al. (2000) "Antibody Modeling: Implications for Engineering and Design," Methods. 20:267-279.
Natsume et al. (2009) "Improving effector functions of antibodies for cancer treatment: Enhancing ADCC and CDC," Drug Design Development and Therapy. 3:7-16.
Ono et al. (1999) "The humanized anti-HM1.24 antibody effectively kills multiple myeloma cells by human effector cell-mediated cytotoxicity," Mol. Immunol. 36:387-395.
Poirier et al. (Mar. 2016) "Selective CD28 antagonist prevents Aldara-induced skin inflammation in non-human primates," Exp Dermatol. 25(3):233-4.
Poirier et al. (Jan. 1, 2016) "Selective CD28 Antagonist Blunts Memory Immune Responses and Promotes Long-Term Control of Skin Inflammation in Nonhuman Primates," J. Immunol. 196(1):274-83.
Qu et la. (1999) "Humanization of Immu31, an alpha-fetoprotein-specific antibody," Clin. Cancer Res. 5(Suppl):3095s-3100s.
Roux et al. (1988) "Comparisons of the ability of human IgG3 hinge mutants, IgM, IgE, and IgA2, to form small immune complexes: a role for flexibility and geometry," J. Immunol. 161:4083-90.
Rudikoff et al. (Mar. 1982) "Single amino acid substitution altering antigen-binding specificity", Proc Natl Acad Sci USA, vol. 79, pp. 1979-1983.
Sabat et al. (Jan. 2014) "Therapeutic opportunities of the IL-22-IL-22R1 system," Nat. Rev. Drug Discov. 13(1):21 -38.
Shopes (1992) "A genetically engineered human IgG mutant with enhanced cytolytic activity," J. Immunol. 148:2918-2922.
Tatusova et al. (1999) "Blast 2 sequences—a new tool for comparing protein and nucleotide sequences," FEMS Microbiol Lett. 174:247-250.
Tatusova et al. (1999) "Erratum: Blast 2 sequences—a new tool for comparing protein and nucleotide sequences [FEMS Microbiol. 174 (1999) 247-250]," FEMS Microbiol. Lett. 177:187-188.
Tomlinson et al. (1995) "The structural repertoire of the human V kappa domain," EMBO J. 14:4628-4638.
Tramontano et al. (1989) "Structural determinants of the conformations of mediumsized loops in proteins," Proteins. 6:382-94.
Tramontano et al. (1990) "Framework residue 71 is a major determinant of the position and conformation of the second hypervariable region in the VH domains of immunoglobulins," J. Mol. Biol. 215:175-182.
Urlaub et al. (1980) "Isolation of Chinese hamster cell mutants deficient in dihydrofolate reductase activity," Proc. Natl. Acad. Sci. USA. 77:4216-20.
Van Belle et al. (2012) "IL-22 is required for imiquimod-induced psoriasiform skin inflammation in mice," J. Immunol. 188(1):462-9.
Vinter et al. (Dec. 10, 2014) "Aldara®-induced skin inflammation: studies of patients with psoriasis," Br J Dermatol. 172(2):345-53.
Wang et al. (2007) "Antibody structure, instability, and formulation," Journal of Pharmaceutical Sciences. 96:1-26.
Williams et al. (1996) "Sequence and evolution of the human germline V lambda repertoire," J. Mol. Biol. 264:220-232.
Yamane-Ohnuki et al. (2009) "Production of therapeutic antibodies with controlled fucosylation," mAbs. 1(3):230-26.
International Search Report with Written Opinion corresponding to International Patent Application No. PCT/EP2017/067923, dated Nov. 15, 2017.
U.S. Appl. No. 16/242,760 / 2019/0127459 / U.S. Pat. No. 10,696,741, filed Jan. 8, 2019 / May 2, 2019 / Jun. 30, 2020, Christophe Frederic Jerome Blanchetot.
U.S. Appl. No. 16/661,757 / 2020/0157207, filed Oct. 23, 2019 / May 21, 2020, Christophe Frederic Jerome Blanchetot.
U.S. Appl. No. 16/661,783 / 2020/0216528, filed Oct. 23, 2019 / Jul. 9, 2020, Christophe Frederic Jerome Blanchetot.
Li et al., "Temporal associations between interleukin 22 and the extracellular domains of IL-22R and IL-10R2", International Immunopharmacology, 2004, 4: 693-708.
Dudakov et al., "Interleukin-22: immunobiology and pathology", Annu Rev Innunol., Mar. 21, 2015, 33: 747-785.
Singer et al., "Structure of Proteins", Genes and Genomes, A Changing Perspective, 1998, pp. 63-64, with English translation.

Fig.2

```
  1  MRTLLTILTV  GSLAAHAPED  PSDLLQHVKF  QSSNFENILT  WDSGPEGTPD
 51  TVYSIEYKTY  GERDWVAKKG  CQRITRKSCN  LTVETGNLTE  LYYARVTAVS
101  AGGRSATKMT  DRFSSLQHTT  LKPPDVTCIS  KVRSIQMIVH  PTPTPIRAGD
151  GHRLTLEDIF  HDLFYHLELQ  VNRTYQMHLG  GKQREYEFFG  LTPDTEFLGT
201  IMICVPTWAK  ESAPYMCRVK  TLPDRTWTYS  FSGAFLFSMG  FLVAVLCYLS
251  YRYVTKPPAP  PNSLNVQRVL  TFQPLRFIQE  HVLIPVFDLS  GPSSLAQPVQ
301  YSQIRVSGPR  EPAGAPQRHS  LSEITYLGQP  DISILQPSNV  PPPQILSPLS
351  YAPNAAPEVG  PPSYAPQVTP  EAQFPFYAPQ  AISKVQPSSY  APQATPDSWP
401  PSYGVCMEGS  GKDSPTGTLS  SPKHLRPKGQ  LQKEPPAGSC  MLGGLSLQEV
451  TSLAMEESQE  AKSLHQPLGI  CTDRTSDPNV  LHSGEEGTPQ  YLKGQLPLLS
501  SVQIEGHPMS  LPLQPPSRPC  SPSDQGPSPW  GLLESLVCPK  DEAKSPAPET
551  SDLEQPTELD  SLFRGLALTV  QWES
```

Fig.3

```
   1 ATGAGGACGC TGCTGACCAT CTTGACTGTG GGATCCCTGG CTGCTCACGC CCCTGAGGAC
  61 CCCTCGGATC TGCTCCAGCA CGTGAAATTC CAGTCCAGCA ACTTTGAAAA CATCCTGACG
 121 TGGGACAGCG GGCCGGAGGG CACCCCAGAC ACGGTCTACA GCATCGAGTA TAAGACGTAC
 181 GGAGAGAGGG ACTGGGTGGC AAAGAAGGGC TGTCAGCGGA TCACCCGGAA GTCCTGCAAC
 241 CTGACGGTGG AGACGGGCAA CCTCACGGAG CTCTACTATG CCAGGGTCAC CGCTGTCAGT
 301 GCGGGAGGCC GGTCAGCCAC CAAGATGACT GACAGGTTCA GCTCTCTGCA GCACACTACC
 361 CTCAAGCCAC CTGATGTGAC CTGTATCTCC AAAGTGAGAT CGATTCAGAT GATTGTTCAT
 421 CCTACCCCCA CGCCCATCCG TGCAGGCGAT GGCCACCGGC TAACCCTGGA AGACATCTTC
 481 CATGACCTGT TCTACCACTT AGAGCTCCAG GTCAACCGCA CCTACCAAAT GCACCTTGGA
 541 GGGAAGCAGA GAGAATATGA GTTCTTCGGC CTGACCCCTG ACACAGAGTT CCTTGGCACC
 601 ATCATGATTT GCGTTCCCAC CTGGGCCAAG GAGAGTGCCC CCTACATGTG CCGAGTGAAG
 661 ACACTGCCAG ACCGGACATG GACCTACTCC TTCTCCGGAG CCTTCCTGTT CTCCATGGGC
 721 TTCCTCGTCG CAGTACTCTG CTACCTGAGC TACAGATATG TCACCAAGCC GCCTGCACCT
 781 CCCAACTCCC TGAACGTCCA GCGAGTCCTG ACTTTCCAGC CGCTGCGCTT CATCCAGGAG
 841 CACGTCCTGA TCCCTGTCTT TGACCTCAGC GGCCCCAGCA GTCTGGCCCA GCCTGTCCAG
 901 TACTCCCAGA TCAGGGTGTC TGGACCCAGG GAGCCTGCAG GAGCTCCACA GCGGCATAGC
 961 CTGTCCGAGA TCACCTACTT AGGGCAGCCA GACATCTCCA TCCTCCAGCC CTCCAACGTG
1021 CCACCTCCCC AGATCCTCTC CCCACTGTCC TATGCCCCAA ACGCTGCCCC TGAGGTCGGG
1081 CCCCCATCCT ATGCACCTCA GGTGACCCCC GAAGCTCAAT TCCCATTCTA CGCCCCACAG
1141 GCCATCTCTA AGGTCCAGCC TTCCTCCTAT GCCCCTCAAG CCACTCCGGA CAGCTGGCCT
1201 CCCTCCTATG GGTATGCAT GGAAGGTTCT GGCAAAGACT CCCCCACTGG GACACTTTCT
1261 AGTCCTAAAC ACCTTAGGCC TAAAGGTCAG CTTCAGAAAG AGCCACCAGC TGGAAGCTGC
1321 ATGTTAGGTG GCCTTTCTCT GCAGGAGGTG ACCTCCTTGG CTATGGAGGA ATCCCAAGAA
1381 GCAAAATCAT TGCACCAGCC CCTGGGGATT TGCACAGACA GAACATCTGA CCCAAATGTG
1441 CTACACAGTG GGGAGGAAGG GACACCACAG TACCTAAAGG CCAGCTCCC CCTCCTCTCC
1501 TCAGTCCAGA TCGAGGGCCA CCCCATGTCC CTCCCTTTGC AACCTCCTTC CCGTCCATGT
1561 TCCCCCTCGG ACCAAGGTCC AAGTCCCTGG GGCCTGCTGG AGTCCCTTGT GTGTCCCAAG
1621 GATGAAGCCA AGAGCCCAGC CCCTGAGACC TCAGACCTGG AGCAGCCCAC AGAACTGGAT
1681 TCTCTTTTCA GAGGCCTGGC CCTGACTGTG CAGTGGGAGT CCTGA
```

Fig. 5A

```
BC029273.1           VRSIQMIVHPTPTPIRAGDGHRLTLEDIFHDLFYHLELQVNRTYQM--HLGGKQREYEFFGLTPDTEFLGTIMICVPTWA    SEQ ID NO: 94
IL22RA1-ECD-HIS      ............................................--.........................       SEQ ID NO: 94
01113239(rhesus)     ............................................--....E....................       SEQ ID NO: 95
FS371752(CYNO)       ...........................Y...S...........VN..........................       SEQ ID NO: 96
FS368027(CYNO)       ...........................Y...S...........VN..........................       SEQ ID NO: 97
FS371904(CYNO)       ...........................Y...S...........--..........................       SEQ ID NO: 98
```

*residue directly involved in IL22 binding.

Fig. 5B

```
human   1   LRLEYLIRLTIGYRLNGTAATMGWSCIILFLVATATGVHSPEDPSDLLQHVKFQSSNFENLLTWDSGPEGTPDTVYSIEYKTYGERDWVAKKGCQRITRK
rhesus  1   ....................................................................................................
cyno    1   ....................................................................................................

human   101 SCNLTVETGNLTELYYARVTAVSAGGRSARKMTDRFSSLQHTTLKPPDVTCISKVRSIQMIVHPTPTPIRAGDHRLTLEDIFHDLFYHLELQVNRTYQM
rhesus  101 ........H..................N....A...........P...........................................
cyno    101 ........H..................N....A...........P......................................Y..S.

→huFc
human   201 HLGGKQREYEFFGLTPDTEFLGTIMICVPTWAKESAPYMCRVKTLPDRTWT  IEGRDMDPKSCDKTHTCPPCPAPELLGRPSVFLFPPKPKDTL   SEQ ID NO: 99
rhesus  201 .....E..................S.K......R.................  ...................G.....................    SEQ ID NO: 100
cyno    200 ........................S.K......R.................  ...................G.....................    SEQ ID NO: 101
                                  loop6 (PTW; IL22 binding, next to deletion in cyIL22R)
```

ANTI-IL-22R ANTIBODIES

RELATED APPLICATIONS

This application is a division of U.S. patent application Ser. No. 16/242,760, filed Jan. 8, 2019, which is a continuation of International Patent Application No. PCT/EP2017/067923, filed Jul. 14, 2017, which claims priority to Great Britain Patent Application No. 1612337.4, filed Jul. 15, 2016, the entire disclosures of which are hereby incorporated herein by reference.

SEQUENCE LISTING

The instant application contains a Sequence Listing which has been submitted electronically in ASCII format and is hereby incorporated by reference in its entirety. Said ASCII copy, created on Oct. 23, 2019, is named 616864_AGX5-034PCCONDV2_Sequence_Listing.txt and is 63,200 bytes in size.

FIELD OF THE INVENTION

The present invention relates to antibodies and antigen binding fragments thereof which bind to the cytokine receptor IL-22R, particularly human IL-22R. The IL-22R antibodies and antigen binding fragments of the invention exhibit distinct properties, particularly distinct combinations of properties, as compared with IL-22R antibodies described in the prior art.

BACKGROUND TO THE INVENTION

IL-22R (also known as IL-22R1 and IL-22RA) is a type II cytokine receptor selectively expressed on skin and epithelial cells. This receptor mediates signalling via three cytokines: interleukin 22 (IL-22), interleukin 20 (IL-20) and interleukin 24 (IL-24). Cytokine signalling via the IL-22R requires the formation of heterodimeric complexes at the cell surface. As shown in FIG. 1, IL-22 binds to and signals via a complex consisting of IL-22R and IL-10Rβ (also known as IL-10R2), whereas IL-20 and IL-24 bind to and signal via a heterodimeric complex consisting of IL-22R and IL-20Rβ (also known as IL-20R2).

Interleukin-22 is a cytokine expressed by immune cells, particularly activated dendritic cells and T cells. Once produced by the immune system, IL-22 exerts its biological effects by binding to and activating IL-22R on epithelial cells. Activation of the IL-22R-IL-10Rβ complex downstream of IL-22 binding leads to pro-inflammatory responses, the induction of anti-microbial proteins that are critical for host defence against bacterial pathogens, and protective effects in some organs such as the lungs and liver. IL-22 has also been implicated in disease pathology, particularly in the development of inflammatory disorders such as psoriasis, psoriatic arthritis and atopic dermatitis (Ma et al. J Clin. Invest. 118: 597-607 (2008); Van Belle et al. J Immunol. January 1; 188(1):462-9 (2012); Sabat et al. Nat. Rev. Drug Discov. 13(1): 21-38 (2014)).

The crystal structure of IL-22 in complex with the extracellular domain of IL-22R has been solved, and has provided important insights into how this ligand associates with its receptor (Jones et al. Structure 16(9): 1333-1344 (2008)). The extracellular region of IL-22R includes two fibronectin type III (FBNIII) domains (D1 and D2) oriented at approximately right angles to one another. Five loops located at the interface of these domains are primarily responsible for engaging IL-22 residues in the ligand-receptor complex. The IL-22 residues that contribute to receptor binding are clustered at two sites in the ligand, site 1a and site 1b. Insights into the critical residues contributed by both the receptor and the ligand have revealed ways in which this interaction could be disrupted to abrogate IL-22 signalling as a therapeutic strategy.

Interleukin-20 and interleukin-24 are expressed by monocytes and keratinocytes and similar to IL-22, these cytokines have been found to play a role in skin homeostasis and pathology. It follows, that strategies to inhibit or reduce signalling downstream of IL-22R by blocking the binding of ligands that activate this receptor could have therapeutic utility, particularly in the treatment of skin conditions such as psoriasis and atopic dermatitis.

Antibodies that bind to IL-22R and block the interaction between IL-22 and IL-22R have been developed. For example, WO2011/061119 describes a humanised IL-22R antibody produced from a mouse anti-human monoclonal antibody originally described in WO2006/047249. This humanised antibody, which will be referred to herein as "280-346-TSY" was shown to inhibit IL-22 signalling via IL-22RA in a cell proliferation assay, and inhibited IL-23-induced ear inflammation in a mouse model of psoriasis.

SUMMARY OF INVENTION

The present invention improves upon the state of the art by providing antibodies, or antigen binding fragments thereof, which bind to the cytokine receptor IL-22R, and exhibit properties that are different to IL-22R antibodies described in the prior art. The antibodies or antigen binding fragments thereof typically exhibit combinations of properties that are distinct and in certain cases superior, to the properties of the prior art IL-22R antibodies, particularly the humanised IL-22R antibody described in WO2011/061119. The properties of these antibodies can be particularly advantageous with regard to use in human therapy, particularly for the treatment of conditions such as psoriasis, psoriatic arthritis and atopic dermatitis.

In a first aspect, the present invention provides an antibody, or an antigen binding fragment thereof, which binds to human IL-22R, wherein the antibody or antigen binding fragment thereof binds to an epitope within the IL-22R protein that does not include Tyr60.

In certain embodiments, the antibodies or antigen binding fragments thereof possess one or more additional properties selected from the following:
 (i) the ability to bind an epitope of human IL-22R located at least in part in the D2 domain of the IL-22R protein;
 (ii) the ability to bind human IL-22R with high affinity;
 (iii) the ability to block binding of IL-22 to human IL-22R;
 (iv) the ability to inhibit IL-22 dependent activation of IL-22R;
 (v) the ability to inhibit IL-20 dependent activation of IL-22R;
 (vi) the ability to inhibit IL-22 and IL-20 dependent activation of IL-22R; and
 (vii) lack of cross-reactivity with murine IL-22R.

The antibodies or antigen binding fragments may exhibit high human homology, as defined elsewhere herein. In certain embodiments, the antibodies or antigen binding fragments thereof comprise a heavy chain variable domain (VH) and a light chain variable domain (VL) wherein the VH and/or VL domains or one or more complementarity determining regions (CDRs) thereof are derived from an animal of the Camelidae family i.e. are camelid-derived. The antibodies or antigen binding fragments exhibiting high human homology or having at least one camelid-derived CDR sequence, VH and/or VL domain may be humanised or germlined variants of VH or VL domains from camelid conventional antibodies, wherein the terms "humanised" and "germlined" are as defined elsewhere herein.

In non-limiting embodiments the invention provides the following antibodies, or antigen binding fragments thereof, which are defined by reference to specific structural characteristics, i.e. specified amino acid sequences of either the CDRs (one or more of SEQ ID NOs: 2, 4, 6, 9, 11, 13, 34, 36, 41, 43 (heavy chain CDRs) or SEQ ID NOs: 16, 18, 20, 23, 25, 27, 47, 54, 57, 59 (light chain CDRs)) or entire variable domains (one or more of SEQ ID NOs: 29, 31, 63, 65 (heavy chain variable domains) or SEQ ID NOs: 30, 32, 62, 64, 66 (light chain variable domains)). All of these antibodies bind to the human cytokine receptor IL-22R.

In particular embodiments, the antibodies defined by the following structural characteristics may exhibit high human homology, as defined herein. The antibodies may be monoclonal antibodies produced by recombinant means. The CDRs of the following IL-22R antibodies may be camelid-derived, i.e. derived from conventional antibodies raised by immunisation of camelids (specifically llama). The invention also provides humanised or human germlined variants, affinity variants and variants containing conservative amino acid substitutions, as defined herein.

Embodiments of the IL-22R antibodies of the invention are now further described by reference to structural characteristics.

In one embodiment, there is provided an antibody or antigen binding fragment thereof, which binds to the cytokine receptor IL-22R, said antibody or antigen binding fragment comprising a heavy chain variable domain (VH) comprising a heavy chain CDR3 selected from:

SEQ ID NO: 6 [VGFSGTYYSES], or sequence variant thereof

SEQ ID NO: 13 [PPGPFKAHYNGMKY], or sequence variant thereof,

SEQ ID NO: 43 [PPGPFKAHYNGAKY], or sequence variant thereof, wherein the sequence variant comprises one, two or three amino acid substitutions (e.g. conservative substitutions, humanising substitutions or affinity variants) in the recited sequence.

The heavy chain variable domain of the antibody or antigen binding fragment thereof may alternatively or in addition comprise a heavy chain CDR2 selected from:

SEQ ID NO: 4 [SIYNDGSNTAYSDSVKG], or sequence variant thereof,

SEQ ID NO: 11 [GIHISGGITYYLDSVKG], or sequence variant thereof,

SEQ ID NO: 36 [SIYNDASNTAYSDSVKG], or sequence variant thereof,

SEQ ID NO: 41 [GIHISGGITYYTDSVKG], or sequence variant thereof, wherein the sequence variant comprises one, two or three amino acid substitutions (e.g. conservative substitutions, humanising substitutions or affinity variants) in the recited sequence.

The heavy chain variable domain of the antibody or antigen binding fragment thereof may alternatively or in addition comprise a heavy chain CDR1 selected from:

SEQ ID NO: 2 [SYDMS], or sequence variant thereof,
SEQ ID NO: 9 [SYFMS], or sequence variant thereof,
SEQ ID NO: 34 [SYDMN], or sequence variant thereof, wherein the sequence variant comprises one, two or three amino acid substitutions (e.g. conservative substitutions, humanising substitutions or affinity variants) in the recited sequence.

Alternatively or in addition, the antibodies or antigen binding fragment thereof, which bind to the cytokine receptor IL-22R, may comprise a light chain variable domain (VL) comprising a light chain CDR3 selected from:

SEQ ID NO: 20 [QSGSSSANAV], or sequence variant thereof,

SEQ ID NO: 27 [ASYRLYADYV], or sequence variant thereof,

SEQ ID NO: 54 [QSGSSSSNAV], or sequence variant thereof, wherein the sequence variant comprises one, two or three amino acid substitutions (e.g. conservative substitutions, humanising substitutions or affinity variants) in the recited sequence.

The light chain variable domain of the antibody or antigen binding fragment thereof may alternatively or in addition comprise a light chain CDR2 selected from:

SEQ ID NO: 18 [GNNNRPS], or sequence variant thereof
SEQ ID NO: 25 [KVNTRSS], or sequence variant thereof, SEQ ID NO: 47 [GQNNRPS], or sequence variant thereof, SEQ ID NO: 59 [EVNKRSS], or sequence variant thereof, wherein the sequence variant comprises one, two or three amino acid substitutions (e.g. conservative substitutions, humanising substitutions or affinity variants) in the recited sequence.

The light chain variable domain of the antibody or antigen binding fragment thereof may alternatively or in addition comprise a light chain CDR1 selected from:

SEQ ID NO: 16 [QGGYYAH], or sequence variant thereof

SEQ ID NO: 23 [TGTSRDIGDYNYVS], or sequence variant thereof,

SEQ ID NO: 57 [TGTSSDIGSYNYVS], or sequence variant thereof, wherein the sequence variant comprises one, two or three amino acid substitutions (e.g. conservative substitutions, humanising substitutions or affinity variants) in the recited sequence.

In certain embodiments, there is provided an antibody or antigen binding fragment thereof, which binds to the cytokine receptor IL-22R, the antibody or antigen binding fragment thereof comprising a combination of variable heavy chain CDR3 (HCDR3), variable heavy chain CDR2 (HCDR2) and variable heavy chain CDR1 (HCDR1) wherein the combination is selected from the group consisting of:

(i) HCDR3 comprising SEQ ID NO: 6; HCDR2 comprising SEQ ID NO: 36; HCDR1 comprising SEQ ID NO: 34;

(ii) HCDR3 comprising SEQ ID NO: 43; HCDR2 comprising SEQ ID NO: 41; HCDR1 comprising SEQ ID NO: 9;

(iii) HCDR3 comprising SEQ ID NO: 6; HCDR2 comprising SEQ ID NO: 4; HCDR1 comprising SEQ ID NO: 2; and (iv) HCDR3 comprising SEQ ID NO: 13; HCDR2 comprising SEQ ID NO: 11; HCDR1 comprising SEQ ID NO: 9.

Alternatively or in addition, the antibodies or antigen binding fragment thereof, which bind to the cytokine receptor IL-22R may comprise a combination of variable light chain CDR3 (LCDR3), variable light chain CDR2 (LCDR2) and variable light chain CDR1 (LCDR1) selected from the group consisting of:

(i) LCDR3 comprising SEQ ID NO: 54; LCDR2 comprising SEQ ID NO: 47; LCDR1 comprising SEQ ID NO: 16;

(ii) LCDR3 comprising SEQ ID NO: 27; LCDR2 comprising SEQ ID NO: 59; LCDR1 comprising SEQ ID NO: 57;

(iii) LCDR3 comprising SEQ ID NO: 20; LCDR2 comprising SEQ ID NO: 47; LCDR1 comprising SEQ ID NO: 16;

(iv) LCDR3 comprising SEQ ID NO: 20; LCDR2 comprising SEQ ID NO: 18; LCDR1 comprising SEQ ID NO: 16; and (v) LCDR3 comprising SEQ ID NO: 27; LCDR2 comprising SEQ ID NO: 25; LCDR1 comprising SEQ ID NO: 23.

In certain embodiments, provided herein are antibodies or antigen binding fragments thereof, which bind to the cytokine receptor IL-22R, wherein the antibodies or antigen binding fragments comprise a combination of variable heavy chain CDR3 (HCDR3), variable heavy chain CDR2 (HCDR2) and variable heavy chain CDR1 (HCDR1), variable light chain CDR3 (LCDR3), variable light chain CDR2 (LCDR2) and variable light chain CDR1 (LCDR1) according to the embodiments described below.

In one embodiment, provided herein is an antibody or antigen binding fragment thereof, which binds to the cytokine receptor IL-22R and comprises the combination of VH and VL CDR sequences: HCDR3 comprising SEQ ID NO: 6; HCDR2 comprising SEQ ID NO: 36; HCDR1 comprising SEQ ID NO: 34; LCDR3 comprising SEQ ID NO: 54; LCDR2 comprising SEQ ID NO: 47; and LCDR1 comprising SEQ ID NO: 16.

In one embodiment, provided herein is an antibody or antigen binding fragment thereof, which binds to the cytokine receptor IL-22R and comprises the combination of VH and VL CDR sequences: HCDR3 comprising SEQ ID NO: 43; HCDR2 comprising SEQ ID NO: 41; HCDR1 comprising SEQ ID NO: 9; LCDR3 comprising SEQ ID NO: 27; LCDR2 comprising SEQ ID NO: 59; and LCDR1 comprising SEQ ID NO: 57.

In one embodiment, provided herein is an antibody or antigen binding fragment thereof, which binds to the cytokine receptor IL-22R and comprises the combination of VH and VL CDR sequences: HCDR3 comprising SEQ ID NO: 6; HCDR2 comprising SEQ ID NO: 4; HCDR1 comprising SEQ ID NO: 2; LCDR3 comprising SEQ ID NO: 20; LCDR2 comprising SEQ ID NO: 47; and LCDR1 comprising SEQ ID NO: 16.

In one embodiment, provided herein is an antibody or antigen binding fragment thereof, which binds to the cytokine receptor IL-22R and comprises the combination of VH and VL CDR sequences: HCDR3 comprising SEQ ID NO: 6; HCDR2 comprising SEQ ID NO: 4; HCDR1 comprising SEQ ID NO: 2; LCDR3 comprising SEQ ID NO: 20; LCDR2 comprising SEQ ID NO: 18; and LCDR1 comprising SEQ ID NO: 16.

In one embodiment, provided herein is an antibody or antigen binding fragment thereof, which binds to the cytokine receptor IL-22R and comprises the combination of VH and VL CDR sequences: HCDR3 comprising SEQ ID NO: 13; HCDR2 comprising SEQ ID NO: 11; HCDR1 comprising SEQ ID NO: 9; LCDR3 comprising SEQ ID NO: 27; LCDR2 comprising SEQ ID NO: 25; and LCDR1 comprising SEQ ID NO: 23.

In certain embodiments, provided herein are antibodies or antigen binding fragments thereof, which bind to the cytokine receptor IL-22R, wherein the antibodies or antigen binding fragments comprise a heavy chain variable domain (VH) selected from the following:

(i) a VH comprising or consisting of the amino acid sequence of SEQ ID NO: 29 or 31

(ii) an affinity variant or human germlined variant of a VH comprising or consisting of the amino acid sequence of SEQ ID NO: 29 or 31; or (iii) a VH comprising or consisting of an amino acid sequence having at least 80%, at least 85%, at least 90%, at least 95%, at least 97%, at least 98%, at least 99% identity to the amino acid sequence of SEQ ID NO: 29 or 31.

Alternatively or in addition, the antibodies or antigen binding fragments may comprise a light chain variable domain (VL) selected from the following:

(i) a VL comprising or consisting of the amino acid sequence of SEQ ID NO: 30, 32 or 62

(ii) an affinity variant or human germlined variant of a VH comprising or consisting of the amino acid sequence of SEQ ID NO: 30, 32 or 62; or (iii) a VL comprising or consisting of an amino acid sequence having at least 80%, at least 85%, at least 90%, at least 95%, at least 97%, at least 98%, at least 99% identity to the amino acid sequence of SEQ ID NO: 30, 32 or 62.

For embodiments wherein the domains of the antibodies or antigen binding fragments are defined by a particular percentage sequence identity to a reference sequence, the VH and/or VL domains may retain identical CDR sequences to those present in the reference sequence such that the variation is present only within the framework regions.

In certain embodiments, the antibodies of the invention may include the CH1 domain, hinge region, CH2 domain and CH3 domain of a human antibody, in particular human IgG1, IgG2, IgG3 or IgG4.

Particularly preferred antibodies of the present invention are described below.

230C9 and Antibodies Related Thereto

In certain embodiments, there is provided an isolated antibody, or antigen binding fragment thereof, which specifically binds IL-22R, said antibody or antigen binding fragment comprising a heavy chain variable domain wherein:

the variable heavy chain CDR3 sequence is SEQ ID NO:6 [VGFSGTYYSES] or sequence variant thereof;

the variable heavy chain CDR2 sequence is SEQ ID NO:36 [SIYNDASNTAYSDSVKG] or sequence variant thereof; and the variable heavy chain CDR1 sequence is SEQ ID NO:34 [SYDMN] or sequence variant thereof, and wherein the sequence variant comprises one, two or three amino acid substitutions (e.g., conservative substitutions, humanising substitutions or affinity variants) in the recited sequence.

The antibody or antigen binding fragment may further comprise a light chain variable domain wherein:

the variable light chain CDR3 sequence is SEQ ID NO:54 [QSGSSSSNAV] or sequence variant thereof;

the variable light chain CDR2 sequence is SEQ ID NO:47 [GQNNRPS] or sequence variant thereof; and the variable light chain CDR1 sequence is SEQ ID NO:16 [QGGYYAH] or sequence variant thereof, and wherein the sequence variant comprises one, two or three amino acid substitutions (e.g., conservative substitutions, humanising substitutions or affinity variants) in the recited sequence.

In certain embodiments, there is provided an isolated antibody, or antigen binding fragment thereof, which specifically binds IL-22R, said antibody or antigen binding fragment comprising a heavy chain variable domain wherein:

the variable heavy chain CDR3 sequence comprises or consists of SEQ ID NO:6 [VGFSGTYYSES];

the variable heavy chain CDR2 sequence comprises or consists of SEQ ID NO:36 [SIYNDASNTAYSDSVKG];

the variable heavy chain CDR1 sequence comprises or consists of SEQ ID NO:34 [SYDMN];

the variable light chain CDR3 sequence comprises or consists of SEQ ID NO:54 [QSGSSSSNAV];

the variable light chain CDR2 sequence comprises or consists of SEQ ID NO:47 [GQNNRPS]; and the variable light chain CDR1 sequence comprises or consists of SEQ ID NO:16 [QGGYYAH].

The antibodies or antigen binding fragments thereof may comprise a heavy chain variable domain (VH) comprising the amino acid sequence of SEQ ID NO: 63 and optionally a light chain variable domain (VL) comprising the amino acid sequence of SEQ ID NO: 64. In certain embodiments, provided herein are monoclonal antibodies or antigen binding fragments thereof, comprising a heavy chain variable domain and a light chain variable domain, the heavy chain variable domain comprising a VH sequence with at least 85% sequence identity, or at least 90% sequence identity, or at least 95% sequence identity, or at least 97%, 98% or 99% sequence identity, to the amino acid sequence shown as SEQ ID NO:63 and/or the light chain variable domain comprising a VL with at least 85% sequence identity, or at least 90% sequence identity, or at least 95% sequence identity, or at least 97%, 98% or 99% sequence identity, to the amino acid sequence shown as SEQ ID NO:64. For embodiments wherein the domains of the antibodies or antigen binding fragments are defined by a particular percentage sequence identity to a reference sequence, the VH and/or VL domains may retain identical CDR sequences to those present in the reference sequence such that the variation is present only within the framework regions. In certain embodiments, the antibodies or antigen binding fragments comprising heavy chain variable domains and/or light chain variable domains defined as having a particular percentage identity to SEQ ID NOs: 63 and 64, respectively will have the following CDR sequences:

a variable heavy chain CDR3 sequence comprising or consisting of SEQ ID NO:6 [VGFSGTYYSES];

a variable heavy chain CDR2 sequence comprising or consisting of SEQ ID NO:36 [SIYNDASNTAYSDSVKG];

a variable heavy chain CDR1 sequence comprising or consisting of SEQ ID NO:34 [SYDMN];

a variable light chain CDR3 sequence comprising or consisting of SEQ ID NO:54 [QSGSSSSNAV];

a variable light chain CDR2 sequence comprising or consisting of SEQ ID NO:47 [GQNNRPS]; and a variable light chain CDR1 sequence comprising or consisting of SEQ ID NO:16 [QGGYYAH].

The antibodies which specifically bind IL-22R may comprise at least one full-length immunoglobulin heavy chain and/or at least one full-length lambda or kappa light chain. In certain embodiments, the antibodies comprise a heavy chain comprising the amino acid sequence of SEQ ID NO: 67 and a light chain comprising the amino acid sequence of SEQ ID NO: 68. In certain embodiments, provided herein are monoclonal antibodies comprising a heavy chain with at least 85% sequence identity, or at least 90% sequence identity, or at least 95% sequence identity, or at least 97%, 98% or 99% sequence identity, to the amino acid sequence shown as SEQ ID NO:67 and/or a light chain with at least 85% sequence identity, or at least 90% sequence identity, or at least 95% sequence identity, or at least 97%, 98% or 99% sequence identity, to the amino acid sequence shown as SEQ ID NO:68. For embodiments wherein the chains of the antibodies are defined by a particular percentage sequence identity to a reference sequence, the heavy chain and/or light chain may retain identical CDR sequences to those present in the reference sequence such that the variation is present only outside the CDR regions.

223G5 and Antibodies Related Thereto

In certain embodiments, there is provided an isolated antibody, or antigen binding fragment thereof, which specifically binds IL-22R, said antibody or antigen binding fragment comprising a heavy chain variable domain wherein:

the variable heavy chain CDR3 sequence is SEQ ID NO:43 [PPGPFKAHYNGAKY] or sequence variant thereof;

the variable heavy chain CDR2 sequence is SEQ ID NO:41 [GIHISGGITYYTDSVKG] or sequence variant thereof; and the variable heavy chain CDR1 sequence is SEQ ID NO:9 [SYFMS] or sequence variant thereof, and wherein the sequence variant comprises one, two or three amino acid substitutions (e.g., conservative substitutions, humanising substitutions or affinity variants) in the recited sequence.

The antibody or antigen binding fragment may further comprise a light chain variable domain wherein:

the variable light chain CDR3 sequence is SEQ ID NO:27 [ASYRLYADYV] or sequence variant thereof;

the variable light chain CDR2 sequence is SEQ ID NO:59 [EVNKRSS] or sequence variant thereof; and the variable light chain CDR1 sequence is SEQ ID NO:57 [TGTSSDIGSYNYVS] or sequence variant thereof, and wherein the sequence variant comprises one, two or three amino acid substitutions (e.g., conservative substitutions, humanising substitutions or affinity variants) in the recited sequence.

In certain embodiments, there is provided an isolated antibody, or antigen binding fragment thereof, which specifically binds IL-22R, said antibody or antigen binding fragment comprising a heavy chain variable domain wherein:

the variable heavy chain CDR3 sequence comprises or consists of SEQ ID NO:43 [PPGPFKAHYNGAKY];

the variable heavy chain CDR2 sequence comprises or consists of SEQ ID NO:41 [GIHISGGITYYTDSVKG];

the variable heavy chain CDR1 sequence comprises or consists of SEQ ID NO:9 [SYFMS];

the variable light chain CDR3 sequence comprises or consists of SEQ ID NO:27 [ASYRLYADYV];

the variable light chain CDR2 sequence comprises or consists of SEQ ID NO:59 [EVNKRSS]; and the variable light chain CDR1 sequence comprises or consists of SEQ ID NO:57 [TGTSSDIGSYNYVS].

The antibodies or antigen binding fragments thereof may comprise a heavy chain variable domain (VH) comprising the amino acid sequence of SEQ ID NO: 65 and optionally a light chain variable domain (VL) comprising the amino acid sequence of SEQ ID NO: 66. In certain embodiments, provided herein are monoclonal antibodies or antigen binding fragments thereof, comprising a heavy chain variable domain and a light chain variable domain, the heavy chain variable domain comprising a VH sequence with at least 85% sequence identity, or at least 90% sequence identity, or at least 95% sequence identity, or at least 97%, 98% or 99% sequence identity, to the amino acid sequence shown as SEQ ID NO:65 and/or the light chain variable domain comprising a VL with at least 85% sequence identity, or at least 90% sequence identity, or at least 95% sequence identity, or at least 97%, 98% or 99% sequence identity, to the amino acid sequence shown as SEQ ID NO:66. For embodiments wherein the domains of the antibodies or antigen binding fragments are defined by a particular percentage sequence identity to a reference sequence, the VH and/or VL domains may retain identical CDR sequences to those present in the reference sequence such that the variation is present only within the framework regions. In certain embodiments, the antibodies or antigen binding fragments comprising heavy chain variable domains and/or light chain variable domains defined as having a particular percentage identity to SEQ ID NOs: 65 and 66, respectively will have the following CDR sequences:

a variable heavy chain CDR3 sequence comprising or consisting of SEQ ID NO:43 [PPGPFKAHYNGAKY];
a variable heavy chain CDR2 sequence comprising or consisting of SEQ ID NO:41 [GIHISGGITYYTDSVKG];
a variable heavy chain CDR1 sequence comprising or consisting of SEQ ID NO:9 [SYFMS];
a variable light chain CDR3 sequence comprising or consisting of SEQ ID NO:27 [ASYRLYADYV];
a variable light chain CDR2 sequence comprising or consisting of SEQ ID NO:59 [EVNKRSS]; and
a variable light chain CDR1 sequence comprising or consisting of SEQ ID NO:57 [TGTSSDIGSYNYVS].

The antibodies which specifically bind IL-22R may comprise at least one full-length immunoglobulin heavy chain and/or at least one full-length lambda or kappa light chain. In certain embodiments, the antibodies comprise a heavy chain comprising the amino acid sequence of SEQ ID NO: 69 and a light chain comprising the amino acid sequence of SEQ ID NO: 70. In certain embodiments, provided herein are monoclonal antibodies comprising a heavy chain with at least 85% sequence identity, or at least 90% sequence identity, or at least 95% sequence identity, or at least 97%, 98% or 99% sequence identity, to the amino acid sequence shown as SEQ ID NO:69 and/or a light chain with at least 85% sequence identity, or at least 90% sequence identity, or at least 95% sequence identity, or at least 97%, 98% or 99% sequence identity, to the amino acid sequence shown as SEQ ID NO:70. For embodiments wherein the chains of the antibodies are defined by a particular percentage sequence identity to a reference sequence, the heavy chain and/or light chain may retain identical CDR sequences to those present in the reference sequence such that the variation is present only outside the CDR regions.

Where particular antibodies, or antigen-binding regions, are identified as comprising a combination of a VH domain or heavy chain, defined by reference to a specific amino acid sequence, and a VL domain or a light chain, also defined by reference to a specific amino acid sequence, then for each specific VH/VL or heavy chain/light chain combination listed (unless otherwise stated) this definition may be taken to include antibodies, or antigen binding regions, formed by combination of a VH domain/heavy chain having at least 85%, at least 90%, at least 95%, at least 97%, or at least 99% sequence identity to the stated VH/heavy chain amino acid sequence and a VL domain/light chain having at least 75%, at least 80%, at least 85%, at least 90%, at least 95%, at least 97%, or at least 99% sequence identity to the stated VL/light chain amino acid sequence. In each case the domains/chains defined by % sequence identity to the stated domain/chain amino acid sequences may retain identical CDR sequences to those present in the stated VH/VL domain or heavy/light chain amino acid sequences, whilst exhibiting amino acid sequence variation within the framework regions or other regions outside the CDR regions.

Unless otherwise stated in the present application, % sequence identity between two amino acid sequences may be determined by comparing these two sequences aligned in an optimum manner and in which the amino acid sequence to be compared can comprise additions or deletions with respect to the reference sequence for an optimum alignment between these two sequences. The percentage of identity is calculated by determining the number of identical positions for which the amino acid residue is identical between the two sequences, by dividing this number of identical positions by the total number of positions in the comparison window and by multiplying the result obtained by 100 in order to obtain the percentage of identity between these two sequences. For example, it is possible to use the BLAST program, "BLAST 2 sequences" (Tatusova et al, "Blast 2 sequences—a new tool for comparing protein and nucleotide sequences", FEMS Microbiol Lett. 174:247-250) available on the site http://www.ncbi.nlm.nih.gov/gorf/bl2.html, the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program.

The IL-22R antibodies or antigen binding fragments thereof provided herein may each exhibit one, or any combination, of the following properties/features:
the antibody or antigen binding fragment may bind to an epitope within the human IL-22R protein that does not include Tyr60;
the antibody or antigen binding fragment may bind to an epitope located at least in part in the D2 domain of the human IL-22R protein, wherein the D2 domain is amino acid residues 125 to 228 of SEQ ID NO: 71;
the antibody or antigen binding fragment may bind to human IL-22R with high affinity;
the antibody or antigen binding fragment may block binding of IL-22 to IL-22R;
the antibody or antigen binding fragment may inhibit IL-22-dependent activation of IL-22R;
the antibody or antigen binding fragment may inhibit IL-20-dependent activation of IL-22R;
the antibody or antigen binding fragment may inhibit IL-22-dependent activation of IL-22R and IL-20-dependent activation of IL-22R;
the antibody or antigen binding fragment may not cross-react with murine IL-22R.

The IL-22R antibodies or antigen binding fragments thereof provided herein preferably exhibit two or more of the following properties/features:
the antibody or antigen binding fragment binds to an epitope within human IL-22R protein that does not include Tyr60;
the antibody or antigen binding fragment binds to human IL-22R with high affinity;

the antibody or antigen binding fragment inhibits IL-22-dependent activation of IL-22R and IL-20-dependent activation of IL-22R.

The IL-22R antibodies, or antigen binding fragments thereof, provided herein may be chimeric antibodies. In certain embodiments, the antibodies or antigen binding fragments thereof contain the hinge region, CH2 domain and/or CH3 domain of a human IgG. In certain embodiments, the antibodies or antigen binding fragments thereof exhibit high homology to a human IgG, preferably a human IgG1, wherein "high human homology" is as defined elsewhere herein. In certain embodiments, the antibodies or antigen binding fragments thereof comprise a heavy chain variable domain (VH) and a light chain variable domain (VL) wherein the VH and/or VL domains or one or more complementarity determining regions (CDRs) thereof are derived from an animal of the Camelidae family i.e. are camelid-derived, preferably wherein the camelid is a llama.

In further aspects, the invention also provides polynucleotide molecules which encode the above-listed antibodies and antigen binding fragments, in addition to expression vectors comprising the polynucleotides, host cells containing the vectors and methods of recombinant expression/production of the antibodies described herein.

In a still further aspect, the invention provides a pharmaceutical composition comprising any one of the IL-22R antibodies or antigen binding fragments thereof described herein, and a pharmaceutically acceptable carrier or excipient.

A still further aspect of the invention concerns methods of medical treatment using the above-listed IL-22R antibodies or antigen binding fragments thereof, particularly in the prophylaxis and/or treatment of conditions such as psoriasis, psoriatic arthritis and atopic dermatitis.

These and other embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF DRAWINGS

FIG. 2 shows the full-length amino acid sequence of human IL-22R (SEQ ID NO: 71).

FIG. 3 shows the full-length nucleotide sequence encoding human IL-22R (SEQ ID NO: 72).

In FIG. 4A, the effect of IL-22R mAbs on proliferation of the BW-hIL-22R cell line is shown. BW-hIL-22R cells stably express the human IL-22R and growth is inhibited/arrested in response to the ligand IL-22. Antibodies capable of blocking the interaction between IL-22 and hIL-22R alleviate the growth inhibition mediated by ligand-receptor binding. In FIG. 4B, the effect of IL-22R mAbs on proliferation of the Baf3-hIL-22R/IL20Rb cell line is shown. Baf3-hIL-22R/IL20Rb cells stably express the components of the receptor complex IL-22R/IL20Rb such that the cells proliferate in the presence of IL-20. Antibodies capable of blocking the interaction between IL-20 and this receptor complex inhibit the proliferation induced by ligand binding.

FIGS. 5A-5B show the alignment of the IL-22R extracellular domain from various species. FIG. 5A shows the partial EST sequences available from Genbank; FIG. 5B shows the sequences determined after cloning of cynomolgus and rhesus IL-22R from the cynomolgus cDNA library.

In FIG. 7A, domains D1 and D2 of IL-22R contribute residues to the interface with the ligand IL-22. In FIG. 7B, Y60 in domain D1 is an important IL-22R residue contributing to the interaction with site 1A of the IL-22 ligand.

In FIG. 9A, the effect of IL-22R mAbs on proliferation of the BW-hIL-22R cell line is shown. BW-hIL-22R cells stably express the human IL-22R and growth is inhibited/arrested in response to the ligand IL-22. Antibodies capable of blocking the interaction between IL-22 and hIL-22R alleviate the growth inhibition mediated by ligand-receptor binding. In FIG. 9B, the effect of IL-22R mAbs on proliferation of the Baf3-hIL-22R/IL20Rb cell line is shown. Baf3-hIL-22R/IL20Rb cells stably express the components of the receptor complex IL-22R/IL20Rb such that the cells proliferate in the presence of IL-20. Antibodies capable of blocking the interaction between IL-20 and this receptor complex inhibit the proliferation induced by ligand binding.

FIGS. 13A-13B show pharmacokinetic data for IL-22R antibody 230C9 at various doses. At higher doses (10 mg/kg) when the capacity for target mediated drug disposition (TMDD) is saturated, the clearance values approach the non-specific clearance by RES. B. Clearance of 230C9-N297Q in cynomolgus. The total clearance represents the sum of 1) TMDD that is non-linear and saturable and 2) non-specific clearance that is linear and attributed to RES. Plasma half-life has an inverse relationship with clearance, leading to a long half-live at high doses and shorter half-life at lower doses due to target mediated clearance.

Figure 14A:
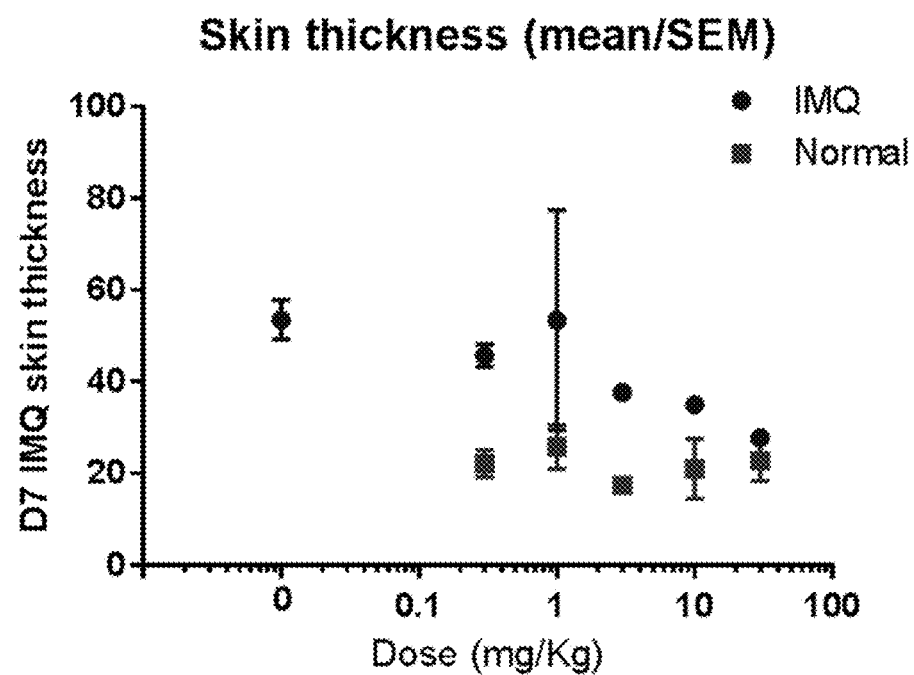
Figure 14B:
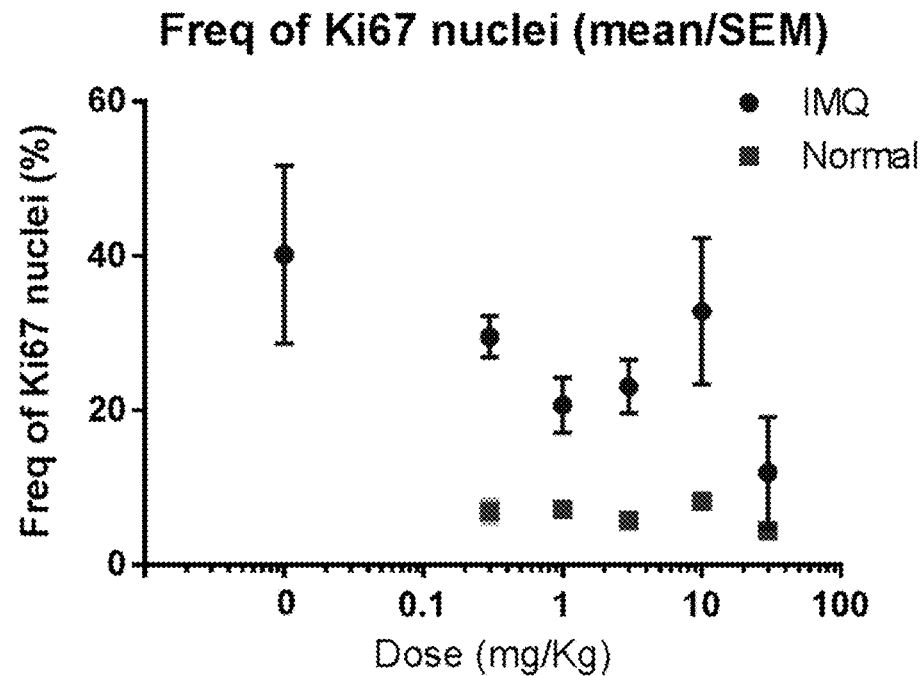

FIGS. 14A-14B show the pharmacodynamic effect of the IL-22R antibody 230C9. A cynomolgus monkey was exposed to 230C9 at different doses and the effects on an IMQ-treated skin section and a normal skin section of the monkey were assessed. Increasing doses of antibody 230C9 were found to normalize epidermal thickness (A) and reduce the frequency of Ki67 positive nuclei (B) in the IMQ-treated skin section.

Figure 15:
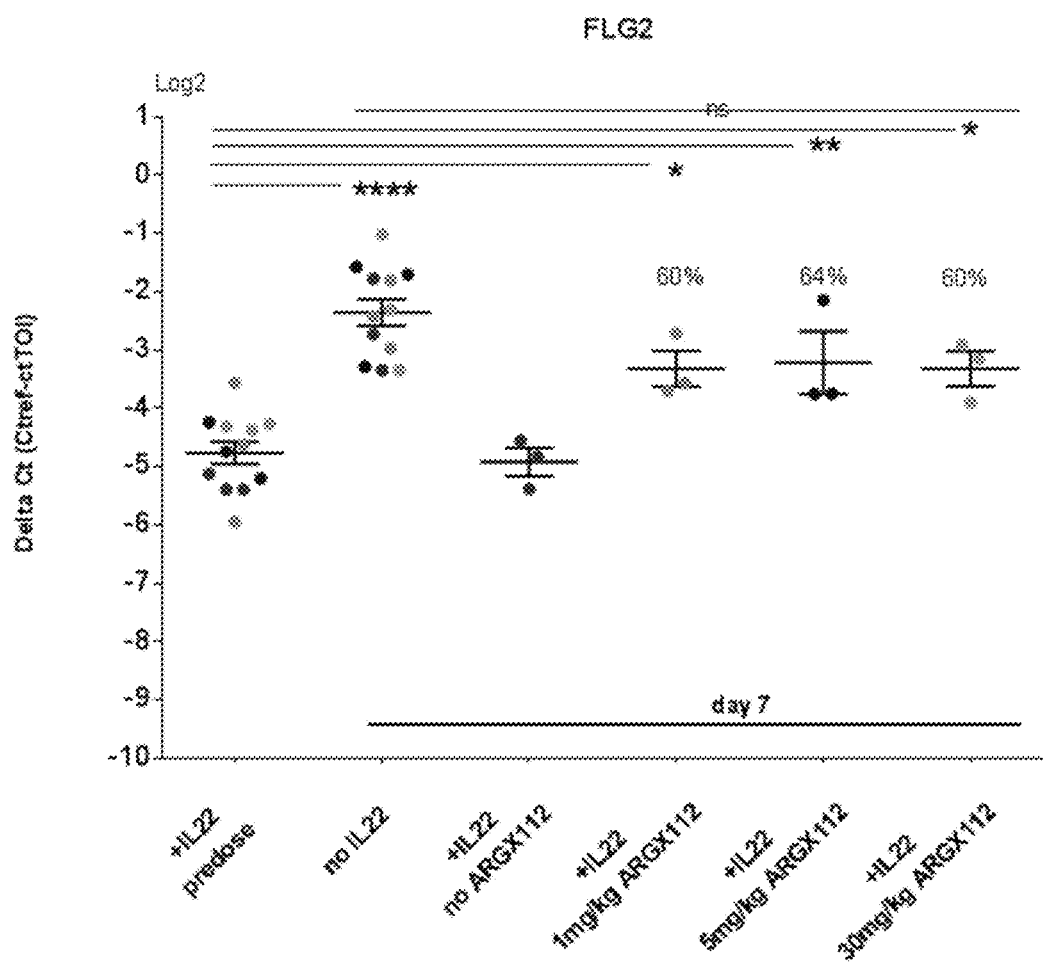

FIG. 15 shows the effect of the IL-22R antibody 230C9 (ARGX-112) on IL-22-regulated FLG2 mRNA levels in skin punch biopsies. Cynomolgus monkeys were administered single IV infusions of antibody 230C9 at different doses: 1 mg/kg, 5 mg/kg and 30 mg/kg (3 animals per dose). Recombinant human IL-22 reduced the total skin FLG2 mRNA levels whereas this effect was reversed by antibody 230C9. The y axis indicates relative FLG2 expression as compared with a reference gene. Statistical comparisons between groups are indicated by the lines at the top of the graph with confidence intervals as follows: *$p<0.05$; $p<0.01$; *$p<0.001$. The percentages shown (60%, 64%, 60%, respectively) indicate the % inhibition of the signal.

Figure 16:
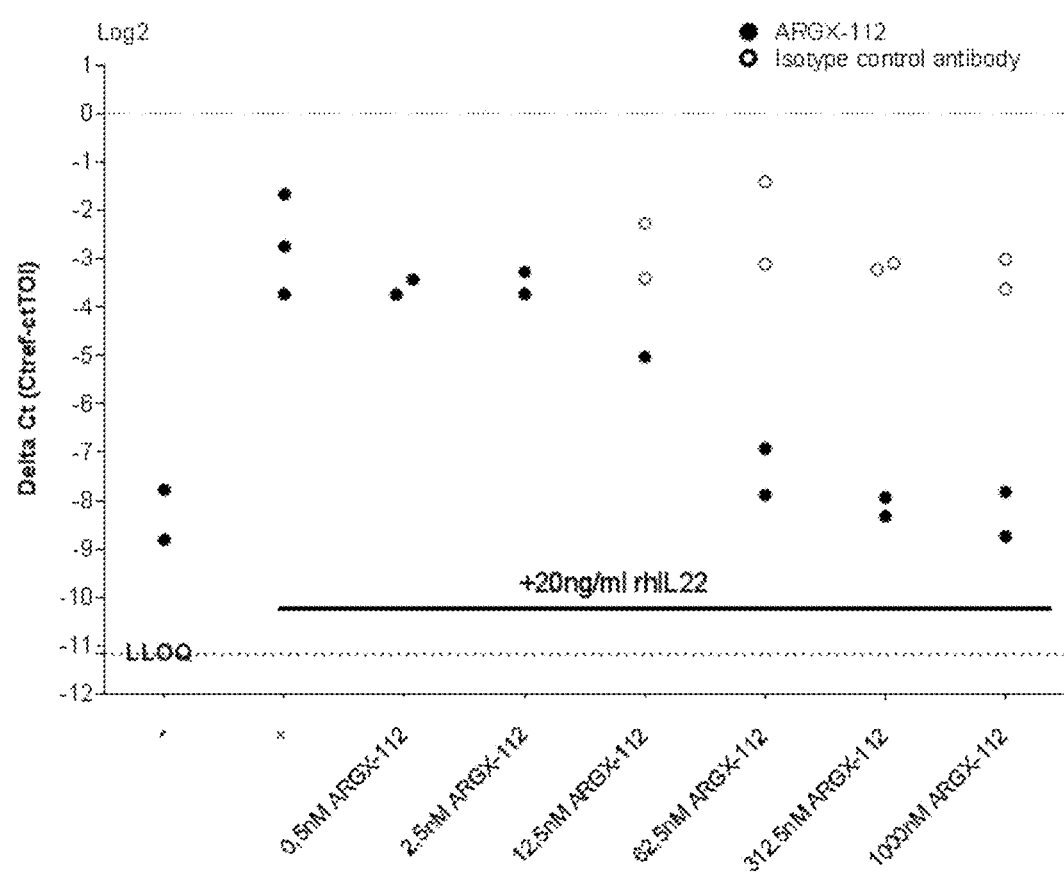

FIG. 16 shows the effect of the IL-22R antibody 230C9 (ARGX-112) on IL-22 regulated DEFB4 gene expression in human ex vivo skin explants. Abdominal skin explants were treated with increasing concentrations of antibody 230C9 prior to stimulation with 20 ng/ml rhIL-22. Antibody 230C9 was able to reverse the IL-22-mediated increase in DEFB4 mRNA levels in a dose-dependent manner. The y axis indicates relative DEFB4 expression as compared with a reference gene. LLOQ means lower level of quantification.

Figure 17A:
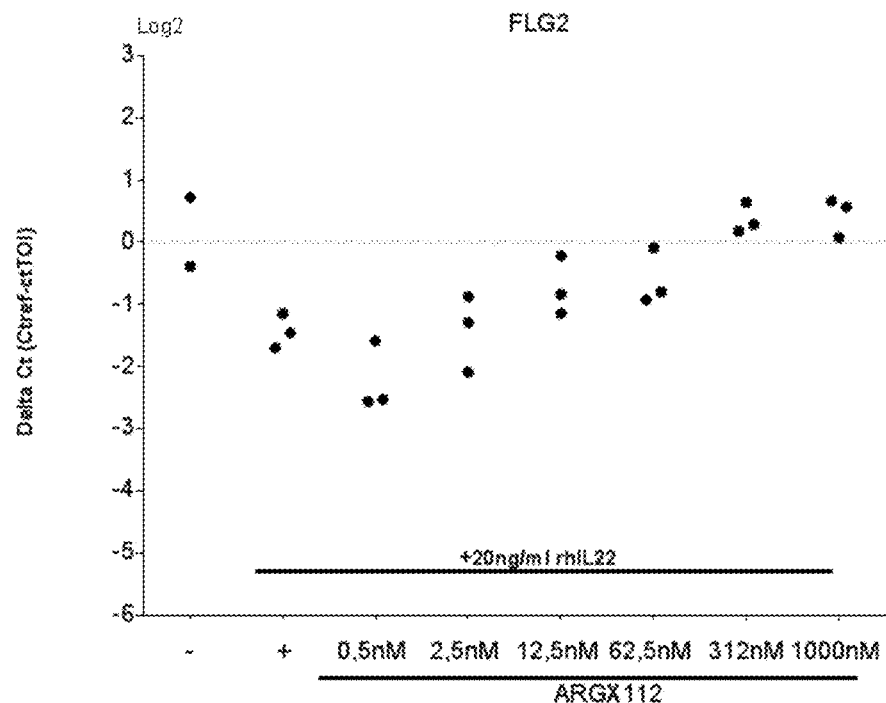
Figure 17B:
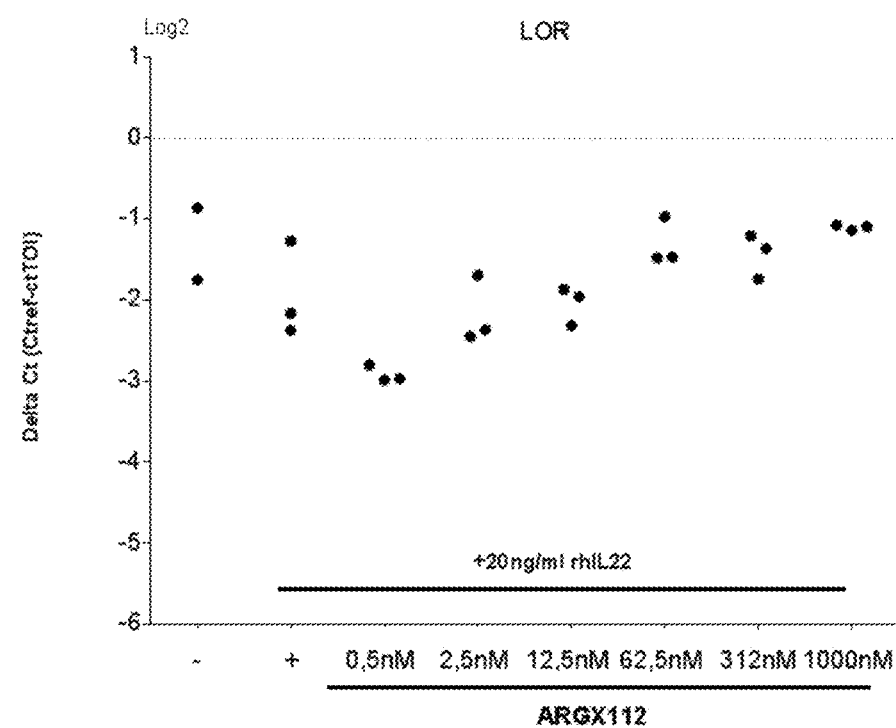

FIGS. 17A-17B show the effect of the IL-22R antibody 230C9 (ARGX-112) on IL-22 regulated FLG2 and LOR gene expression in cynomolgus monkey ex vivo skin explants. Skin biopsies were treated with increasing concentrations of antibody 230C9 prior to stimulation with 20 ng/ml rhIL-22. Antibody 230C9 was able to reverse the IL-22-mediated decrease in FLG2 mRNA levels (A) and LOR mRNA levels (B) in a dose-dependent manner. The y axes indicate relative FLG2 and LOR expression as compared with a reference gene.

Figure 18:
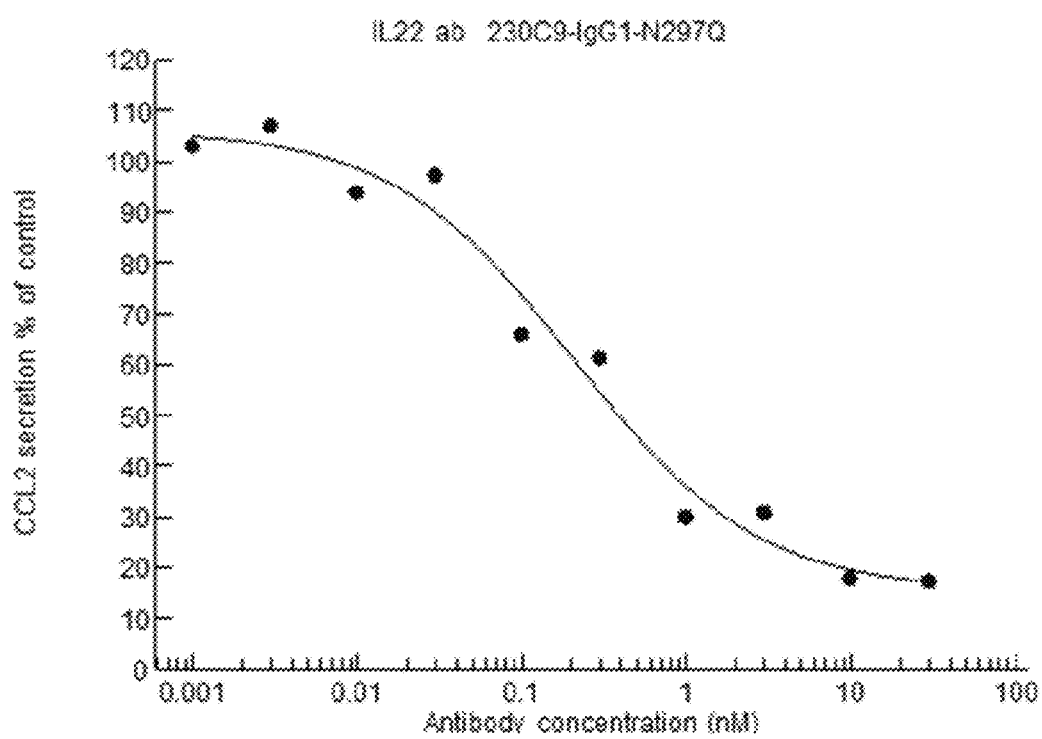

FIG. 18 shows the effect of the IL-22R antibody 230C9 (ARGX-112) on primary human keratinocytes. Keratinocytes were pre-treated with 230C9 antibody and then stimulated with a mixture of IL-4, IL-13, IL-22 and IFN-γ. Control cells were treated with a mixture of IL-4, IL-13 and IFN-γ. The 230C9 antibody showed dose-dependent inhibition of CCL2 secretion.

DETAILED DESCRIPTION

A. Definitions

"Antibody" or "Immunoglobulin"—As used herein, the term "immunoglobulin" includes a polypeptide having a combination of two heavy and two light chains whether or not it possesses any relevant specific immunoreactivity. "Antibodies" refer to such assemblies which have significant known specific immunoreactive activity to an antigen of interest (e.g. the cytokine receptor IL-22R). The term "IL-22R antibodies" is used herein to refer to antibodies which exhibit immunological specificity for IL-22R protein, including human IL-22R and in some cases species homologues thereof. Antibodies and immunoglobulins comprise light and heavy chains, with or without an interchain covalent linkage between them. Basic immunoglobulin structures in vertebrate systems are relatively well understood.

The generic term "immunoglobulin" comprises five distinct classes of antibody that can be distinguished biochemically. All five classes of antibodies are within the scope of the present invention. The following discussion will generally be directed to the IgG class of immunoglobulin molecules. With regard to IgG, immunoglobulins comprise two identical light polypeptide chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

The light chains of an antibody are classified as either kappa or lambda (κ,λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA, IgD or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernible to the skilled artisan in view of the instant disclosure and, accordingly, are within the scope of the instant invention.

As indicated above, the variable region of an antibody allows the antibody to selectively recognize and specifically bind epitopes on antigens. That is, the VL domain and VH domain of an antibody combine to form the variable region that defines a three dimensional antigen binding site. This quaternary antibody structure forms the antigen binding site present at the end of each arm of the Y. More specifically, the antigen binding site is defined by three complementary determining regions (CDRs) on each of the VH and VL chains.

"IL-22R"—As used herein, the term "IL-22R" means the type II cytokine receptor that mediates signalling via the ligands IL-22, IL-20 and IL-24. IL-22R is capable of forming heterodimeric complexes at the cell surface with IL-10R2 and IL-20R2. IL-22R may also be referred to as IL22R, IL-22R1, IL22R1, IL22RA, IL-22RA, CRF2-9 and Zcytor 11. The term "IL-22R1" is broad enough to cover the human form of the receptor and species homologues. The amino acid sequence of the full-length human IL-22R is represented by SEQ ID NO: 71 and the encoding nucleotide sequence is represented by SEQ ID NO: 72 (see FIGS. 2 and 3). These sequences correspond to the sequences deposited in the SwissProt database as human protein Interleukin-22 receptor subunit, accession number Q8N6P7.

"Binding Site"—As used herein, the term "binding site" comprises a region of a polypeptide which is responsible for selectively binding to a target antigen of interest (e.g. IL-22R). Binding domains comprise at least one binding site. Exemplary binding domains include an antibody variable domain. The antibody molecules of the invention may comprise a single binding site or multiple (e.g., two, three or four) binding sites.

"Derived From"—As used herein the term "derived from" a designated protein (e.g. a camelid antibody or antigen-binding fragment thereof) refers to the origin of the polypeptide or amino acid sequence. In one embodiment, the polypeptide or amino acid sequence which is derived from a particular starting polypeptide is a CDR sequence or sequence related thereto. In one embodiment, the amino acid sequence which is derived from a particular starting polypeptide is not contiguous. For example, in one embodiment, one, two, three, four, five, or six CDRs are derived from a starting antibody. In one embodiment, the polypeptide or amino acid sequence which is derived from a particular starting polypeptide or amino acid sequence has an amino acid sequence that is essentially identical to that of the starting sequence, or a portion thereof wherein the portion consists of at least 3-5 amino acids, at least 5-10 amino acids, at least 10-20 amino acids, at least 20-30 amino acids, or at least 30-50 amino acids, or which is otherwise identifiable to one of ordinary skill in the art as having its origin in the starting sequence. In one embodiment, the one or more CDR sequences derived from the starting antibody are altered to produce variant CDR sequences, e.g. affinity variants, wherein the variant CDR sequences maintain target antigen binding activity.

"Camelid-Derived"—In certain preferred embodiments, the antibodies of the invention comprise framework amino acid sequences and/or CDR amino acid sequences derived from a camelid conventional antibody raised by active immunisation of a camelid. However, antibodies of the invention comprising camelid-derived amino acid sequences may be engineered to comprise framework and/or constant region sequences derived from a human amino acid sequence (i.e. a human antibody) or other non-camelid mammalian species. For example, a human or non-human primate framework region, heavy chain portion, and/or hinge portion may be included in the subject IL-22R antibodies. In one embodiment, one or more non-camelid amino acids may be present in the framework region of a "camelid-derived" antibody, e.g., a camelid framework amino acid sequence may comprise one or more amino acid mutations in which the corresponding human or non-human primate amino acid residue is present. Moreover, camelid-derived VH and VL domains, or humanised variants thereof, may be linked to the constant domains of human antibodies to produce a chimeric molecule, as described elsewhere herein.

"Conservative amino acid substitution"—A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a non-essential amino acid residue in an immunoglobulin polypeptide may be replaced with another amino acid residue from the same side chain family. In another embodiment, a string of amino acids can be replaced with a structurally similar string that differs in order and/or composition of side chain family members.

"Heavy chain portion"—As used herein, the term "heavy chain portion" includes amino acid sequences derived from the constant domains of an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. In one embodiment, an antibody or antigen binding fragment of the invention may comprise the Fc portion of an immunoglobulin heavy chain (e.g., a hinge portion, a CH2 domain, and a CH3 domain). In another embodiment, an antibody or antigen binding fragment of the invention may lack at least a portion of a constant domain (e.g., all or part of a CH2 domain). In certain embodiments, at least one, and preferably all, of the constant domains are derived from a human immunoglobulin heavy chain. For example, in one preferred embodiment, the heavy chain portion comprises a fully human hinge domain. In other preferred embodiments, the heavy chain portion comprising a fully human Fc portion (e.g., hinge, CH2 and CH3 domain sequences from a human immunoglobulin).

In certain embodiments, the constituent constant domains of the heavy chain portion are from different immunoglobulin molecules. For example, a heavy chain portion of a polypeptide may comprise a CH2 domain derived from an IgG1 molecule and a hinge region derived from an IgG3 or IgG4 molecule. In other embodiments, the constant domains are chimeric domains comprising portions of different immunoglobulin molecules. For example, a hinge may comprise a first portion from an IgG1 molecule and a second portion from an IgG3 or IgG4 molecule. As set forth above, it will be understood by one of ordinary skill in the art that the constant domains of the heavy chain portion may be modified such that they vary in amino acid sequence from the naturally occurring (wild-type) immunoglobulin molecule. That is, the polypeptides of the invention disclosed herein may comprise alterations or modifications to one or more of the heavy chain constant domains (CH1, hinge, CH2 or CH3) and/or to the light chain constant region domain (CL). Exemplary modifications include additions, deletions or substitutions of one or more amino acids in one or more domains.

"Chimeric"—A "chimeric" protein comprises a first amino acid sequence linked to a second amino acid sequence with which it is not naturally linked in nature. The amino acid sequences may normally exist in separate proteins that are brought together in the fusion polypeptide or they may normally exist in the same protein but are placed in a new arrangement in the fusion polypeptide. A chimeric protein may be created, for example, by chemical synthesis, or by creating and translating a polynucleotide in which the peptide regions are encoded in the desired relationship. Exemplary chimeric antibodies of the invention include fusion proteins comprising camelid-derived VH and VL domains, or humanised variants thereof, fused to the constant domains of a human antibody, e.g. human IgG1, IgG2, IgG3 or IgG4.

"Variable region" or "variable domain"—The terms "variable region" and "variable domain" are used herein interchangeably and are intended to have equivalent meaning. The term "variable" refers to the fact that certain portions of the variable domains VH and VL differ extensively in sequence among antibodies and are used in the binding and specificity of each particular antibody for its target antigen. However, the variability is not evenly distributed throughout the variable domains of antibodies. It is concentrated in three segments called "hypervariable loops" in each of the VL domain and the VH domain which form part of the antigen binding site. The first, second and third hypervariable loops of the VLambda light chain domain are referred to herein as L1(λ), L2(λ) and L3(λ) and may be defined as comprising residues 24-33 (L1(λ), consisting of 9, 10 or 11 amino acid residues), 49-53 (L2(λ), consisting of 3 residues) and 90-96 (L3(λ), consisting of 5 residues) in the VL domain (Morea et al., Methods 20:267-279 (2000)). The first, second and third hypervariable loops of the VKappa light chain domain are referred to herein as L1(κ), L2(κ) and L3(κ) and may be defined as comprising residues 25-33 (L1(κ), consisting of 6, 7, 8, 11, 12 or 13 residues), 49-53 (L2(κ), consisting of 3 residues) and 90-97 (L3(κ), consisting of 6 residues) in the VL domain (Morea et al., Methods 20:267-279 (2000)). The first, second and third hypervariable loops of the VH domain are referred to herein as H1, H2 and H3 and may be defined as comprising residues 25-33 (H1, consisting of 7, 8 or 9 residues), 52-56 (H2, consisting of 3 or 4 residues) and 91-105 (H3, highly variable in length) in the VH domain (Morea et al., Methods 20:267-279 (2000)).

Unless otherwise indicated, the terms L1, L2 and L3 respectively refer to the first, second and third hypervariable loops of a VL domain, and encompass hypervariable loops obtained from both Vkappa and Vlambda isotypes. The terms H1, H2 and H3 respectively refer to the first, second and third hypervariable loops of the VH domain, and encompass hypervariable loops obtained from any of the known heavy chain isotypes, including γ, ε, δ, α or μ.

The hypervariable loops L1, L2, L3, H1, H2 and H3 may each comprise part of a "complementarity determining region" or "CDR", as defined below. The terms "hypervariable loop" and "complementarity determining region" are not strictly synonymous, since the hypervariable loops (HVs) are defined on the basis of structure, whereas complementarity determining regions (CDRs) are defined based on sequence variability (Kabat et al., Sequences of Proteins of Immunological Interest, 5th Ed. Public Health Service, National Institutes of Health, Bethesda, Md., 1983) and the limits of the HVs and the CDRs may be different in some VH and VL domains.

The CDRs of the VL and VH domains can typically be defined as comprising the following amino acids: residues 24-34 (LCDR1), 50-56 (LCDR2) and 89-97 (LCDR3) in the light chain variable domain, and residues 31-35 or 31-35b (HCDR1), 50-65 (HCDR2) and 95-102 (HCDR3) in the heavy chain variable domain; (Kabat et al., Sequences of Proteins of Immunological Interest, 5th Ed. Public Health Service, National Institutes of Health, Bethesda, Md. (1991)). Thus, the HVs may be comprised within the corresponding CDRs and references herein to the "hypervariable loops" of VH and VL domains should be interpreted as also encompassing the corresponding CDRs, and vice versa, unless otherwise indicated.

The more highly conserved portions of variable domains are called the framework region (FR), as defined below. The variable domains of native heavy and light chains each comprise four FRs (FR1, FR2, FR3 and FR4, respectively), largely adopting a β-sheet configuration, connected by the three hypervariable loops. The hypervariable loops in each chain are held together in close proximity by the FRs and, with the hypervariable loops from the other chain, contribute to the formation of the antigen-binding site of antibodies.

Structural analysis of antibodies revealed the relationship between the sequence and the shape of the binding site formed by the complementarity determining regions (Chothia et al., J. Mol. Biol. 227: 799-817 (1992)); Tramontano et al., J. Mol. Biol, 215:175-182 (1990)). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

"CDR"—As used herein, the term "CDR" or "complementarity determining region" means the non-contiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat based on sequence comparisons.

TABLE 1

CDR definitions

| | Kabat[1] | Chothia[2] | MacCallum[3] |
|---|---|---|---|
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra "Framework region"—The term "framework region" or "FR region" as used herein, includes the amino acid residues that are part of the variable region, but are not part of the CDRs (e.g., using the Kabat definition of CDRs). Therefore, a variable region framework is between about 100-120 amino acids in length but includes only those amino acids outside of the CDRs. For the specific example of a heavy chain variable domain and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light chain variable region CDRs. Similarly, using the definition of CDRs by Chothia et al. or McCallum et al. the framework region boundaries are separated by the respective CDR termini as described above. In preferred embodiments the CDRs are as defined by Kabat.

In naturally occurring antibodies, the six CDRs present on each monomeric antibody are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

"Hinge region"—As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux K. H. et al. J. Immunol. 161:4083-90 1998). Antibodies of the invention comprising a "fully human" hinge region may contain one of the hinge region sequences shown in Table 2 below.

polypeptide fragment of an immunoglobulin or antibody that binds antigen or competes with intact antibody (i.e., with the intact antibody from which they were derived) for antigen binding (i.e., specific binding to IL-22R). As used herein, the term "fragment" of an antibody molecule includes antigen-binding fragments of antibodies, for example, an antibody light chain variable domain (VL), an antibody heavy chain variable domain (VH), a single chain antibody (scFv), a F(ab')2 fragment, a Fab fragment, an Fd fragment, an Fv fragment, and a single domain antibody fragment (DAb). Fragments can be obtained, e.g., via chemical or enzymatic treatment of an intact or complete antibody or antibody chain or by recombinant means.

"Valency"—As used herein the term "valency" refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different ligands or different antigens, or different epitopes on the same antigen).

"Specificity"—The term "specificity" refers to the ability to bind (e.g., immunoreact with) a given target, e.g., IL-22R. A polypeptide may be monospecific and contain one or more binding sites which specifically bind a target or a polypeptide may be multispecific and contain two or more binding sites which specifically bind the same or different targets.

"Synthetic"—As used herein the term "synthetic" with respect to polypeptides includes polypeptides which comprise an amino acid sequence that is not naturally occurring.

TABLE 2

Human hinge sequences

| IgG | Upper hinge | Middle hinge | Lower hinge |
|---|---|---|---|
| IgG1 | EPKSCDKTHT (SEQ ID NO: 82) | CPPCP (SEQ ID NO: 83) | APELLGGP (SEQ ID NO: 84) |
| IgG3 | ELKTPLGDTTHT (SEQ ID NO: 85) | CPRCP (EPKSCDTPPPCPRCP)$_3$ (SEQ ID NO: 86) | APELLGGP (SEQ ID NO: 87) |
| IgG4 | ESKYGPP (SEQ ID NO: 88) | CPSCP (SEQ ID NO: 89) | APEFLGGP (SEQ ID NO: 90) |
| IgG42 | ERK (SEQ ID NO: 91) | CCVECPPPCP (SEQ ID NO: 92) | AP PVAG P (SEQ ID NO: 93) |

"CH2 domain"—As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system, Kabat E A et al. Sequences of Proteins of Immunological Interest. Bethesda, US Department of Health and Human Services, NIH. 1991). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

"Fragment"—The term "fragment", as used in the context of antibodies of the invention, refers to a part or portion of an antibody or antibody chain comprising fewer amino acid residues than an intact or complete antibody or antibody chain. The term "antigen-binding fragment" refers to a For example, non-naturally occurring polypeptides which are modified forms of naturally occurring polypeptides (e.g., comprising a mutation such as an addition, substitution or deletion) or which comprise a first amino acid sequence (which may or may not be naturally occurring) that is linked in a linear sequence of amino acids to a second amino acid sequence (which may or may not be naturally occurring) to which it is not naturally linked in nature.

"Engineered"—As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques). Preferably, the antibodies of the invention are engineered, including for example, humanized and/or chimeric antibodies, and antibodies which have been engineered to improve one or more properties, such as antigen binding, stability/half-life or effector function.

"Modified antibody"—As used herein, the term "modified antibody" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules and the like. scFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen). In another embodiment, a modified antibody of the invention is a fusion protein comprising at least one heavy chain portion lacking a CH2 domain and comprising a binding domain of a polypeptide comprising the binding portion of one member of a receptor ligand pair.

The term "modified antibody" may also be used herein to refer to amino acid sequence variants of the antibodies of the invention as structurally defined herein. It will be understood by one of ordinary skill in the art that an antibody may be modified to produce a variant antibody which varies in amino acid sequence in comparison to the antibody from which it was derived. For example, nucleotide or amino acid substitutions leading to conservative substitutions or changes at "non-essential" amino acid residues may be made (e.g., in CDR and/or framework residues). Amino acid substitutions can include replacement of one or more amino acids with a naturally occurring or non-natural amino acid.

"Humanising substitutions"—As used herein, the term "humanising substitutions" refers to amino acid substitutions in which the amino acid residue present at a particular position in the VH or VL domain of an antibody (for example a camelid-derived IL-22R antibody) is replaced with an amino acid residue which occurs at an equivalent position in a reference human VH or VL domain. The reference human VH or VL domain may be a VH or VL domain encoded by the human germline. Humanising substitutions may be made in the framework regions and/or the CDRs of the antibodies, defined herein.

"Humanised variants"—As used herein the term "humanised variant" refers to a variant antibody which contains one or more "humanising substitutions" compared to a reference antibody, wherein a portion of the reference antibody (e.g. the VH domain and/or the VL domain or parts thereof containing at least one CDR) has an amino acid derived from a non-human species, and the "humanising substitutions" occur within the amino acid sequence derived from a non-human species.

"Germlined variants"—The term "germlined variant" is used herein to refer specifically to "humanised variants" in which the "humanising substitutions" result in replacement of one or more amino acid residues present at a particular position (s) in the VH or VL domain of an antibody (for example a camelid-derived IL-22R antibody) with an amino acid residue which occurs at an equivalent position in a reference human VH or VL domain encoded by the human germline. It is typical that for any given "germlined variant", the replacement amino acid residues substituted into the germlined variant are taken exclusively, or predominantly, from a single human germline-encoded VH or VL domain. The terms "humanised variant" and "germlined variant" are often used interchangeably herein. Introduction of one or more "humanising substitutions" into a camelid-derived (e.g. llama derived) VH or VL domain results in production of a "humanised variant" of the camelid (llama)-derived VH or VL domain. If the amino acid residues substituted in are derived predominantly or exclusively from a single human germline-encoded VH or VL domain sequence, then the result may be a "human germlined variant" of the camelid (llama)-derived VH or VL domain.

"Affinity variants"—As used herein, the term "affinity variant" refers to a variant antibody which exhibits one or more changes in amino acid sequence compared to a reference antibody, wherein the affinity variant exhibits an altered affinity for the target antigen in comparison to the reference antibody. For example, affinity variants will exhibit a changed affinity for IL-22R, as compared to the reference IL-22R antibody. Preferably the affinity variant will exhibit improved affinity for the target antigen, e.g. IL-22R, as compared to the reference antibody. Affinity variants typically exhibit one or more changes in amino acid sequence in the CDRs, as compared to the reference antibody. Such substitutions may result in replacement of the original amino acid present at a given position in the CDRs with a different amino acid residue, which may be a naturally occurring amino acid residue or a non-naturally occurring amino acid residue. The amino acid substitutions may be conservative or non-conservative.

"High human homology"—An antibody comprising a heavy chain variable domain (VH) and a light chain variable domain (VL) will be considered as having high human homology if the VH domains and the VL domains, taken together, exhibit at least 90% amino acid sequence identity to the closest matching human germline VH and VL sequences. Antibodies having high human homology may include antibodies comprising VH and VL domains of native non-human antibodies which exhibit sufficiently high % sequence identity to human germline sequences, including for example antibodies comprising VH and VL domains of camelid conventional antibodies, as well as engineered, especially humanised or germlined, variants of such antibodies and also "fully human" antibodies.

In one embodiment the VH domain of the antibody with high human homology may exhibit an amino acid sequence identity or sequence homology of 80% or greater with one or more human VH domains across the framework regions FR1, FR2, FR3 and FR4. In other embodiments the amino acid sequence identity or sequence homology between the VH domain of the polypeptide of the invention and the closest matching human germline VH domain sequence may be 85% or greater, 90% or greater, 95% or greater, 97% or greater, or up to 99% or even 100%.

In one embodiment the VH domain of the antibody with high human homology may contain one or more (e.g. 1 to 10) amino acid sequence mis-matches across the framework regions FR1, FR2, FR3 and FR4, in comparison to the closest matched human VH sequence.

In another embodiment the VL domain of the antibody with high human homology may exhibit a sequence identity or sequence homology of 80% or greater with one or more human VL domains across the framework regions FR1, FR2, FR3 and FR4. In other embodiments the amino acid sequence identity or sequence homology between the VL domain of the polypeptide of the invention and the closest matching human germline VL domain sequence may be 85% or greater 90% or greater, 95% or greater, 97% or greater, or up to 99% or even 100%.

In one embodiment the VL domain of the antibody with high human homology may contain one or more (e.g. 1 to 10) amino acid sequence mis-matches across the framework regions FR1, FR2, FR3 and FR4, in comparison to the closest matched human VL sequence.

Before analyzing the percentage sequence identity between the antibody with high human homology and human germline VH and VL, the canonical folds may be determined, which allows the identification of the family of human germline segments with the identical combination of canonical folds for H1 and H2 or L1 and L2 (and L3). Subsequently the human germline family member that has the highest degree of sequence homology with the variable region of the antibody of interest is chosen for scoring the sequence homology. The determination of Chothia canonical classes of hypervariable loops L1, L2, L3, H1 and H2 can be performed with the bioinformatics tools publicly available on webpage www.bioinf.org.uk/abs/chothia.html.page. The output of the program shows the key residue requirements in a datafile. In these datafiles, the key residue positions are shown with the allowed amino acids at each position. The sequence of the variable region of the antibody of interest is given as input and is first aligned with a consensus antibody sequence to assign the Kabat numbering scheme. The analysis of the canonical folds uses a set of key residue templates derived by an automated method developed by Martin and Thornton (Martin et al., J. Mol. Biol. 263:800-815 (1996)).

With the particular human germline V segment known, which uses the same combination of canonical folds for H1 and H2 or L1 and L2 (and L3), the best matching family member in terms of sequence homology can be determined. With bioinformatics tools the percentage sequence identity between the VH and VL domain framework amino acid sequences of the antibody of interest and corresponding sequences encoded by the human germline can be determined, but actually manual alignment of the sequences can be applied as well. Human immunoglobulin sequences can be identified from several protein data bases, such as VBase (http://vbase.mrc-cpe.cam.ac.uk/) or the Pluckthun/Honegger database (http://www.bioc.unizh.ch/antibody/Sequences/Germlines. To compare the human sequences to the V regions of VH or VL domains in an antibody of interest a sequence alignment algorithm such as available via websites like www.expasy.ch/tools/#align can be used, but also manual alignment with the limited set of sequences can be performed. Human germline light and heavy chain sequences of the families with the same combinations of canonical folds and with the highest degree of homology with the framework regions 1, 2, and 3 of each chain are selected and compared with the variable region of interest; also the FR4 is checked against the human germline JH and JK or JL regions.

Note that in the calculation of overall percent sequence homology the residues of FR1, FR2 and FR3 are evaluated using the closest match sequence from the human germline family with the identical combination of canonical folds. Only residues different from the closest match or other members of the same family with the same combination of canonical folds are scored (NB—excluding any primer-encoded differences). However, for the purposes of humanization, residues in framework regions identical to members of other human germline families, which do not have the same combination of canonical folds, can be considered "human", despite the fact that these are scored "negative" according to the stringent conditions described above. This assumption is based on the "mix and match" approach for humanization, in which each of FR1, FR2, FR3 and FR4 is separately compared to its closest matching human germline sequence and the humanized molecule therefore contains a combination of different FRs as was done by Qu and colleagues (Qu et la., Clin. Cancer Res. 5:3095-3100 (1999)) and Ono and colleagues (Ono et al., Mol. Immunol. 36:387-395 (1999)). The boundaries of the individual framework regions may be assigned using the IMGT numbering scheme, which is an adaptation of the numbering scheme of Chothia (Lefranc et al., NAR 27: 209-212 (1999); imgt.cines.fr).

Antibodies with high human homology may comprise hypervariable loops or CDRs having human or human-like canonical folds, as discussed in detail below.

In one embodiment at least one hypervariable loop or CDR in either the VH domain or the VL domain of the antibody with high human homology may be obtained or derived from a VH or VL domain of a non-human antibody, for example a conventional antibody from a species of Camelidae, yet exhibit a predicted or actual canonical fold structure which is substantially identical to a canonical fold structure which occurs in human antibodies.

It is well established in the art that although the primary amino acid sequences of hypervariable loops present in both VH domains and VL domains encoded by the human germline are, by definition, highly variable, all hypervariable loops, except CDR H3 of the VH domain, adopt only a few distinct structural conformations, termed canonical folds (Chothia et al., J. Mol. Biol. 196:901-917 (1987); Tramontano et al. Proteins 6:382-94 (1989)), which depend on both the length of the hypervariable loop and presence of the so-called canonical amino acid residues (Chothia et al., J. Mol. Biol. 196:901-917 (1987)). Actual canonical structures of the hypervariable loops in intact VH or VL domains can be determined by structural analysis (e.g. X-ray crystallography), but it is also possible to predict canonical structure on the basis of key amino acid residues which are characteristic of a particular structure (discussed further below). In essence, the specific pattern of residues that determines each canonical structure forms a "signature" which enables the canonical structure to be recognised in hypervariable loops of a VH or VL domain of unknown structure; canonical structures can therefore be predicted on the basis of primary amino acid sequence alone.

The predicted canonical fold structures for the hypervariable loops of any given VH or VL sequence in an antibody with high human homology can be analysed using algorithms which are publicly available from www.bioinf.org.uk/abs/chothia.html, www.biochem.ucl.ac.uk/~martin/antibodies.html and www.bioc.unizh.ch/antibody/Sequences/Germlines/Vbase_hVk.html. These tools permit query VH or VL sequences to be aligned against human VH or VL domain sequences of known canonical structure, and a prediction of canonical structure made for the hypervariable loops of the query sequence.

In the case of the VH domain, H1 and H2 loops may be scored as having a canonical fold structure "substantially identical" to a canonical fold structure known to occur in human antibodies if at least the first, and preferably both, of the following criteria are fulfilled:

1. An identical length, determined by the number of residues, to the closest matching human canonical structural class.

2. At least 33% identity, preferably at least 50% identity with the key amino acid residues described for the corresponding human H1 and H2 canonical structural classes.

(note for the purposes of the foregoing analysis the H1 and H2 loops are treated separately and each compared against its closest matching human canonical structural class).

The foregoing analysis relies on prediction of the canonical structure of the H1 and H2 loops of the antibody of interest. If the actual structures of the H1 and H2 loops in the antibody of interest are known, for example based on X-ray crystallography, then the H1 and H2 loops in the antibody of interest may also be scored as having a canonical fold structure "substantially identical" to a canonical fold structure known to occur in human antibodies if the length of the loop differs from that of the closest matching human canonical structural class (typically by ±1 or ±2 amino acids) but the actual structure of the H1 and H2 loops in the antibody of interest matches the structure of a human canonical fold.

Key amino acid residues found in the human canonical structural classes for the first and second hypervariable loops of human VH domains (H1 and H2) are described by Chothia et al., J. Mol. Biol. 227:799-817 (1992), the contents of which are incorporated herein in their entirety by reference. In particular, Table 3 on page 802 of Chothia et al., which is specifically incorporated herein by reference, lists preferred amino acid residues at key sites for H1 canonical structures found in the human germline, whereas Table 4 on page 803, also specifically incorporated by reference, lists preferred amino acid residues at key sites for CDR H2 canonical structures found in the human germline.

In one embodiment, both H1 and H2 in the VH domain of the antibody with high human homology exhibit a predicted or actual canonical fold structure which is substantially identical to a canonical fold structure which occurs in human antibodies.

Antibodies with high human homology may comprise a VH domain in which the hypervariable loops H1 and H2 form a combination of canonical fold structures which is identical to a combination of canonical structures known to occur in at least one human germline VH domain. It has been observed that only certain combinations of canonical fold structures at H1 and H2 actually occur in VH domains encoded by the human germline. In an embodiment H1 and H2 in the VH domain of the antibody with high human homology may be obtained from a VH domain of a non-human species, e.g. a Camelidae species, yet form a combination of predicted or actual canonical fold structures which is identical to a combination of canonical fold structures known to occur in a human germline or somatically mutated VH domain. In non-limiting embodiments H1 and H2 in the VH domain of the antibody with high human homology may be obtained from a VH domain of a non-human species, e.g. a Camelidae species, and form one of the following canonical fold combinations: 1-1, 1-2, 1-3, 1-6, 1-4, 2-1, 3-1 and 3-5.

An antibody with high human homology may contain a VH domain which exhibits both high sequence identity/sequence homology with human VH, and which contains hypervariable loops exhibiting structural homology with human VH.

It may be advantageous for the canonical folds present at H1 and H2 in the VH domain of the antibody with high human homology, and the combination thereof, to be "correct" for the human VH germline sequence which represents the closest match with the VH domain of the antibody with high human homology in terms of overall primary amino acid sequence identity. By way of example, if the closest sequence match is with a human germline VH3 domain, then it may be advantageous for H1 and H2 to form a combination of canonical folds which also occurs naturally in a human VH3 domain. This may be particularly important in the case of antibodies with high human homology which are derived from non-human species, e.g. antibodies containing VH and VL domains which are derived from camelid conventional antibodies, especially antibodies containing humanised camelid VH and VL domains.

Thus, in one embodiment the VH domain of an IL-22R antibody with high human homology may exhibit a sequence identity or sequence homology of 80% or greater, 85% or greater, 90% or greater, 95% or greater, 97% or greater, or up to 99% or even 100% with a human VH domain across the framework regions FR1, FR2, FR3 and FR4, and in addition H1 and H2 in the same antibody are obtained from a non-human VH domain (e.g. derived from a Camelidae species), but form a combination of predicted or actual canonical fold structures which is the same as a canonical fold combination known to occur naturally in the same human VH domain.

In other embodiments, L1 and L2 in the VL domain of the antibody with high human homology are each obtained from a VL domain of a non-human species (e.g. a camelid-derived VL domain), and each exhibits a predicted or actual canonical fold structure which is substantially identical to a canonical fold structure which occurs in human antibodies.

As with the VH domains, the hypervariable loops of VL domains of both VLambda and VKappa types can adopt a limited number of conformations or canonical structures, determined in part by length and also by the presence of key amino acid residues at certain canonical positions.

Within an antibody of interest having high human homology, L1, L2 and L3 loops obtained from a VL domain of a non-human species, e.g. a Camelidae species, may be scored as having a canonical fold structure "substantially identical" to a canonical fold structure known to occur in human antibodies if at least the first, and preferable both, of the following criteria are fulfilled:

1. An identical length, determined by the number of residues, to the closest matching human structural class.
2. At least 33% identity, preferably at least 50% identity with the key amino acid residues described for the corresponding human L1 or L2 canonical structural classes, from either the VLambda or the VKappa repertoire.

(Note for the purposes of the foregoing analysis the L1 and L2 loops are treated separately and each compared against its closest matching human canonical structural class.)

The foregoing analysis relies on prediction of the canonical structure of the L1, L2 and L3 loops in the VL domain of the antibody of interest. If the actual structure of the L1, L2 and L3 loops is known, for example based on X-ray crystallography, then L1, L2 or L3 loops derived from the antibody of interest may also be scored as having a canonical fold structure "substantially identical" to a canonical fold structure known to occur in human antibodies if the length of the loop differs from that of the closest matching human canonical structural class (typically by ±1 or ±2 amino acids) but the actual structure of the Camelidae loops matches a human canonical fold.

Key amino acid residues found in the human canonical structural classes for the CDRs of human VLambda and VKappa domains are described by Morea et al. Methods, 20: 267-279 (2000) and Martin et al., J. Mol. Biol., 263:800-815 (1996). The structural repertoire of the human VKappa domain is also described by Tomlinson et al. EMBO J. 14:4628-4638 (1995), and that of the VLambda domain by Williams et al. J. Mol. Biol., 264:220-232 (1996). The contents of all these documents are to be incorporated herein by reference.

L1 and L2 in the VL domain of an antibody with high human homology may form a combination of predicted or actual canonical fold structures, which is identical to a combination of canonical fold structures known to occur in a human germline VL domain. In non-limiting embodiments L1 and L2 in the VLambda domain of an antibody with high human homology (e.g. an antibody containing a camelid-derived VL domain or a humanised variant thereof) may form one of the following canonical fold combinations: 11-7, 13-7(A,B,C), 14-7(A,B), 12-11, 14-11 and 12-12 (as defined in Williams et al. J. Mol. Biol. 264:220-32 (1996) and as shown on http://www.bioc.uzh.ch/antibody/Sequences/Germlines/VBase_hVL.html). In non-limiting embodiments L1 and L2 in the Vkappa domain may form one of the following canonical fold combinations: 2-1, 3-1, 4-1 and 6-1 (as defined in Tomlinson et al. EMBO J. 14:4628-38 (1995) and as shown on http://www.bioc.uzh.ch/antibody/Sequences/Germlines/VBase_hVK.html).

In a further embodiment, all three of L1, L2 and L3 in the VL domain of an antibody with high human homology may exhibit a substantially human structure. It is preferred that the VL domain of the antibody with high human homology exhibits both high sequence identity/sequence homology with human VL, and also that the hypervariable loops in the VL domain exhibit structural homology with human VL.

In one embodiment, the VL domain of a IL-22R antibody with high human homology may exhibit a sequence identity of 80% or greater, 85% or greater, 90% or greater, 95% or greater, 97% or greater, or up to 99% or even 100% vs to a human VL domain across the framework regions FR1, FR2, FR3 and FR4, and in addition hypervariable loop L1 and hypervariable loop L2 may form a combination of predicted or actual canonical fold structures which is the same as a canonical fold combination known to occur naturally in the same human VL domain.

It is, of course, envisaged that VH domains exhibiting high sequence identity/sequence homology with human VH, and also structural homology with hypervariable loops of human VH will be combined with VL domains exhibiting high sequence identity/sequence homology with human VL, and also structural homology with hypervariable loops of human VL to provide antibodies with high human homology containing VH/VL pairings (e.g camelid-derived VH/VL pairings) with maximal sequence and structural homology to human-encoded VH/VL pairings.

"scFv" or "scFv fragment"—An scFv or scFv fragment means a single chain variable fragment. An scFv is a fusion protein of a VH domain and a VL domain of an antibody connected via a linker.

B. IL-22R Antibodies

The present invention relates to antibodies and antigen binding fragments thereof that specifically bind to human IL-22R. The IL-22R antibodies and antibody fragments described herein possess properties, particularly combinations of properties, which are distinct and in certain cases superior, to the IL-22R antibodies of the prior art. These properties and characteristics will now be described in further detail.

IL-22R Epitopes

The IL-22R antibodies and antigen binding fragments of the present invention bind to an epitope within the human IL-22R protein that does not include amino acid residue tyrosine 60 (Tyr60 or Y60), wherein this amino acid position is defined with reference to the sequence of IL-22R shown in FIG. 2 (SEQ ID NO: 71). This surface-exposed residue of IL-22R has previously been identified as critical to ligand binding, and as reported herein (see in particular Example 8) prior art IL-22R antibody 280.346.TSY (as described in WO2011/061119) binds to an epitope including this residue. The IL-22R antibodies and antigen binding fragments of the present invention surprisingly bind to an epitope that does not include this critical residue, and yet in certain embodiments, are capable of blocking IL-22 binding and/or inhibiting IL-22 and/or IL-20 mediated signaling via IL-22R.

The binding interface between the extracellular domain of IL-22R and its ligand IL-22 is characterised in Jones et al. (Structure 16(9): 1333-1344 (2008)), the contents of which are incorporated herein in their entirety. The extracellular domain of IL-22R consists of five loops (L2-L6), certain residues of which are critical for mediating interactions with surface-exposed residues on the IL-22 ligand. Tyrosine 60 is located within the L2 loop formed by residues in the D1 domain of the IL-22R protein. In the IL-22/soluble IL-22R complex, residue Tyr60 inserts into a small cavity on IL-22 created within site 1a of the ligand. More specifically, this cavity is created at the intersection of helix F and the AB loop, two distinct secondary structures found in the IL-22 ligand. Helix F residues Lys162 and Glu166 on the ligand form hydrogen bonds to the OH of Tyr60 of the IL-22R and thus Tyr60 is a key residue mediating the interaction between site 1a on the ligand and domain D1 of the receptor.

The antibodies and antigen binding fragments described herein bind to an epitope that does not include Tyr60. As noted above, Tyr60 is located within the L2 loop in the D1 domain of the receptor. In certain embodiments, the epitope to which the IL-22R antibodies or antigen binding fragments bind is located at least in part in the D2 domain of the IL-22R i.e. between residues 125 and 228 of SEQ ID NO: 71. In certain embodiments, the epitope to which the IL-22R antibodies or antigen binding fragments bind comprises at least one, at least two, at least three amino acid residues located within the D2 domain of the IL-22R protein.

The inventors believe that the fact that the antibodies and antigen binding fragments of the present invention bind to an epitope which does not include Tyr60 is relevant to their mode of action. The antibodies and antigen binding fragments thereof are believed to interact with the D2 domain of IL22R, in lieu of or in addition to interacting with the D1 domain. The D2 domain of IL-22R is known to be involved in the interaction with the co-receptor. Without wishing to be bound by theory, the inventors believe that the antibody molecules of the present invention may have a dual mode of action, preventing binding to the ligand and preventing interaction with the co-receptor.

The epitope to which the antibodies or antigen binding fragments of the invention bind may be a linear epitope (i.e. an epitope consisting of a linear sequence of amino acids within the target antigen) or a conformational epitope (i.e. an epitope consisting of amino acids that are not necessarily contiguous in the target antigen).

Binding Affinity

In certain embodiments, antibodies and antigen binding fragments of the invention bind to human IL-22R with high affinity.

As used herein, the term "affinity" or "binding affinity" should be understood based on the usual meaning in the art in the context of antibody binding, and reflects the strength and/or stability of binding between an antigen and a binding site on an antibody or antigen binding fragment thereof.

The binding affinity of an antibody or antigen binding fragment thereof for its respective antigen can be determined experimentally using techniques known in the art. For example, BIACORE instruments measure affinity based on the immobilization of a target protein or antigen on a biosensor chip while the antibody or antibody fragment is passed over the immobilized target under specific flow conditions. These experiments yield $k_{on}$ and $k_{off}$ measurements, which can be translated into $K_D$ values, wherein $K_D$ is the equilibrium constant for the dissociation of an antigen with an antibody or fragment thereof. The smaller the $K_D$ value, the stronger the binding interaction between an antibody and its target antigen. As noted above, the affinity of an antibody may be determined by Biacore, for example using the protocol described elsewhere herein (see Example 6). The affinity of the antibody or antigen binding fragment for human IL-22R, as measured by Biacore, may be determined using a recombinant full-length IL-22R construct, as described for example, in Examples 3 and 6.

The IL-22R antibodies or antigen binding fragments thereof of the invention may exhibit an off-rate ($k_{off}$) for IL-22R of less than $2 \times 10^{-3}$ s$^{-1}$, less than $1.5 \times 10^{-3}$ s$^{-1}$, less than $1.2 \times 10^{-3}$ s$^{-1}$ when tested as a mAb, for example when the affinity of a heavy chain variable domain paired with a light chain variable domain is tested in the context of an IgG1 molecule. In preferred embodiments, the IL-22R antibodies or antigen binding fragments thereof of the invention exhibit an off-rate ($k_{off}$) for IL-22R of less than $2.5 \times 10^{-4}$ s$^{-1}$, preferably less than $1.5 \times 10^{-4}$ s$^{-1}$, more preferably less than $1 \times 10^{-4}$ s$^{-1}$ when tested as a mAb, for example when the affinity of a heavy chain variable domain paired with a light chain variable domain is tested in the context of an IgG1 molecule.

The IL-22R antibodies or antigen binding fragments thereof of the invention may exhibit an off-rate ($k_{off}$) for IL-22R in the range from $1 \times 10^{-6}$ s$^{-1}$ to $2 \times 10^{-3}$ s$^{-1}$, preferably in the range from $1 \times 10^{-6}$ s$^{-1}$ to $2.5 \times 10^{-4}$ s$^{-1}$, more preferably in the range from $1 \times 10^{-5}$ s$^{-1}$ to $1 \times 10^{-4}$ s$^{-1}$.

The IL-22R antibodies or antigen binding fragments thereof of the invention may exhibit a $K_D$ value less than $3 \times 10^{-9}$ M, less than $2.5 \times 10^{-9}$ M, less than $1 \times 10^{-9}$ M. In preferred embodiments, the IL-22R antibodies or antigen binding fragments thereof of the invention exhibit a $K_D$ value less than $5 \times 10^{-19}$ M, preferably less than $2 \times 10^{-19}$ M, preferably less than $1.5 \times 10^{-19}$ M.

Inhibition of IL-22 and IL-20 Binding and Downstream Signalling

In certain embodiments, antibodies and antigen binding fragments of the invention bind to human IL-22R and inhibit ligand binding to this receptor. This is particularly surprising given that the antibodies described herein bind to an epitope that does not include Tyr60. As described above, Tyr60 has been identified as a residue critical for ligand binding and therefore the IL-22R antibodies and antigen binding fragments of the present invention are surprising in their ability to inhibit ligand binding and in certain embodiments, inhibit signalling downstream of IL-22R.

The antibodies and antigen binding fragments may bind human IL-22R and inhibit IL-22 binding or inhibit IL-20 binding. Preferably, the antibodies and antigen binding fragments described herein inhibit IL-22 and IL-20 binding to the IL-22R.

Ligand binding to IL-22R on cells which express either the co-receptor IL-10R2 or IL-20R2 induces a conformational change in the receptor complex such that signalling pathways downstream of the receptor are activated. The antibodies or antigen binding fragments thereof as described herein may inhibit IL-22-dependent activation of IL-22R or may inhibit IL-20-dependent activation of IL-22R. As used herein, the term "IL-22-dependent activation of IL-22R" should be taken to mean the chain of signalling events that occur downstream of the IL-22R receptor complex upon binding of the ligand IL-22 to the IL-22R/IL-10R2 complex.

As used herein the term "IL-20-dependent activation of IL-22R" should be taken to mean the chain of signalling events that occur downstream of the IL-22R upon binding of the ligand IL-20 to the IL-22R/IL-20R2 complex.

IL-22-dependent activation of IL-22R can be measured in cells or cell lines expressing both the IL-22R and the co-receptor IL-10R2, for example the BW-hIL-22R cell line described in Dumoutier et al. J Biol Chem. 2009 Sep. 25; 284(39): 26377-84, the contents of which are incorporated herein in their entirety. IL-22 induces growth arrest in the BW-hIL-22R cell line and therefore IL-22 dependent activation of IL-22R can be determined in this cell line by measuring the proliferation of BW-hIL-22R cells, for example as described in Example 6. In certain embodiments, the antibodies or antigen binding fragments described herein exhibit an IC$_{50}$ (concentration at which 50% inhibition of activation is achieved) in an IL-22 dependent cell-based proliferation assay of less than 650 pM, preferably less than 600 pM. The cell-based proliferation assay is preferably an assay involving the BW-hIL-22R cell line as described herein.

IL-20-dependent activation of IL-22R can be measured in cells or cell lines expressing both the IL-22R and the co-receptor IL-20R2, for example the Baf3-hIL-22R/IL20Rb cell line described herein and also in Dumoutier et al. J Biol Chem. 2009 Sep. 25; 284(39): 26377-84, the contents of which are incorporated herein in their entirety. IL-20 induces proliferation in the Baf3-hIL-22R/IL20Rb cell line and therefore IL-20 dependent activation of IL-22R can be determined in this cell line by measuring the proliferation of Baf3-hIL-22R/IL20Rb cells, for example as described in Example 6. In certain embodiments, the antibodies or antigen binding fragments described herein exhibit an IC$_{50}$ (concentration at which 50% inhibition of activation is achieved) in an IL-20 dependent cell-based proliferation assay of less than 1 nM, preferably less than 800 pM. The cell-based proliferation assay is preferably an assay involving the Baf3-hIL-22R/IL20Rb cell line as described herein.

In addition to the proliferation assays described above, IL-22 and/or IL-20-dependent activation of IL-22R may be measured using alternative cellular assays, for example a STAT3 phosphorylation assay as described in WO2011/061119.

In preferred embodiments, the antibodies or antigen binding fragments of the present invention bind to human IL-22R and inhibit both IL-22 dependent activation of IL-22R and IL-20-dependent activation of IL-22R. In such embodiments, the inhibitory or "neutralising" activity of the antibodies or antigen binding fragments may be equipotent for both IL-22 and IL-20-dependent activation. Alternatively, the inhibitory or neutralising activity of the antibodies or antigen binding fragments may be greater for activation of IL-22R mediated by one of the ligands as compared with activation of IL-22R mediated by the other ligand. In certain embodiments, the antibodies or antigen binding fragments of the invention will exhibit more potent inhibitory activity for IL-22 dependent activation of IL-22R as compared with IL-20 dependent activation of IL-22R. However, in such embodiments, the inhibitory activity of the antibody or antigen binding fragment for IL-22-dependent activation of IL-22R will typically be less than 5 fold, preferably less than 4 fold greater, more preferably less than 2 fold greater than the inhibitory activity of the antibody or antigen binding fragment for IL-20-dependent activation of IL-22R.

Cross-Reactivity

In certain embodiments, the antibodies or antigen binding fragments described herein that bind human IL-22R may cross-react with one or more species homologs of IL-22R, for example IL-22R homologs of primate origin.

In certain embodiments, the antibodies or antigen binding fragments of the present invention do not cross-react with murine IL-22R. Alternatively or in addition, the antibodies or antigen binding fragments may bind to one or more IL-22R homologs of primate origin, for example IL-22R proteins from Rhesus and Cynomologus monkeys. The cross-reactivity with other species homologs can be particularly advantageous in the development and testing of therapeutic antibodies. For example, pre-clinical toxicology testing of therapeutic antibodies is frequently carried out in primate species including but not limited to Rhesus and Cynomologus monkeys. Cross-reactivity with these species homologs can therefore be particularly advantageous for the development of antibodies as clinical candidates.

Camelid-Derived Antibodies

In certain embodiments of the invention, the antibodies or antigen binding fragments thereof described herein may comprise at least one hypervariable loop or complementarity determining region obtained from a VH domain or a VL domain of a species in the family Camelidae. In particular, the antibody or antigen binding fragment may comprise VH and/or VL domains, or CDRs thereof, obtained by active immunisation of outbred camelids, e.g. llamas, with an IL-22R antigen or fragment thereof.

By "hypervariable loop or complementarity determining region obtained from a VH domain or a VL domain of a species in the family Camelidae" is meant that that hypervariable loop (HV) or CDR has an amino acid sequence which is identical, or substantially identical, to the amino acid sequence of a hypervariable loop or CDR which is encoded by a Camelidae immunoglobulin gene. In this context "immunoglobulin gene" includes germline genes, immunoglobulin genes which have undergone rearrangement, and also somatically mutated genes. Thus, the amino acid sequence of the HV or CDR obtained from a VH or VL domain of a Camelidae species may be identical to the amino acid sequence of a HV or CDR present in a mature Camelidae conventional antibody. The term "obtained from" in this context implies a structural relationship, in the sense that the HVs or CDRs of the IL-22R antibody embody an amino acid sequence (or minor variants thereof) which was originally encoded by a Camelidae immunoglobulin gene. However, this does not necessarily imply a particular relationship in terms of the production process used to prepare the IL-22R antibody.

Camelid-derived IL-22R antibodies may be derived from any camelid species, including inter alia, llama, dromedary, alpaca, vicuna, guanaco or camel.

IL-22R antibodies comprising camelid-derived VH and VL domains, or CDRs thereof, are typically recombinantly expressed polypeptides, and may be chimeric polypeptides. The term "chimeric polypeptide" refers to an artificial (non-naturally occurring) polypeptide which is created by juxtaposition of two or more peptide fragments which do not otherwise occur contiguously. Included within this definition are "species" chimeric polypeptides created by juxtaposition of peptide fragments encoded by two or more species, e.g. camelid and human.

Camelid-derived CDRs may comprise one of the CDR sequences shown as SEQ ID NOs: 6 and 13 (heavy chain CDR3), or SEQ ID NOs: 4 and 11 (heavy chain CDR2) or SEQ ID NOs: 2 and 9 (heavy chain CDR1) or one of the CDR sequences shown as SEQ ID NOs: 20 and 27 (light chain CDR3), or SEQ ID NOs: 18, 25 and 47 (light chain CDR2) or SEQ ID NOs: 16 and 23 (light chain CDR1).

In one embodiment the entire VH domain and/or the entire VL domain may be obtained from a species in the family Camelidae. In specific embodiments, the camelid-derived VH domain may comprise an amino acid sequence selected from SEQ ID NOs: 29 and 31, whereas the camelid-derived VL domain may comprise an amino acid sequence selected from SEQ ID NOs: 30, 32 and 62. The camelid-derived VH domain and/or the camelid-derived VL domain may then be subject to protein engineering, in which one or more amino acid substitutions, insertions or deletions are introduced into the camelid amino acid sequence. These engineered changes preferably include amino acid substitutions relative to the camelid sequence. Such changes include "humanisation" or "germlining" wherein one or more amino acid residues in a camelid-encoded VH or VL domain are replaced with equivalent residues from a homologous human-encoded VH or VL domain. In certain embodiments, the camelid-derived VH domain may exhibit at least 90%, 95%, 97%, 98% or 99% identity with the amino acid sequence shown as SEQ ID NOs: 29 or 31. Alternatively, or in addition, the camelid-derived VL domain may exhibit at least 90%, 95%, 97%, 98% or 99% identity with the amino acid sequence shown as SEQ ID NOs: 30, 32 or 62.

Isolated camelid VH and VL domains obtained by active immunisation of a camelid (e.g. llama) with a human IL-22R antigen can be used as a basis for engineering antigen binding polypeptides according to the invention. Starting from intact camelid VH and VL domains, it is possible to engineer one or more amino acid substitutions, insertions or deletions which depart from the starting camelid sequence. In certain embodiments, such substitutions, insertions or deletions may be present in the framework regions of the VH domain and/or the VL domain. The purpose of such changes in primary amino acid sequence may be to reduce presumably unfavourable properties (e.g. immunogenicity in a human host (so-called humanization), sites of potential product heterogeneity and or instability (glycosylation, deamidation, isomerisation, etc.) or to enhance some other favourable property of the molecule (e.g. solubility, stability, bioavailability etc.). In other embodiments, changes in primary amino acid sequence can be engineered in one or more of the hypervariable loops (or CDRs) of a Camelidae VH and/or VL domain obtained by active immunisation. Such changes may be introduced in order to enhance antigen binding affinity and/or specificity, or to reduce presumably unfavourable properties, e.g. immunogenicity in a human host (so-called humanization), sites of potential product heterogeneity and or instability, glycosylation, deamidation, isomerisation, etc., or to enhance some other favourable property of the molecule, e.g. solubility, stability, bioavailability, etc.

Thus, in one embodiment, the invention provides a variant IL-22R antibody which contains at least one amino acid substitution in at least one framework or CDR region of either the VH domain or the VL domain in comparison to a camelid-derived VH or VL domain, examples of which include but are not limited to the camelid VH domains comprising the amino acid sequences shown as SEQ ID NOs: 29 and 31, and the camelid VL domains comprising the amino acid sequences shown as SEQ ID NOs: 30, 32 or 62.

In other embodiments, there are provided "chimeric" antibody molecules comprising camelid-derived VH and VL domains (or engineered variants thereof) and one or more constant domains from a non-camelid antibody, for example human-encoded constant domains (or engineered variants thereof). In such embodiments it is preferred that both the VH domain and the VL domain are obtained from the same species of camelid, for example both VH and VL may be from *Lama glama* or both VH and VL may be from *Lama pacos* (prior to introduction of engineered amino acid sequence variation). In such embodiments both the VH and the VL domain may be derived from a single animal, particularly a single animal which has been actively immunised with an IL-22R antigen.

As an alternative to engineering changes in the primary amino acid sequence of Camelidae VH and/or VL domains, individual camelid-derived hypervariable loops or CDRs, or combinations thereof, can be isolated from camelid VH/VL domains and transferred to an alternative (i.e. non-Camelidae) framework, e.g. a human VH/VL framework, by CDR grafting. In particular, non-limiting, embodiments the camelid-derived CDRs may be selected from CDRs having the amino acid sequences shown as SEQ ID NOs: 6 and 13 (heavy chain CDR3), or SEQ ID NOs: 4 and 11 (heavy chain CDR2) or SEQ ID NOs: 2 and 9 (heavy chain CDR1) or one of the CDR sequences shown as SEQ ID NOs: 20 and 27 (light chain CDR3), or SEQ ID NOs: 18, 25 and 47 (light chain CDR2) or SEQ ID NOs:16 and 23 (light chain CDR1).

IL-22R antibodies comprising camelid-derived VH and VL domains, or CDRs thereof, can take various different embodiments in which both a VH domain and a VL domain are present. The term "antibody" herein is used in the broadest sense and encompasses, but is not limited to, monoclonal antibodies (including full length monoclonal antibodies), polyclonal antibodies, multispecific antibodies (e.g., bispecific antibodies), so long as they exhibit the appropriate immunological specificity for an IL-22R protein. The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes) on the antigen, each monoclonal antibody is directed against a single determinant or epitope on the antigen.

"Antibody fragments" comprise a portion of a full length antibody, generally the antigen binding or variable domain thereof. Examples of antibody fragments include Fab, Fab', F(ab')2, bi-specific Fab's, and Fv fragments, diabodies, linear antibodies, single-chain antibody molecules, a single chain variable fragment (scFv) and multispecific antibodies formed from antibody fragments (see Holliger and Hudson, Nature Biotechnol. 23:1126-36 (2005), the contents of which are incorporated herein by reference).

In non-limiting embodiments, IL-22R antibodies comprising camelid-derived VH and VL domains, or CDRs thereof, may comprise CH1 domains and/or CL domains, the amino acid sequence of which is fully or substantially human. Where the antigen binding polypeptide of the invention is an antibody intended for human therapeutic use, it is typical for the entire constant region of the antibody, or at least a part thereof, to have fully or substantially human amino acid sequence. Therefore, one or more or any combination of the CH1 domain, hinge region, CH2 domain, CH3 domain and CL domain (and CH4 domain if present) may be fully or substantially human with respect to its amino acid sequence.

Advantageously, the CH1 domain, hinge region, CH2 domain, CH3 domain and CL domain (and CH4 domain if present) may all have fully or substantially human amino acid sequence. In the context of the constant region of a humanised or chimeric antibody, or an antibody fragment, the term "substantially human" refers to an amino acid sequence identity of at least 90%, or at least 92%, or at least 95%, or at least 97%, or at least 99% with a human constant region. The term "human amino acid sequence" in this context refers to an amino acid sequence which is encoded by a human immunoglobulin gene, which includes germline, rearranged and somatically mutated genes. The invention also contemplates polypeptides comprising constant domains of "human" sequence which have been altered, by one or more amino acid additions, deletions or substitutions with respect to the human sequence, excepting those embodiments where the presence of a "fully human" hinge region is expressly required.

The presence of a "fully human" hinge region in the IL-22R antibodies of the invention may be beneficial both to minimise immunogenicity and to optimise stability of the antibody. As discussed elsewhere herein, it is contemplated that one or more amino acid substitutions, insertions or deletions may be made within the constant region of the heavy and/or the light chain, particularly within the Fc region. Amino acid substitutions may result in replacement of the substituted amino acid with a different naturally occurring amino acid, or with a non-natural or modified amino acid. Other structural modifications are also permitted, such as for example changes in glycosylation pattern (e.g. by addition or deletion of N- or O-linked glycosylation sites). Depending on the intended use of the antibody, it may be desirable to modify the antibody of the invention with respect to its binding properties to Fc receptors, for example to modulate effector function. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp. Med. 176:1191-1195 (1992) and Shopes, B. J. Immunol. 148: 2918-2922 (1992). The invention also contemplates immunoconjugates comprising an antibody as described herein conjugated to a cytotoxic agent such as a chemotherapeutic agent, toxin (e.g., an enzymatically active toxin of bacterial, fungal, plant or animal origin, or fragments thereof), or a radioactive isotope (i.e., a radioconjugate). Fc regions may also be engineered for half-life extension, as described by Chan and Carter, Nature Reviews: Immunology, Vol. 10, pp 301-316, 2010, incorporated herein by reference.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. In alternative embodiments, the Fc region may be engineered such that there is no effector function. An IL-22R antibody having no Fc effector function may be particularly useful as a receptor blocking agent. In certain embodiments, the antibodies of the invention may have an Fc region derived from naturally-occurring IgG isotypes having reduced effector function, for example IgG4. Fc regions derived from IgG4 may be further modified to increase therapeutic utility, for example by the introduction of modifications that minimise the exchange of arms between IgG4 molecules in vivo.

In still another embodiment, the glycosylation of an antibody is modified. For example, an aglycosylated antibody can be made (i.e., the antibody lacks glycosylation). Glycosylation can be altered to, for example, increase the affinity of the antibody for the target antigen. Such carbohydrate modifications can be accomplished by; for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen.

Also envisaged are variant IL-22R antibodies having an altered type of glycosylation, such as a hypofucosylated antibody having reduced amounts of fucosyl residues or a fully or partially de-fucosylated antibody (as described by Natsume et al., Drug Design Development and Therapy, Vol. 3, pp 7-16, 2009) or an antibody having increased bisecting GlcNac structures. Such altered glycosylation patterns have been demonstrated to increase the ADCC activity of antibodies, producing typically 10-fold enhancement of ADCC relative to an equivalent antibody comprising a "native" human Fc domain. Such carbohydrate modifications can be accomplished by, for example, expressing the antibody in a host cell with altered glycosylation enzymatic machinery (as described by Yamane-Ohnuki and Satoh, mAbs 1:3, 230-236, 2009). Examples of non-fucosylated antibodies with enhanced ADCC function are those produced using the Potelligent™ technology of BioWa Inc.

The invention can, in certain embodiments, encompass chimeric Camelidae/human antibodies, and in particular chimeric antibodies in which the VH and VL domains are of fully camelid sequence (e.g. Llama or alpaca) and the remainder of the antibody is of fully human sequence. IL-22R antibodies can include antibodies comprising "humanised" or "germlined" variants of camelid-derived VH and VL domains, or CDRs thereof, and camelid/human chimeric antibodies, in which the VH and VL domains contain one or more amino acid substitutions in the framework regions in comparison to camelid VH and VL domains obtained by active immunisation of a camelid with an IL-22R antigen or a fragment thereof. Such "humanisation" increases the % sequence identity with human germline VH or VL domains by replacing mis-matched amino acid residues in a starting Camelidae VH or VL domain with the equivalent residue found in a human germline-encoded VH or VL domain. IL-22R antibodies may also be CDR-grafted antibodies in which CDRs (or hypervariable loops) derived from a camelid antibody, or otherwise encoded by a camelid gene, are grafted onto a human VH and VL framework, with the remainder of the antibody also being of fully human origin. Such CDR-grafted IL-22R antibodies may contain CDRs having the amino acid sequences shown as SEQ ID NOs: 6 and 13 (heavy chain CDR3), or SEQ ID NOs: 4 and 11 (heavy chain CDR2) or SEQ ID NOs: 2 and 9 (heavy chain CDR1) or one of the CDR sequences shown as SEQ ID NOs: 20 and 27 (light chain CDR3), or SEQ ID NOs: 18, 25 and 47 (light chain CDR2) or SEQ ID NOs:16 and 23 (light chain CDR1).

Humanised, chimeric and CDR-grafted IL-22R antibodies as described above, particularly antibodies comprising hypervariable loops or CDRs derived from active immunisation of camelids, can be readily produced using conventional recombinant DNA manipulation and expression techniques, making use of prokaryotic and eukaryotic host cells engineered to produce the polypeptide of interest and including but not limited to bacterial cells, yeast cells, mammalian cells, insect cells, plant cells, some of them as described herein and illustrated in the accompanying examples.

Camelid-derived IL-22R antibodies include variants wherein the hypervariable loop(s) or CDR(s) of the VH domain and/or the VL domain are obtained from a conventional camelid antibody raised against human IL-22R, but wherein at least one of said (camelid-derived) hypervariable loops or CDRs has been engineered to include one or more amino acid substitutions, additions or deletions relative to the camelid-encoded sequence. Such changes include "humanisation" of the hypervariable loops/CDRs. Camelid-derived HVs/CDRs which have been engineered in this manner may still exhibit an amino acid sequence which is "substantially identical" to the amino acid sequence of a camelid-encoded HV/CDR. In this context, "substantial identity" may permit no more than one, or no more than two amino acid sequence mis-matches with the camelid-encoded HV/CDR. Particular embodiments of the IL-22R antibody may contain humanised variants of the CDR sequences shown as SEQ ID NOs: 6 and 13 (heavy chain CDR3), or SEQ ID NOs: 4 and 11 (heavy chain CDR2) or SEQ ID NOs: 2 and 9 (heavy chain CDR1) or one of the CDR sequences shown as SEQ ID NOs: 20 and 27 (light chain CDR3), or SEQ ID NOs: 18, 25 and 47 (light chain CDR2) or SEQ ID NOs:16 and 23 (light chain CDR1).

The camelid-derived IL-22R antibodies provided herein may be of any isotype. Antibodies intended for human therapeutic use will typically be of the IgA, IgD, IgE, IgG, IgM type, often of the IgG type, in which case they can belong to any of the four sub-classes IgG1, IgG2a and b, IgG3 or IgG4. Within each of these sub-classes it is permitted to make one or more amino acid substitutions, insertions or deletions within the Fc portion, or to make other structural modifications, for example to enhance or reduce Fc-dependent functionalities.

Preferred IL-22R Antibodies—230C9 and 223G5 and Antibodies Related Thereto

Preferred IL-22R antibodies and antigen binding fragments thereof according to the present invention are humanised variants and germlined variants of the camelid-derived antibodies described herein. Humanised and germlined variants exhibit high human homology, and preferably exhibit high homology to human IgG molecules, more preferably IgG1. In certain embodiments, preferred IL-22R antibodies and antigen binding fragments according to the present invention comprise hypervariable loops or CDRs having human or human-like canonical folds, as described elsewhere herein.

The preferred IL-22R antibodies according to the present invention may exhibit an amino acid sequence identity of 93% or greater with one or more human VH domains, particularly across the framework regions FR1, FR2, FR3 and FR4. Alternatively or in addition, the preferred IL-22R antibodies may exhibit an amino acid sequence identity of 96% or greater with one or more human VL domains, particularly across the framework regions FR1, FR2, FR3 and FR4. The preferred IL-22R antibodies according to the present invention may exhibit an amino acid sequence identity of 93% or greater with one or more human VH domains, and a combined amino acid sequence identity of 93% or greater with one or more human VH domains and one or more human VL domains, particularly where sequence identity is determined across the framework regions.

Due to the high human homology, the preferred IL-22R antibodies provided herein exhibit low immunogenicity, as assessed by the Ionza's Epibase™ platform (DRB-1 score) using the "HLA class II—Caucasian v3.0" settings. In certain embodiments, the IL-22R antibodies of the invention exhibit a DRB-1 score of less than 950, preferably less than 850, more preferably less than 750, most preferably less than 650.

Preferred IL-22R antibodies of the invention are monoclonal antibodies containing a hinge region, a CH2 domain and a CH3 domain from a human IgG, preferably an IgG1. In certain embodiments, the Fc region of the monoclonal antibody has no effector function i.e. is a null Fc. This is particularly useful for therapeutic blocking antibodies.

The preferred IL-22R antibodies and antigen binding fragments of the invention exhibit a combination of properties that render them superior to IL-22R antibodies described in the prior art. Preferred IL-22R antibodies and antigen binding fragments of the invention may exhibit the following combination of properties:
  (i) binding to an epitope within the IL-22R protein that does not include Tyr60;
  (ii) binding to an epitope that is located at least in part in the D2 domain of the IL-22R protein;
  (iii) high binding affinity to human IL-22R;
  (iv) inhibition of IL-22-dependent activation of IL-22R and IL-20-dependent activation of IL-22R;
  (v) no cross-reactivity with murine IL-22R; and
  (vi) cross-reactivity with Rhesus and/or Cynomologus IL-22R.

The preferred IL-22R antibodies of the invention may bind to an epitope that does not include the critical residue Tyr60. The preferred IL-22R antibodies of the invention may bind to an epitope that is located at least in part in the D2 domain of IL-22R, wherein the D2 domain is from amino acid 125 to amino acid 228 of SEQ ID NO: 71. The preferred IL-22R antibodies of the invention may also bind to human IL-22R with high affinity, typically exhibiting an off-rate (wherein $k_{off}$ is measured by Biacore) for human IL-22R of less than $2.5 \times 10^{-4}$ s$^{-1}$ when measured as a mAb. In certain embodiments, the preferred IL-22R antibodies of the invention bind to human IL-22R with high affinity exhibiting an off-rate (wherein $k_{off}$ is measured by Biacore) for human IL-22R in the range $1 \times 10^{-6}$ s$^{-1}$ to $2.5 \times 10^{-4}$ s$^{-1}$. In certain embodiments, the preferred IL-22R antibodies of the invention bind to human IL-22R exhibiting a $K_D$ value less than $5 \times 10^{-10}$ M.

The preferred IL-22R antibodies may also inhibit both IL-22 and IL-20 dependent activation of IL-22R, and typically exhibit an inhibitory activity for IL-20-dependent activation that is less than four times greater than the inhibitory activity displayed for IL-22-dependent activation. The preferred IL-22R antibodies may bind to human IL-22R with high affinity and cross-react with IL-22R species homologues from Rhesus and Cynomologus monkeys, but do not cross-react with murine IL-22R.

In certain embodiments, the preferred antibodies and antigen binding fragments according to the present invention comprise at least one heavy chain variable domain (VH) and at least one light chain variable domain (VL) wherein the VH domain comprises:
  a variable heavy chain CDR3 comprising or consisting of the amino acid sequence [VGFSGTYYSES], SEQ ID NO: 6,
  a variable heavy chain CDR2 comprising or consisting of the amino acid sequence [SIYNDASNTAYSDSVKG], SEQ ID NO: 36,
  a variable heavy chain CDR1 comprising or consisting of the amino acid sequence [SYDMN], SEQ ID NO: 34,
  and the VL domain comprises:
  a variable light chain CDR3 comprising or consisting of the amino acid sequence [QSGSSSSNAV], SEQ ID NO: 54,
  a variable light chain CDR2 comprising or consisting of the amino acid sequence [GQNNRPS], SEQ ID NO. 47,
  a variable light chain CDR1 comprising or consisting of the amino acid sequence [QGGYYAH], SEQ ID NO: 16.

The antibodies and antigen binding fragments having the VH and VL domain CDR sequences as defined above may comprise a VH domain comprising or consisting of the sequence of SEQ ID NO:63 and/or a VL domain comprising or consisting of the sequence of SEQ ID NO:64. In certain embodiments, provided herein are antibodies or antigen binding fragments thereof, comprising a heavy chain variable domain and a light chain variable domain, the heavy chain variable domain comprising a VH sequence with at least 85% sequence identity, or at least 90% sequence identity, or at least 95% sequence identity, or at least 97%, 98% or 99% sequence identity, to the amino acid sequence shown as SEQ ID NO:63 and/or the light chain variable domain comprising a VL with at least 85% sequence identity, or at least 90% sequence identity, or at least 95% sequence identity, or at least 97%, 98% or 99% sequence identity, to the amino acid sequence shown as SEQ ID NO:64. For embodiments wherein the domains of the antibodies or antigen binding fragments are defined by a particular percentage sequence identity to a reference sequence, the VH and/or VL domains may retain identical CDR sequences to those present in the reference sequence such that the variation is present only within the framework regions.

The antibodies and antigen binding fragments having the VH and VL domain CDR sequences as defined above may comprise a full-length immunoglobulin heavy chain comprising or consisting of the amino acid sequence of SEQ ID NO: 67 and/or a full length immunoglobulin light chain comprising or consisting of the amino acid sequence of SEQ ID NO: 68. In certain embodiments, provided herein are antibodies comprising a heavy chain with at least 85% sequence identity, or at least 90% sequence identity, or at least 95% sequence identity, or at least 97%, 98% or 99% sequence identity, to the amino acid sequence shown as SEQ ID NO:67 and/or a light chain with at least 85% sequence identity, or at least 90% sequence identity, or at least 95% sequence identity, or at least 97%, 98% or 99% sequence identity, to the amino acid sequence shown as SEQ ID NO:68.

For embodiments wherein the chains of the antibodies are defined by a particular percentage sequence identity to a reference sequence, the heavy chain and/or light chain may retain identical CDR sequences to those present in the reference sequence such that the variation is present only outside the CDR regions.

In certain embodiments, the preferred antibodies and antigen binding fragments according to the present invention comprise at least one heavy chain variable domain (VH) and at least one light chain variable domain (VL) wherein the VH domain comprises:
  a variable heavy chain CDR3 comprising or consisting of the amino acid sequence [PPGPFKAHYNGAKY], SEQ ID NO: 43, a variable heavy chain CDR2 comprising or consisting of the amino acid sequence [GIHISGGITYYTDSVKG], SEQ ID NO: 41,
a variable heavy chain CDR1 comprising or consisting of the amino acid sequence [SYFMS], SEQ ID NO: 9, and the VL domain comprises:
a variable light chain CDR3 comprising or consisting of the amino acid sequence [ASYRLYADYV], SEQ ID NO: 27,
a variable light chain CDR2 comprising or consisting of the amino acid sequence [EVNKRSS], SEQ ID NO. 59,
a variable light chain CDR1 comprising or consisting of the amino acid sequence [TGTSSDIGSYNYVS], SEQ ID NO: 57.

The antibodies and antigen binding fragments having the VH and VL domain CDR sequences as defined above may comprise a VH domain comprising or consisting of the sequence of SEQ ID NO:65 and/or a VL domain comprising or consisting of the sequence of SEQ ID NO:66. In certain embodiments, provided herein are antibodies or antigen binding fragments thereof, comprising a heavy chain variable domain and a light chain variable domain, the heavy chain variable domain comprising a VH sequence with at least 85% sequence identity, or at least 90% sequence identity, or at least 95% sequence identity, or at least 97%, 98% or 99% sequence identity, to the amino acid sequence shown as SEQ ID NO:65 and/or the light chain variable domain comprising a VL with at least 85% sequence identity, or at least 90% sequence identity, or at least 95% sequence identity, or at least 97%, 98% or 99% sequence identity, to the amino acid sequence shown as SEQ ID NO:66. For embodiments wherein the domains of the antibodies or antigen binding fragments are defined by a particular percentage sequence identity to a reference sequence, the VH and/or VL domains may retain identical CDR sequences to those present in the reference sequence such that the variation is present only within the framework regions.

The antibodies and antigen binding fragments having the VH and VL domain CDR sequences as defined above may comprise a full-length immunoglobulin heavy chain comprising or consisting of the amino acid sequence of SEQ ID NO: 69 and/or a full length immunoglobulin light chain comprising or consisting of the amino acid sequence of SEQ ID NO: 70. In certain embodiments, provided herein are antibodies comprising a heavy chain with at least 85% sequence identity, or at least 90% sequence identity, or at least 95% sequence identity, or at least 97%, 98% or 99% sequence identity, to the amino acid sequence shown as SEQ ID NO:69 and/or a light chain with at least 85% sequence identity, or at least 90% sequence identity, or at least 95% sequence identity, or at least 97%, 98% or 99% sequence identity, to the amino acid sequence shown as SEQ ID NO:70.

For embodiments wherein the chains of the antibodies are defined by a particular percentage sequence identity to a reference sequence, the heavy chain and/or light chain may retain identical CDR sequences to those present in the reference sequence such that the variation is present only outside the CDR regions.

Cross-Competing Antibodies

The present invention also includes (monoclonal) antibodies or antigen-binding fragments thereof that "cross-compete" with the antibodies or antigen binding fragments disclosed herein.

In particular, provided herein are antibodies or antigen-binding fragments thereof, which bind to the cytokine receptor IL-22R and cross-compete with antibodies or antigen binding fragments thereof, comprising a combination of variable heavy chain CDR3 (HCDR3), variable heavy chain CDR2 (HCDR2) and variable heavy chain CDR1 (HCDR1), variable light chain CDR3 (LCDR3), variable light chain CDR2 (LCDR2) and variable light chain CDR1 (LCDR1) wherein the combination is selected from the group consisting of: (i) HCDR3 comprising SEQ ID NO: 43; HCDR2 comprising SEQ ID NO: 41; HCDR1 comprising SEQ ID NO: 9; LCDR3 comprising SEQ ID NO: 27; LCDR2 comprising SEQ ID NO: 59; LCDR1 comprising SEQ ID NO: 57; and (ii) HCDR3 comprising SEQ ID NO: 13; HCDR2 comprising SEQ ID NO: 11; HCDR1 comprising SEQ ID NO: 9; LCDR3 comprising SEQ ID NO: 27; LCDR2 comprising SEQ ID NO: 25; LCDR1 comprising SEQ ID NO: 23.

In certain embodiments, provided herein are antibodies or antigen-binding fragments thereof, which bind to the cytokine receptor IL-22R and cross-compete with antibodies or antigen binding fragments thereof comprising at least one heavy chain variable domain (VH) and at least one light chain variable domain (VL) wherein the VH domain comprises:
a variable heavy chain CDR3 comprising or consisting of the amino acid sequence [PPGPFKAHYNGAKY], SEQ ID NO: 43,
a variable heavy chain CDR2 comprising or consisting of the amino acid sequence [GIHISGGITYYTDSVKG], SEQ ID NO: 41,
a variable heavy chain CDR1 comprising or consisting of the amino acid sequence [SYFMS], SEQ ID NO: 9, and the VL domain comprises:
a variable light chain CDR3 comprising or consisting of the amino acid sequence [ASYRLYADYV], SEQ ID NO: 27,
a variable light chain CDR2 comprising or consisting of the amino acid sequence [EVNKRSS], SEQ ID NO. 59,
a variable light chain CDR1 comprising or consisting of the amino acid sequence [TGTSSDIGSYNYVS], SEQ ID NO: 57.

The cross-competing antibodies or antigen-binding fragments thereof may compete with antibodies or antigen binding fragments having a VH domain comprising or consisting of the sequence of SEQ ID NO:65 and/or a VL domain comprising or consisting of the sequence of SEQ ID NO:66. The cross-competing antibodies or antigen-binding fragments thereof may compete with antibodies having a full-length immunoglobulin heavy chain comprising or consisting of the amino acid sequence of SEQ ID NO: 69 and/or a full length immunoglobulin light chain comprising or consisting of the amino acid sequence of SEQ ID NO: 70.

In the context of the present invention, cross-competing antibodies are those that bind IL-22R at site(s) that overlap or are identical to the site(s) at which the present IL-22R antibodies bind. Competing (monoclonal) antibodies or antigen-binding fragments thereof can be identified, for example, via an antibody competition assay. For example, an IL-22R antigen or fragment thereof can be bound to a solid support. Then, an antibody or antigen binding fragment thereof of the present invention and a monoclonal antibody or antigen-binding fragment thereof suspected of being able to compete with such invention antibody are added. One of the two molecules is labelled. If the labelled compound and the unlabeled compound bind to separate and discrete sites on the IL-22R antigen, the labelled compound will bind to the same level whether or not the suspected competing compound is present. However, if the sites of interaction are identical (or overlapping), the unlabeled compound will compete, and the amount of labelled compound bound to the antigen will be lowered. If the unlabeled compound is present in excess, very little, if any, labelled compound will bind. For purposes of the present invention, competing monoclonal antibodies or antigen-binding fragments thereof are those that decrease the binding of the present antibodies to IL-22R by about 50%, about 60%, about 70%, about 80%, about 85%, about 90%, about 95%, or about 99%. Details of procedures for carrying out such competition assays are well known in the art and can be found, for example, in Harlow and Lane (1988) Antibodies, A Laboratory Manual, Cold Spring Harbor Laboratory Press, Cold Spring Harbor, N.Y., pages 567-569, ISBN 0-87969-314-2. Such assays can be made quantitative by using purified antibodies. A standard curve is established by titrating one antibody against itself, i.e., the same antibody is used for both the label and the competitor. The capacity of an unlabeled competing monoclonal antibody or antigen-binding fragment thereof to inhibit the binding of the labelled molecule to the plate is titrated. The results are plotted, and the concentrations necessary to achieve the desired degree of binding inhibition are compared.

Polynucleotides Encoding IL-22R Antibodies

The invention also provides polynucleotide molecules encoding the IL-22R antibodies of the invention or fragments thereof, also expression vectors containing said nucleotide sequences of the invention operably linked to regulatory sequences which permit expression of the antibodies or fragments thereof in a host cell or cell-free expression system, and a host cell or cell-free expression system containing this expression vector.

In particular embodiments, the polynucleotide encoding the IL-22R antibody of the invention may comprise one or more of the polynucleotide sequences shown as SEQ ID NOs: 52, 73, 74, 75, 76, 77, 78, 79, 80 or 81, which sequences encode VH or VL domains of IL-22R antibodies.

In certain embodiments, the polynucleotide encoding the IL-22R antibody of the invention may comprise a variant sequence which encodes a functional VH or VL domain of an IL-22R antibody, wherein said variant sequence exhibits at least 80%, 85%, 90%, 95%, 97% or 99% sequence identity when optimally aligned to any one of SEQ ID NOs: 52, 73, 74, 75, 76, 77, 78, 79, 80 or 81.

In this context, % sequence identity between two polynucleotide sequences may be determined by comparing these two sequences aligned in an optimum manner and in which the polynucleotide sequence to be compared can comprise additions or deletions with respect to the reference sequence for an optimum alignment between these two sequences. The percentage of identity is calculated by determining the number of identical positions for which the nucleotide residue is identical between the two sequences, by dividing this number of identical positions by the total number of positions in the comparison window and by multiplying the result obtained by 100 in order to obtain the percentage of identity between these two sequences. For example, it is possible to use the BLAST program, "BLAST 2 sequences" (Tatusova et al, "Blast 2 sequences—a new tool for comparing protein and nucleotide sequences", FEMS Microbiol Lett. 174:247-250) available on the site http://www.ncbi.nlm.nih.gov/gorf/bl2.html, the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program.

In certain embodiments, the heavy chain variable domain and the light chain variable domain of the IL-22R antibodies or antigen-binding fragments according to the present invention are encoded by a combination of first and second polynucleotide sequences, wherein the first and second polynucleotide sequences are selected from the following pairs:

(i) a first polynucleotide encoding a variable heavy chain domain comprising SEQ ID NO: 52 and a second polynucleotide encoding a variable light chain domain comprising SEQ ID NO: 73;

(ii) a first polynucleotide encoding a variable heavy chain domain comprising SEQ ID NO: 74 and a second polynucleotide encoding a variable light chain domain comprising SEQ ID NO: 75;

(iii) a first polynucleotide encoding a variable heavy chain domain comprising SEQ ID NO: 76 and a second polynucleotide encoding a variable light chain domain comprising SEQ ID NO: 77;

(iv) a first polynucleotide encoding a variable heavy chain domain comprising SEQ ID NO: 78 and a second polynucleotide encoding a variable light chain domain comprising SEQ ID NO: 79; or (v) a first polynucleotide encoding a variable heavy chain domain comprising SEQ ID NO: 80 and a second polynucleotide encoding a variable light chain domain comprising SEQ ID NO: 81.

Polynucleotide molecules encoding the antibodies of the invention include, for example, recombinant DNA molecules. The terms "nucleic acid", "polynucleotide" or a "polynucleotide molecule" as used herein interchangeably and refer to any DNA or RNA molecule, either single- or double-stranded and, if single-stranded, the molecule of its complementary sequence. In discussing nucleic acid molecules, a sequence or structure of a particular nucleic acid molecule may be described herein according to the normal convention of providing the sequence in the 5' to 3' direction. In some embodiments of the invention, nucleic acids or polynucleotides are "isolated." This term, when applied to a nucleic acid molecule, refers to a nucleic acid molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or non-human host organism. When applied to RNA, the term "isolated polynucleotide" refers primarily to an RNA molecule encoded by an isolated DNA molecule as defined above. Alternatively, the term may refer to an RNA molecule that has been purified/separated from other nucleic acids with which it would be associated in its natural state (i.e., in cells or tissues). An isolated polynucleotide (either DNA or RNA) may further represent a molecule produced directly by biological or synthetic means and separated from other components present during its production.

For recombinant production of an antibody according to the invention, a recombinant polynucleotide encoding it may be prepared (using standard molecular biology techniques) and inserted into a replicable vector for expression in a chosen host cell, or a cell-free expression system. Suitable host cells may be prokaryote, yeast, or higher eukaryote cells, specifically mammalian cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen. Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); mouse myeloma cells SP2/0-AG14 (ATCC CRL 1581; ATCC CRL 8287) or NS0 (HPA culture collections no. 85110503); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), as well as DSM's PERC-6 cell line. Expression vectors suitable for use in each of these host cells are also generally known in the art.

It should be noted that the term "host cell" generally refers to a cultured cell line. Whole human beings into which an expression vector encoding an antigen binding polypeptide according to the invention has been introduced are explicitly excluded from the definition of a "host cell".

Antibody Production

In an important aspect, the invention also provides a method of producing antibodies of the invention which comprises culturing a host cell (or cell free expression system) containing polynucleotide (e.g. an expression vector) encoding the antibody under conditions which permit expression of the antibody, and recovering the expressed antibody. This recombinant expression process can be used for large scale production of antibodies, including IL-22R antibodies according to the invention, including monoclonal antibodies intended for human therapeutic use. Suitable vectors, cell lines and production processes for large scale manufacture of recombinant antibodies suitable for in vivo therapeutic use are generally available in the art and will be well known to the skilled person.

Therapeutic Utility of IL-22R Antibodies

The IL-22R antibodies provided herein can be used as medicaments, particularly for use in the treatment or prophylaxis of disorders where the pathology is attributable to dysregulated signalling via the cell surface IL-22R complexes. Such dysregulated signalling may be linked to overexpression or overproduction of any one of the cytokines IL-22, IL-20 and/or IL-24.

The term "treating" or "treatment" means slowing, interrupting, arresting, controlling, stopping, reducing severity of a symptom, disorder, condition or disease, but does not necessarily involve a total elimination of all disease-related symptoms, conditions or disorders. The term "prophylaxis" means preventing the onset of a disorder, condition or disease or preventing the onset of symptoms associated with a disorder, condition or disease.

The ligands that signal via the IL-22R have been implicated in a number of diseases and since IL-22R is selectively expressed on skin and epithelial cells, the key diseases are those affecting skin and epithelia including but not limited to psoriasis, psoriatic arthritis and atopic dermatitis. High levels of IL-22 have been found in human psoriatic plaques (Boniface et al., Clin Exp Immunol. 150: 407-415 (2007)) and the involvement of this cytokine in the pathogenesis of psoriasis has been demonstrated experimentally in mouse models of skin inflammation (Ma et al., J Clin Invest. 118: 597-607 (2008); Van Belle et al. J Immunol. January 1; 188(1):462-9 (2012)).

In certain embodiments, provided herein are methods of treating skin inflammatory diseases. In certain embodiments, provided herein are methods of treating skin inflammatory diseases selected from psoriasis, psoriatic arthritis, contact dermatitis or atopic dermatitis in a human subject. The methods comprise administering to a patient in need thereof a therapeutically effective amount of any of the IL-22R antibodies or antigen binding fragments as defined elsewhere herein. All embodiments of the IL-22R antibodies of antigen binding fragments as described herein are equally applicable to the methods of treatment of the present invention.

In certain embodiments, provided herein are methods of treating Sjögren syndrome, or cancers selected from hepatocarcinoma, liposarcoma, oral squamous cell carcinoma, colon and colorectal cancer, pancreatic cancer, small- and large-cell lung cancer, breast cancer, glioblastoma, cutaneous T-cell lymphoma, anaplastic large cell lymphoma, mantle cell lymphoma, in a human subject which methods comprise administering to a patient in need thereof a therapeutically effective amount of any of the IL-22R antibodies or antigen binding fragments as defined elsewhere herein. All embodiments of the IL-22R antibodies of antigen binding fragments as described herein are equally applicable to the methods of treatment of the present invention.

For human therapeutic use the IL-22R antibodies described herein may be administered to a human subject in need of treatment in an "effective amount". The term "effective amount" refers to the amount or dose of a IL-22R antibody which, upon single or multiple dose administration to a human patient, provides therapeutic efficacy in the treatment of disease. Therapeutically effective amounts of the IL-22R antibody can comprise an amount in the range of from about 0.1 mg/kg to about 20 mg/kg per single dose. The amount of antibody administered at any given time point may be varied so that optimal amounts of IL-22R antibody, whether employed alone or in combination with any other therapeutic agent, are administered during the course of treatment.

It is also contemplated to administer the IL-22R antibodies described herein, or pharmaceutical compositions comprising such antibodies, in combination with any other suitable treatment for the diseases identified above, as a combination therapy.

Pharmaceutical Compositions

The scope of the invention includes pharmaceutical compositions, containing one or a combination of IL-22R antibodies of the invention, or antigen-binding fragments thereof, formulated with one or more a pharmaceutically acceptable carriers or excipients. Such compositions may include one or a combination of (e.g., two or more different) IL-22R antibodies. Techniques for formulating monoclonal antibodies for human therapeutic use are well known in the art and are reviewed, for example, in Wang et al., Journal of Pharmaceutical Sciences, Vol. 96, pp 1-26, 2007, the contents of which are incorporated herein in their entirety.

In certain embodiments, the pharmaceutical compositions are formulated for administration to a subject via any suitable route of administration including but not limited to intramuscular, intravenous, intradermal, intraperitoneal injection, subcutaneous, epidural, nasal, oral, rectal, topical, inhalational, buccal (e.g., sublingual), and transdermal administration. In preferred embodiments, the composition is formulated for subcutaneous administration.

INCORPORATION BY REFERENCE

Various publications are cited in the foregoing description and throughout the following examples, each of which is incorporated by reference herein in its entirety.

EXAMPLES

The invention will be further understood with reference to the following non-limiting examples.

Example 1 Immunization of Llama

Two llamas were immunized with a mixture of recombinant human IL22R protein (R&D systems) and human Fn14-Fc according to the immunization schedule shown in Table 3 below. After six weekly injections of recombinant proteins, blood was collected and the sera of the immunized llamas were used to measure the humoral immune response against IL22R by detecting the presence of antibodies against the immunized antigen before immunization and after immunization. Both llamas produced a significant and specific immune response against IL22R.

TABLE 3

| Immunization schedule for each llama | | | | |
|---|---|---|---|---|
| Week | Date | Day | Antigen | Tissue collection |
|  |  |  |  | 10 ml pre-immune blood (serum) |
| 39 | 29 Sep. 2010 | 0 | IL-22R (80 µg) + Fn14-Fc (80 µg) | — |
| 40 | 7 Oct. 2010 | 8 | IL-22R (40 µg) + Fn14-Fc (40 µg) | — |
| 41 | 14 Oct. 2010 | 15 | IL-22R (40 µg) + Fn14-Fc (40 µg) | — |
| 42 | 21 Oct. 2010 | 22 | IL-22R (40 µg) + Fn14-Fc (40 µg) | — |
| 43 | 28 Oct. 2010 | 29 | IL-22R (40 µg) + Fn14-Fc (40 µg) | — |
| 44 | 4 Nov. 2010 | 36 | IL-22R (40 µg) + Fn14-Fc (40 µg) | — |
| 45 | 8 Nov. 2010 | 40 |  | 400 ml immune blood 10 ml immune blood (plasma) |

Example 2 Library Construction and Selection

After immunization, PBMCs were harvested and RNA was extracted. Random primed cDNA synthesis was carried out and the llama VHCH1, VλCλ and VκCκ gene segments were PCR amplified. Two approaches were used to PCR amplify the light chains. The first approach used a primary PCR amplification with primers without restriction site linkers, followed by PCR amplification with primers tagged with restriction sites (ApaLI and AscI). For the second approach, the tagged primers were used to amplify the cDNA directly. The VHCH1 libraries were built using a two-step PCR, in which 25 cycles with non-tagged primers were carried out followed by 10 cycles using tagged versions of these primers (containing SfiI and NotI restriction sites) (see WO2010/001251).

The PCR-amplified light chains were digested with ApaLI and AscI whilst the PCR-amplified heavy chains were digested with SfiI and NotI, and combined into a Fab library by cloning the light chain library insert into heavy chain library pCB3 vector using ApaLI and AscI restriction sites. The final Fab libraries were found to be of requisite diversity >$10^9$ different clones).

After library construction, phages were produced and phage display selection was performed on human IL22R (Biotechne, 2770-LR). For selection of IL22R-specific clones, human IL22R was (i) coated directly to a MaxiSorp™ plate (Nunc); or (ii) captured with a non-competitive anti-human IL22R antibody (MAB2770, R&D systems); or (iii) captured with neutravidin after biotinylation. The coating and capture of IL22R was usually done in two different concentrations; for example 5 µg/ml and 0.1 µg/ml.

After the first round of selection no clear enrichment was seen but after the second and third round, dose-dependent enrichments in all libraries were observed; up to 100-fold after the second round and 10,000-fold after the third round. The enrichments on antibody captured IL22R were found to be higher compared to those on the directly coated IL22R. This could be due to the fact that the IL22R is only 25 kDa and the direct coating affects its conformation or limits the available epitope. Therefore a third selection campaign was done using biotinylated hIL22R.

In addition to the selections described above, two extra rounds of selection were performed on biotinylated recombinant mouse IL22R after a first round of selection on MAB2770-captured human IL-22R. This selection was done to identify Fab cross-reactive with mouse IL22R. As a positive control on the selections, selection on neutravidin-captured human IL-22R-biotin was conducted in parallel. Overall the selection process was very successful with significant enrichment observed for IL22R Fab binders.

Example 3 Screening for IL22R Specific Fabs

After the successful phage display selection, the Fabs present in periplasm were tested for their ability to block binding of IL-22 to the IL22R. In addition, screening was carried out to identify the clone binding to the mouse IL22R1. A new approach was developed based on surface plasmon resonance (SPR), which allowed testing for both ligand competition, affinity to human and mouse cross-reactivity in one screen.

The different channels of a Biacore chip (CM5) were coated with:
1. Nothing (Blank)
2. IL-22 (3000RU) to test for competitive activity of the Fab (when IL22R is co-injected)
3. Human IL22R (3000RU) to test for binding to the target
4. Mouse IL22R (2500RU) to test for cross-reactivity To test for ligand competition, a low concentration of soluble IL22R1 (0.2 µg/ml) was premixed with the periplasmic extracts before injection. In this way, it was also possible to measure the ability of the Fab to block the ligand-receptor interaction on channel 2. The periplasmic extracts obtained were screened for binding to human IL22R (channel 3) and mouse IL22R (channel 4).

The advantage of this method compared to conventional ELISA (binding or competitive) is that several characteristics of the Fab are tested at the same time: 1) binding to the target human IL-22R; 2) competitive activity; and 3) cross-reactivity. Furthermore, the measure of the off-rates gives a strong indication of the affinity of the Fabs tested.

Using this alternative screening method, Fabs with all possible characteristics were identified and categorised based on their off-rate:
Competing or non-competing
Cross-reactive and non-cross-reactive
Competing and cross-reactive
Non-competing and cross-reactive
Various clones were then sent for sequencing.

Example 4 Sequence Analysis of IL-22R Fabs

Clones identified by the Biacore analysis (e.g. ligand competition, maximal binding, low off-rate or mouse cross-reactivity) were sequenced. The clones were then grouped based on their CDR3 identity to form VH families.

In total, 67 different VHs belonging to 13 different VH families were identified. Many more light chain families (more than 80 Vlambda and Vkappa sequences) were identified. The large diversity in sequence and function of the Fabs show that the immunization and selection were very successful.

The VH and VL domain amino acid sequences of clones of particular interest are shown in Tables 4-6 below, and polynucleotide sequences of these clones are shown in Table 7.

TABLE 4

Framework regions and CDR sequences for VH domains of IL-22R Fabs

| Clone | FR1 | SEQ ID NO. | CDR1 | SEQ ID NO. | FR2 | SEQ ID NO. | CDR2 | SEQ ID NO. | FR3 | SEQ ID NO. | CDR3 | SEQ ID NO. | FR4 | SEQ ID NO. |
|---|---|---|---|---|---|---|---|---|---|---|---|---|---|---|
| 157A2 | QVQLVESGGGLVQPGGSLRLSCAASGFTFS | 1 | SYDMS | 2 | WVRQAPGKGLEWVS | 3 | SIYNDGSNTAYSDSVKG | 4 | RFTISRDNAKNTLYLQMNSLKSEDTAVYYCAK | 5 | VGFSGTYYSES | 6 | WGQGTQVTVSS | 7 |
| 166G8 | QVQLVESGGGLVQPGDSLRLSCAASGFTFG | 8 | SYFMS | 9 | WVRQAPGKGPEWVS | 10 | GIHISGGITYYLDSVKG | 11 | RFTISRDNAKNTLYLQMNNLKPEDTAVYYCVT | 12 | PPGPFKAHYNGMKY | 13 | WGKGTLVTVSS | 14 |

TABLE 5

Framework regions and CDR sequences for VL domains of IL-22R Fabs

| Clone | FR1 | SEQ ID NO. | CDR1 | SEQ ID NO. | FR2 | SEQ ID NO. | CDR2 | SEQ ID NO. | FR3 | SEQ ID NO. | CDR3 | SEQ ID NO. | FR4 | SEQ ID NO. |
|---|---|---|---|---|---|---|---|---|---|---|---|---|---|---|
| 157A2 | NFMLTQPSAVSVSLGQTAKITC | | QGGYYAH | 15 | WYQQKPGQAPVLVIY | 16 | GNNNRPS | 17 | NTATLTISGAQAEDEAEYYC | 18 | QSGSSSANAV | 19 | FGGGTHLTVL | 20 | | 21 |
| 166G8 | NFMLTQPPSVSGTLGKTVTISC | | TGTSRDIGDYNYVS | 22 | WYQQLPGLAPKLLIY | 23 | KVNTRSS | 24 | NTASLTISGLQSEDEADYYC | 25 | ASYRLYADYV | 26 | FGGGTHLTVL | 27 | | 28 |

TABLE 6

Variable domain sequences for IL-22R Fabs

| Clone | VH | SEQ ID NO. | VL | SEQ ID NO. |
|---|---|---|---|---|
| 157A2 | QVQLVESGGGLVQPGGSLRLSCAASGFTFSSYDMSWV RQAPGKGLEWVSSIYNDGSNTAYSDSVKGRFTISRDNA KNTLYLQMNSLKSEDTAVYYCAKVGFSGTYYSESWGQ GTQVTVSS | 29 | NFMLTQPSAVSVSLGQTAKITCQGGYYAHWYQQK PGQAPVLVIYGNNNRPSGIPERFSGSSSGNTATLTI SGAQAEDEAEYYCQSGSSSANAVFGGGTHLTVL | 30 |
| 166G8 | QVQLVESGGGLVQPGDSLRLSCAASGFTFGSYFMSWV RQAPGKGPEWVSGIHISGGITYYLDSVKGRFTISRDNAK NTLYLQMNNLKPEDTAVYYCVTPPGPFKAHYNGMKYW GKGTLVTVSS | 31 | NFMLTQPPSVSGTLGKTVTISCTGTSRDIGDYNYVS WYQQLPGLAPKLLIYKVNTRSSGTPDRFSGSKSGN TASLTISGLQSEDEADYYCASYRLYADYVFGGGTH LTVL | 32 |

TABLE 7

Polynucleotide sequences for IL-22R Fabs

| Clone | VH | SEQ ID NO. | VL | SEQ ID NO. |
|---|---|---|---|---|
| 157A2 | CAGGTGCAGCTCGTGGAGTCTGGGGGAGGCTTGGT GCAGCCTGGGGTTCTCTGAGACTCTCCTGTGCAGC CTCTGGATTCACCTTCAGTAGCTACGACATGAGCTGG GTCCGCCAGGCTCCAGGGAAGGGGCTGGAGTGGGT GTCCAGTATTTATAATGACGGTAGTAACACAGCCTATT CAGACTCCGTGAAGGGCCGATTCACCATCTCCAGAG ACAACGCCAAGAACACGTTGTATCTGCAAATGAACAG CTTGAAATCTGAGGACACGGCCGTGTATTACTGTGCA AAAGTTGGCTTTAGTGGTACTTACTACAGTGAATCAT GGGGCCAGGGGACCCAGGTCACCGTGTCCTCA | 52 | AATTTTATGCTGACTCAGCCCTCCGCGGTGTCCG TGTCTTTGGGACAGACCGCCAAGATCACCTGCC AAGGGGGCTATTATGCTCACTGGTACCAGCAGA AGCCAGGCCAGGCCCCTGTGTTGGTCATCTATG GAAATAATAATAGGCCCTCAGGGATCCCTGAGC GCTTCTCTGGCTCCAGTTCTGGGAACACAGCCA CCCTGACCATCAGCGGGGCCCAGGCTGAGGAC GAGGCCGAGTATTACTGTCAGTCAGGAAGCAGT AGTGCTAATGCTGTGTTCGGCGGAGGGACCCAT CTG ACCGTCCTG | 73 |
| 166G8 | CAGGTGCAGCTGGTGGAGTCTGGGGGAGGCTTGGT GCAGCCTGGGGATTCTCTGAGACTCTCCTGTGCAGC CTCTGGATTCACCTTCGGAAGCTATTTCATGAGCTGG GTCCGCCAGGCTCCAGGAAAGGGGCCCGAGTGGGT CTCAGGTATTCATATTAGTGGTGGTATTACATACTACT TAGACTCCGTGAAGGGCCGATTCACCATCTCCAGAG ACAACGCCAAGAACACGCTGTATCTGCAAATGAACAA CCTGAAACCTGAGGACACGGCCGTGTATTATTGTGTA ACACCCCCGGGCCCCTTTAAGGCCCATTACAATGGC ATGAAGTACTGGGGCAAAGGGACCCTGGTCACCGTC TCCTCA | 74 | AATTTTATGCTGACTCAGCCTCCCTCCGTGTCTG GAACTCTGGGAAAGACGGTCACCATCTCCTGCA CTGGAACCAGTCGTGACATTGGGGACTATAACTA TGTCTCCTGGTATCAACAGCTCCCAGGATTGGCC CCCAAACTCCTGATCTATAAAGTCAACACTCGAT CCTCAGGGACCCCTGATCGCTTCTCTGGCTCCA AGTCAGGCAACAGGCCTCCCTGACCATCTCTG GGCTCCAGTCTGAGGACGAGGCTGATTATTACT GTGCCTCATATAGACTGTACGCCGATTATGTGTT CGGCGGAGGGACCCATCTGACCGTCCTG | 75 |

Example 5 Characterisation of Fabs

The clones with the best off-rates were re-cloned into pCB4, expressed and purified by IMAC (Talon from Clonentech). These clones were tested again using Biacore. The results of the further Fab characterisation are shown in Table 8 below.

TABLE 8

Characterisation of IL-22R binding Fabs

| VH family | Clone | Binding to human IL-22R | Binding to mouse IL-22R | IL-22 blocking | Off-rate ($s^{-1}$) |
|---|---|---|---|---|---|
| 1 | 170B2 | Yes | Yes* | Yes | 3.5E−04 |
| 1 | 170D6 | Yes | Yes* | Yes | 5.8E−03 |
| 1 | 160C8 | Yes | No | Yes | 3.2E−03 |
| 2 | 160C2 | Yes | Yes | No | 1.7E−03 |
| 3 | 158C4 | Yes | Yes | No | 6.7E−03 |
| 4 | 157A2 | Yes | No | Yes | 3.7E−03 |
| 4 | 171F4 | Yes | No | Yes | 5.9E−03 |
| 4 | 171A1 | Yes | No | Yes | 4.1E−03 |
| 4 | 171B1 | Yes | No | Yes | 1.9E−03 |
| 4 | 171C1 | Yes | No | Yes | 3.5E−03 |
| 5 | 159B8 | Yes | No | Yes | 1.5E−03 |
| 5 | 166G8 | Yes | No | Yes | 8.8E−04 |
| 5 | 169C1 | Yes | No | Yes | 3.2E−04 |
| 5 | 169H7 | Yes | No | Yes | 4.7E−04 |
| 5 | 169C8 | Yes | No | Yes | 4.3E−04 |
| 5 | 169H10 | Yes | No | Yes | 6.5E−04 |
| 5 | 171F10 | Yes | No | Yes | 1.2E−03 |
| 6 | 157C8 | Yes | Yes | Yes | 4.3E−03 |
| 6 | 157G8 | Yes | Yes | Yes | 8.6E−04 |
| 6 | 171A8 | Yes | Yes | Yes | 4.8E−03 |
| 7 | 157B8 | Yes | No | No | 7.7E−04 |
| 8 | 158H4 | Yes | No | No | 2.9E−03 |
| 11 | 165B8 | Yes | Yes | No | 9.7E−04 |
| 19 | 169G4 | Yes | — | No | 7.3E−04 |
| 20 | 172C9 | Yes | Yes | No | 6.1E−04 |
| 22 | 166D8 | Yes | No | No | 3.8E−03 |

*observed only once with purified Fab (not peri or mAb) suggesting very low affinity Depending on the diversity in the VH family, competing activity and affinity (measured using the $k_{off}$ obtained in the Biacore) one or several clones from each family were selected and reformatted into monoclonal antibodies (mAb) for further characterisation.

Example 6 Characterization of IL-22R Binding mAbs

As noted above, selective clones of each VH family were produced as IgG1. After re-cloning of the HC and LC variable regions into separate pUPE expression vectors containing the human constant domains, HEK293E were transiently transfected with the two plasmids, one encoding the entire heavy chain and a second encoding the light chain. The transfected cells were allowed to express the antibodies during a 6-day cell culture period. After antibody purification from cell culture supernatant using protein A beads, the purified antibodies were tested for their ability to neutralize human and mouse IL22R signalling using different cell lines as described below.

BW-hIL22R cell line: Is derived from the BW cell line and has stable expression of human IL22R which introduces IL22-dependent growth arrest. Therefore the cells will proliferate only when the IL22-IL22R interaction is blocked. A potent antibody will promote proliferation at low antibody concentration. Proliferation is measured by thymidine incorporation.

Baf3-mIL22R cell line: Is derived from the Baf3 cell line and has stable expression of mouse IL22R which gives rise to an IL22-dependent proliferation. Antibody neutralizing the mIL22R will block the proliferation in an antibody concentration dependent manner.

Baf3-hIL22R/IL20Rb cell line: Is derived from the Baf3 cell line but co-expresses hIL22R with hIL20Rbeta allowing the cells to proliferate in the presence of IL20. Antibody neutralizing the hIL22R will block the proliferation of cells stimulated with IL20.

Figure 1:
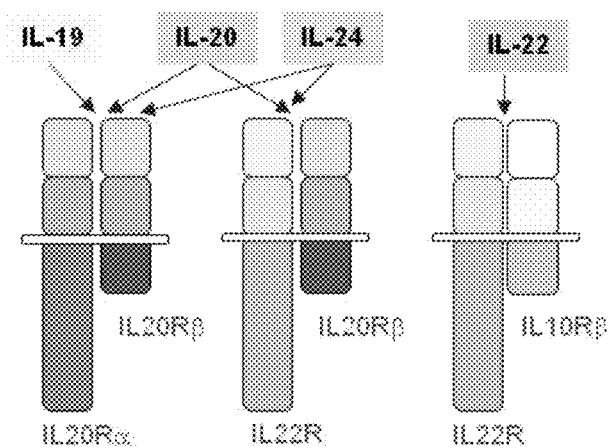
FIG. 1 shows the different receptor complexes that mediate signalling via the cytokines IL-22, IL-20 and IL-24. IL-22R is capable of forming a heterodimeric complex with two different receptor partners, IL-10Rβ (or IL-10R2) and IL-20Rβ (or IL-20R2), and activation of these different complexes by ligand binding triggers signalling via intracellular downstream pathways.
Figure 4A:
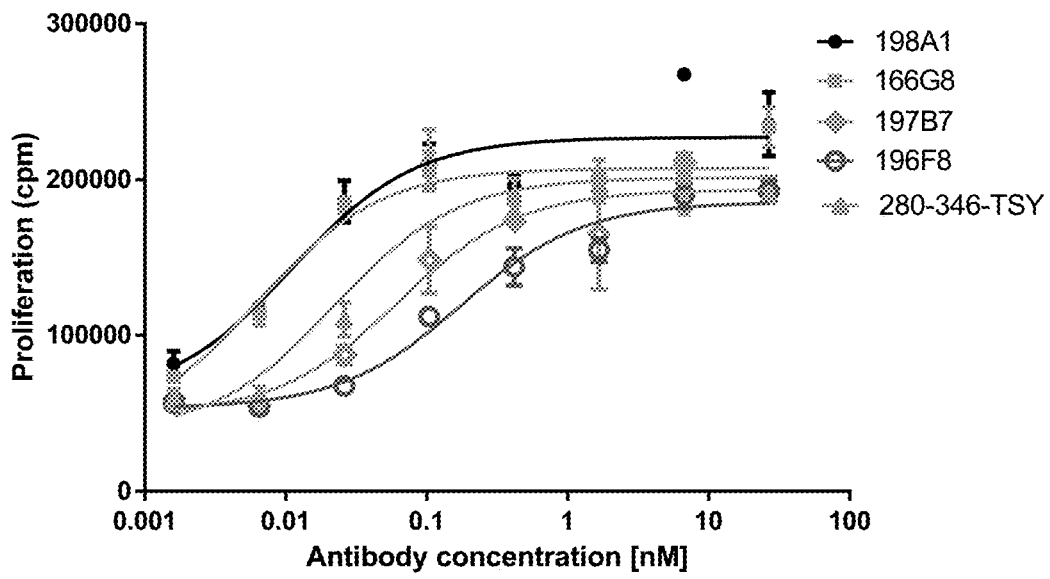
FIGS. 4A-4B show inhibition of IL-22 and IL-20 mediated signalling via IL-22R in cell-based proliferation assays.
Figure 4B:
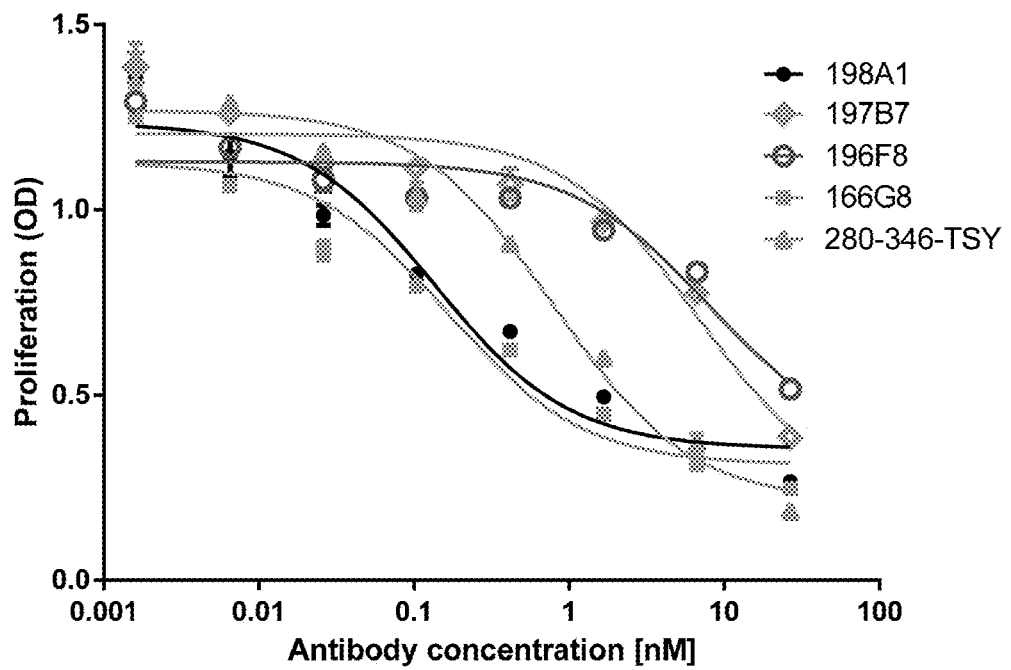

The results of testing various IL22R mAbs against the BW-hIL22R cell line and Baf3-hIL22R/IL20Rb cell line are shown in FIGS. 4A-4B and Table 9. In FIG. 4A, the effects of IL22R neutralizing antibodies in restoring proliferation of the BW-hIL22R cell line can be seen. In FIG. 4B the effects of IL22R neutralizing antibodies in inhibiting IL-20 proliferation of the IL-22R expressing cell line can be seen. The IL22R antibody described in WO2011/061119 (280.346.TSY) was included in the experiments as a benchmark or reference IL-22R antibody.

In addition to the potency on cells, the in vitro binding kinetics and blocking activity of the purified antibodies were measured in Biacore (3000). For affinity measurement, recombinant IL22R was coated onto a Biacore CM5 chip at 200RU using a standard coating protocol (IL22R is injected at 10 µg/ml in Acetate buffer pH 4.5). Antibodies tested at a range of concentrations and prepared in HBSEP buffer at pH 7.4 (Biacore) were injected at 30 µl/min for 60 second and washed with HBSEP buffer at pH 7.4 (Biacore) for 10-20 min. The obtained sensograms were analyzed with the BIA evaluation software and kinetics were determined using standard fitting (Langmuir 1:1 with mass transfer).

For blocking activity using the Biacore 3000, recombinant IL22 (RnD System) was coated at 2000RU onto a CM5 Chip. The antigen binding domains (purified IgG, purified Fabs or periplasmic extract containing the Fabs) were pre-incubated with recombinant human IL22R (concentration between 0.2 and 1 µg) before injection into the hIL22 coated channel. Detection of binding (IL22R:IL22) indicated that the antigen binding domain was not competing while when no binding (IL22R:IL22) was detected, this indicated that the antigen binding domain was blocking the IL22:IL22R interaction in vitro. The results of the Biacore and proliferation assays are summarized in Table 9 below.

TABLE 9

Summary of the characteristics of a pane of hIL22R antibodies

| VH Family | Clone | Binding to hIL22R in Biacore | | | Blocking | Potency in proliferation assay IC50 (pM) | |
|---|---|---|---|---|---|---|---|
| | | Ka (1/Ms) | Kd (1/s) (off-rate) | KD (M) | IL22-IL22R Biacore | BW human IL22R | BaF3 mouse IL22R |
| 1 | 170B2 | 7.6E+05 | 9.3E−05 | 1.2E−10 | Yes | 60-200* | — |
| 1 | 170D6 | | 2.2E−04 | | Yes | 3,830 | — |
| 2 | 160E2 | | 6E−05 | | No | — | 1,406 |
| 3 | 158C4 | | 6E−04 | | No | — | — |
| 4 | 157A2 | 3.9E+05 | 1.1E−03 | 2.8E−09 | Yes | 80-130* | — |
| 4 | 171A1 | | 7.4E−04 | | | 3,320 | |
| 5 | 159B8 | | 2E−03 | | Yes | 100-200* | — |
| 5 | 166G8 | 9.2E+06 | 2.0E−04 | 2.2E−11 | Yes | 10-50* | — |
| 5 | 169C1 | | | | Yes | 35-90* | (—) |
| 6 | 157G8 | | 5.4E−05 | | Yes | 1,174/2,090 | — |
| 7 | 157B8 | | 3.4E−05 | | No | 19,000 | 38,000 |
| 8 | 158H4 | | 3E−05 | | No | 500-1,600* | 5-20 × $10^3$* |
| 11 | 165B8 | | 3.1E−06 | | No | — | — |
| 19 | 169G4 | 5.4E+05 | 3.1E−03 | 5.7E−09 | No | 1,489 | |
| 20 | 172C9 | | | | No | — | — |
| 22 | 166D8 | | 3.2E−03 | | No | 74,000 | — |
| Benchmark | 280.346.TSY | 2.7E+05 | 6.4E−05 | 2.4E−10 | Yes | 20-110* | 10-50* |

*range observed over several experiments

IL22R antibodies 157A2 and 166G8 display picomolar potency.

Example 7 Species Cross-Reactivity of IL-22R mAbs

The IL22R mAbs were tested for species cross-reactivity against murine IL-22R and non-human primate IL-22R.

The cDNA for cynomolgus IL22R was not available and had to be extracted from cynomolgus cDNA libraries. Primers were designed based on the NCBI public database. Several sequences for cynoIL22R ECD were available from public databases (Genbank, NCBI) and contained either insertion, deletion or both (see FIGS. 5A-5B). The uncertainty regarding the true cynomolgus IL22R sequence justified the cloning from cyno cDNA.

The cynomolgus IL22R ECD was amplified by PCR from a cDNA library and cloned in frame downstream of the IgGkappa signal peptide and upstream of the human Fc in the pUPE vector. Although the cDNA used was derived from cynomolgus, sequencing of several clones showed that the rhesus IL22R was also cloned. Rhesus IL22R-ECD was characterized by the absence of the deletion and insertion found in the cynomolgus (boxed in FIGS. 5A-5B) and by 2 amino acid differences between rhesus and cyno IL22R (in bold in FIGS. 5A-5B).

After production and purification of the cyIL22R-Fc and the rhIL22R-Fc, the binding specificity to cynomolgus, rhesus and mouse IL22R ECD of all the antibodies from primary selection was tested in ELISA and by SPR (Biacore). Monomeric mouse IL22R was purchased from R&D Systems (cat 4248-MR). The results are summarized in Table 10.

TABLE 10

Species cross-reactivity of IL-22R mAbs

| VH Family | Clone | Binding to IL22R from: | | | |
|---|---|---|---|---|---|
| | | human | mouse | cyno | rhesus |
| 1 | 170B2 | Yes | No | nt | nt |
| 1 | 170D6 | Yes | No | nt | nt |
| 2 | 160E2 | Yes | Moderate | Yes | Yes |
| 3 | 158C4 | Yes | No | Yes | Yes |
| 4 | 157A2 | Yes | No | Yes | Yes |
| 5 | 159B8 | Yes | No | No | Weak |
| 5 | 166G8 | Yes | No | No | Yes |
| 5 | 169C1 | Yes | No | No | Weak |
| 6 | 157G8 | Yes | Moderate | Yes | Moderate |
| 7 | 157B8 | Yes | No | Yes | Yes |
| 8 | 158H4 | Yes | Moderate | Yes | Yes |
| 8 | 205A5 | Yes | Moderate | Yes | Yes |
| 11 | 165B8 | Yes | Moderate | Moderate | Moderate |
| 19 | 169G4 | Yes | No | Yes | Yes |
| 20 | 172C9 | Yes | Moderate | Yes | Yes |
| 22 | 166D8 | Yes | No | Yes | Yes |
| Benchmark | 280.346.TSY | Yes | Yes | Yes | Yes | nt = not tested

Example 8 Epitope Mapping

Two methods were employed to identify and compare the epitopes bound by the IL22R mAbs: competitive ELISA and FACS.

8.1 Epitope Mapping Using Competitive ELISA

The epitopes recognized by the antibodies were compared to each other by competitive ELISA. At least one mAb representative of each VH family was coated in a Maxisorp plate. Subsequently, biotinylated human IL22R was added in the presence of a large excess of the mAbs to test. The binding of biotinylated IL22R to the coated antibody was detected using HRP-conjugated streptavidin. When biotinylated IL22R was not detected, meaning that the soluble mAb prevented binding to the coated mAb, it was determined that both mAbs bind to the same epitope, or have an overlapping epitope. The epitope mapping was further refined by using Fabs instead of the mAbs. The smaller Fab fragment allowed for some distinction of very close epitopes.

Figure 6:
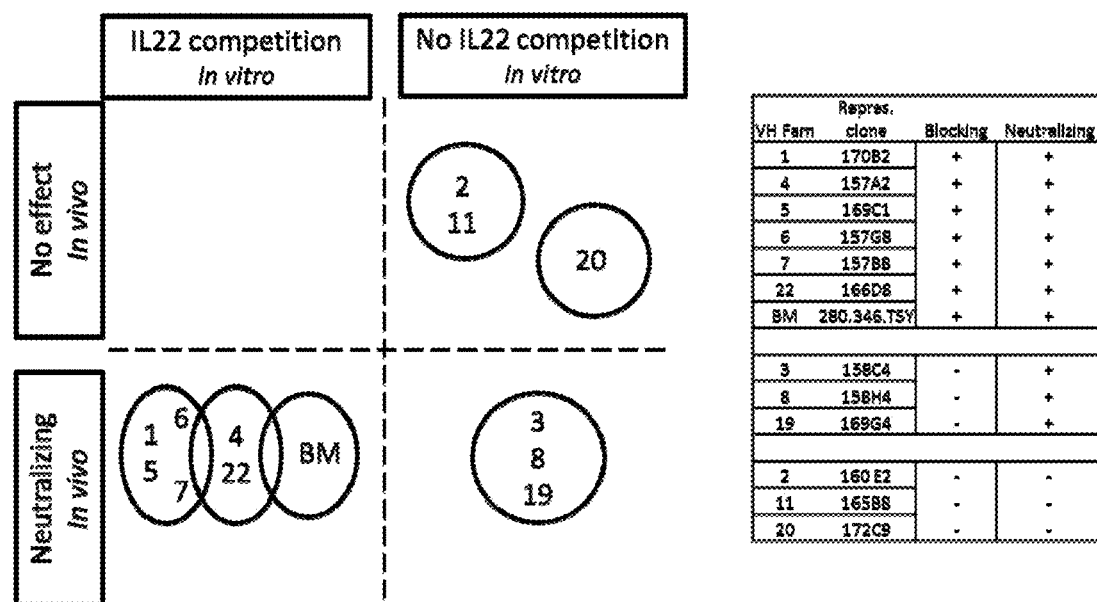
FIG. 6 shows the results of the competitive ELISA experiments carried out to map the epitopes of IL-22R mAbs. A variety of epitopes were identified for antibodies of VH families 1-8, 10, 11, 19 and 22. The epitopes were grouped according to whether the antibodies (i) blocked IL-22 binding in vitro and neutralised IL-22 signalling in a cell-based assay (bottom left quadrant); (ii) blocked IL-22 binding in vitro but had no neutralising activity in the cell-based assay (top right quandrant); or (iii) did not block IL-22 binding in vitro but did have neutralising activity in a cell-based assay (bottom right quadrant).

A variety of epitopes were identified for antibodies of VH families 1-8, 10, 11, 19 and 22. The epitope mapping shows a very broad epitope coverage for such a small protein (25 kDa). As shown in FIG. 6, the epitopes were grouped according to whether the antibodies (i) blocked IL-22 binding in vitro and neutralised IL-22 signalling in a cell-based assay (bottom left quadrant); (ii) blocked IL-22 binding in vitro but had no neutralising activity (top right quandrant); or (iii) did not block IL-22 binding in vitro but did have neutralising activity in a cell-based assay (bottom right quadrant). Six overlapping but distinguishable epitopes were found to be blocking and neutralising (see bottom left quadrant) and out of these six epitopes, two (mAbs from family 4 and 22) had an overlapping epitope with the benchmark antibody (280.346.TSY, see patent application WO2011/061119). The epitope was not identical to the benchmark since these mAbs (from family 4 and 22) were able to compete also with all the mAbs from families 1, 5, 6 and 7 even though these were not able to compete the Benchmark antibody. Taken together these data suggest 2 distinct epitope groups, one formed by the Benchmark and one formed by mAbs from families 1, 5, 6 and 7, and a third group (mAbs from fam 4 and 22) which overlap with both groups (FIG. 6).

As shown in the top right-hand quadrant of FIG. 6, 3 antibodies were identified that bind to IL22R but do not block IL22 binding or neutralize activity in vivo. These antibodies likely bind regions of IL22R not involved in ligand binding or activation of signaling and could be used for pure detection. The 3 antibodies shown in the bottom right-hand quadrant of FIG. 6 are unusual in that they neutralize IL22R activity in vivo but do not block IL22 in vitro, suggesting a new functional epitope and unexpected mode of action.

8.2 Epitope Mapping Using FACS Analysis

Figure 7A:
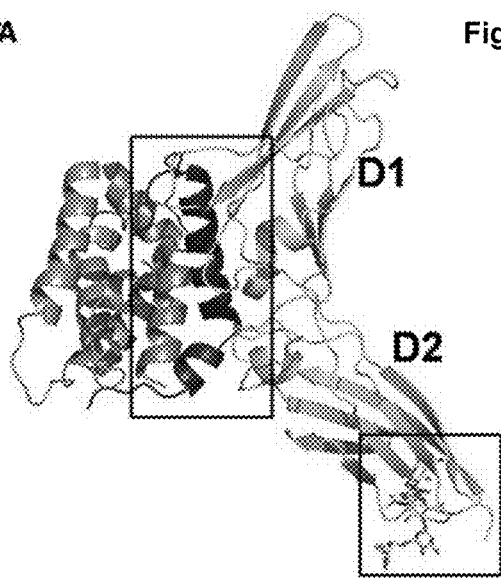
FIGS. 7A-7B show the crystal structure of IL-22R in complex with IL-22.
Figure 7B:
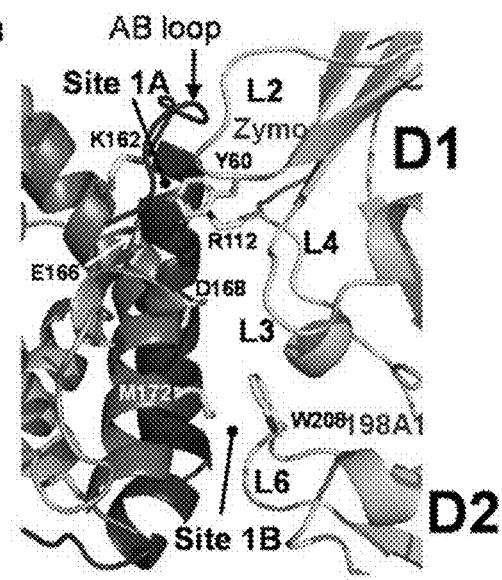

Jones et al. (Structure 16(9): 1333-1344 (2008)) reports the structure of IL-22 bound to the extracellular domain of IL22R1. In this paper, the authors show that the two IL22R domains, called D1 and D2, interact with the IL-22 ligand at site 1A and site 1B, respectively (see FIGS. 7A-7B 7). Two key residues in IL22R-D1 involved in the direct interaction with the site 1A of IL22 are lysine 58 (K58) and tyrosine 60 (Y60). Tryptophan 208 (W208) of IL22R-D2 is directly involved in the interaction with the site 1B of IL22 (see FIGS. 7A-7B).

The binding of IL22R antibodies and of the benchmark antibody (280.346.TSY) to BW cells over-expressing various IL22R mutants was tested. The IL22R mutants have mutations of amino acids known to be involved in the IL-22/IL22R interaction. In this setup, the antibodies were biotinylated, added to the cells and binding of the antibody to IL22R was detected with labeled streptavidin by Flow cytometry (FACS). Table 11 summarizes the results obtained.

TABLE 11

Antibody binding to cells expressing IL22R mutants

| | | | | | hIL-22R mutants | | | | | |
|---|---|---|---|---|---|---|---|---|---|---|
| | VH Fam | A209D | W208A | T207A | K58A | Y60A | R112A | T89A | E90A | Q117A | D162A |
| | | | | | IL22 binding site | | | | | |
| | | 1B | 1B | 1B | 1A | 1A | 1A | 1A | 1A | 1A/B | 1B |
| AMR22 | | + | + | + | X | X | X | + | + | + | + |
| 280.346.TSY | | + | + | + | X | X | + | + | + | + | + |
| 198A1 | 5 | X | + | + | + | + | + | + | + | + | + |
| 166G8 | 5 | + | + | + | + | + | + | + | + | + | + |
| 197B7 | 1 | + | + | + | + | + | + | + | + | + | + |
| 196F8 | 1 | + | + | + | + | + | + | + | + | + | + |
| 158H4 | 8 | + | + | + | + | + | + | + | + | + | + |
| 169G4 | 19 | + | + | + | + | + | + | + | + | + | + |

+ = binding; X = mutation in IL22R results in loss of antibody binding.

The FACs results clearly show that the benchmark antibody 280.346.TSY interacts with residues of the D1 domain (K58 and Y60). The same is true for a second control IL-22R antibody, AMR22, although the epitope is not completely the same, since the R112A mutation affects AMR22 binding. As expected from the ELISA epitope mapping showing that certain llama antibodies do not compete with 280.346.TSY, the other antibodies tested were not affected by the mutations affecting the binding of 280.346.TSY to IL22R. This confirmed that the antibodies target another epitope, possibly including residues in the D2 domain. Indeed, the A209D mutation in the D2 domain of IL22R abrogated binding of 198A1 confirming that 198A1 and the antibody from family 5 bind to the D2 domain of IL22R (see FIG. 7B).

Surprisingly antibody 166G8, which shares exactly the same VH as 198A1, but has a different VL, is not affected by the A209D mutation suggesting that the VL is involved in the interaction. Presumably, the VL of 166G8 allows for a large residue at position 209, while the VL of 198A1 does not. This hypothesis is confirmed by their binding specificity to rhesus IL22R. In rhesus, IL22R has a serine at position 209. Since 166G8 allows for a large amino acid at that position, it can bind rhesus IL22R while 198A1 is not able to bind rhIL22R since it does not allow large residues.

Example 9 Neutralization of IL20 and IL24 Signalling in a Cell-Based Assay

IL22R antibodies were tested for their ability to block IL-20 and IL-24 dependent signaling in cells co-expressing IL22R and IL20Rb. A mechanistic difference exists between the IL-22, IL-20 and IL-24 dependent receptor activation. It is believed that IL-22 induces signaling by first binding to the IL22R, triggering the co-receptor IL10R2 recruitment and activation of the trimeric complex. For IL-20, it is believed that this cytokine binds the co-receptor first (IL20R2) before recruiting IL22R and activation of the trimeric complex. Finally for IL-24, it is not clear how the receptor complex is recruited and activated, nor is it clear where IL-24 binds.

9.1 IL-24 Signaling

Several cell lines were used to test the IL-24 dependent signaling, Baf3-hIL22R/20R2 or Baf3-mIL22R/20R2. IL-24 induced proliferation of these cell lines with a significant window as measured by the hexosaminidase level (read-out used to count cells) ranging from OD 0.17 to 1.5 for the Baf3-hIL22R/20Rb cells and ranging from 0.15 to 0.8 for the Baf3-mIL22R/20Rb cells. None of the antibodies tested had an effect on the IL-24 induced proliferation. These results suggest that either IL-24 has a completely different mode of IL22R activation by binding to a site very distinct to IL22 and IL-20, or that IL22R is not involved in the IL-24 signaling in the cell line tested (and the assay is not predictive of neutralizing activity).

9.2 IL-20 Signaling

Figure 8:
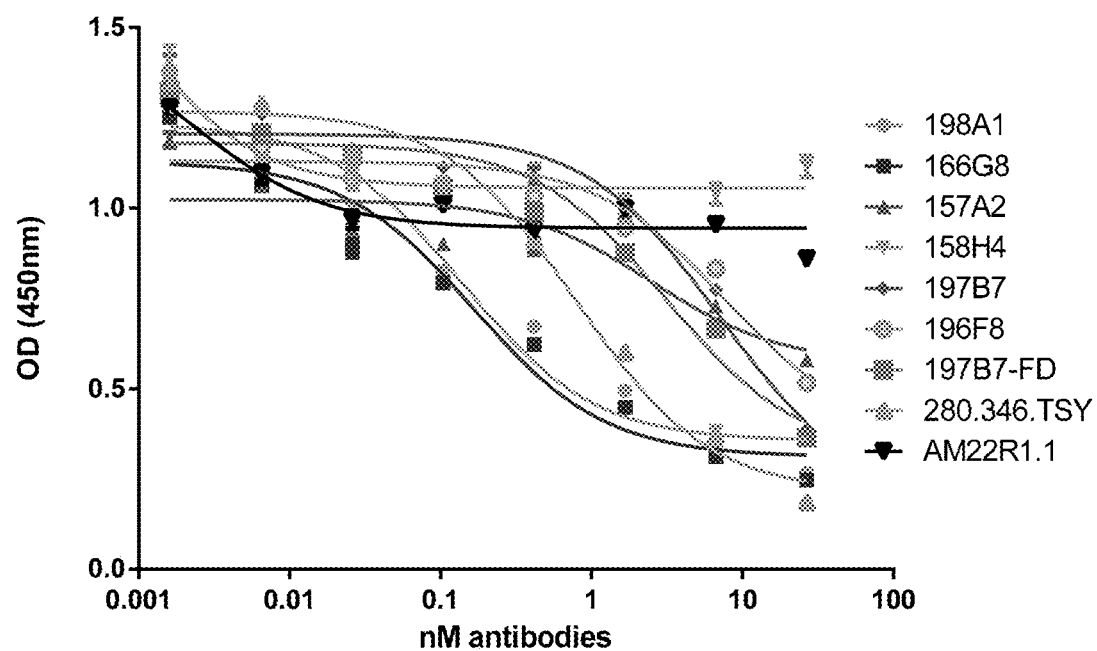
FIG. 8 shows the inhibition of IL-20 mediated signalling via IL-22R in a cell-based proliferation assay. Various IL-22R mAbs were tested for their ability to inhibit the IL-20 induced proliferation of Baf3-hIL-22R/IL20Rb cells.

Baf3-hIL22R/IL20Rb cell line is derived from the Baf3 cell line but co-expresses hIL22R with hIL20Rβ allowing the cells to proliferate in the presence of IL-20. Antibody neutralizing the hIL22R will block the proliferation of cell stimulated with IL-20. Results produced testing llama antibodies alongside the 280.346.TSY and AMR22 benchmark antibodies are shown in FIG. 8.

The IL-20 proliferation on Baf3-hIL22R/IL20Rb was tested in parallel with the IL-22 proliferation assay of BW-hIL22R, allowing a good comparison between the two cytokines. The results of up to three independent experiments are shown in Table 12.

TABLE 12

Potency of the antibodies in blocking IL-22 and IL-20 signaling via IL22R

| | VH family | IC50 blocking IL-22 (pM) | IC50 blocking IL-20 (pM) |
|---|---|---|---|
| 166G8 | 5 | 6-84 | 160-170 |
| 198A1 | 5cs | 10-80 | 85-140 |
| 197B7 | 1 | 61-370 | 1,600-6,960 |
| 157A2 | 4 | 131-540 | 184-545 |
| 218A7 | 4 | 360 | nt |
| 158H4 | 8 | 1600 | nc |
| 205A5 | 8cs | 500-1,200 | nc |
| AMR22 | Benchmark | 715-5,000 | 470 (n = 1) |
| 280.346.TSY | Benchmark | 22-250 | 280-800 |

*Range observed over up to three experiments (2250, 2292, 2301 for IL-20 and 2253, 2292, 2301, 2428 for IL-22);
nc: not competing;
nt: not tested;
cs: chain shuffled It can be concluded that all the antibodies from families #1, #4 and #5 were able to block both IL-20 and IL-22. It is difficult to compare the potency between the IL-22 and IL-20-stimulated proliferation because of the difference in sensitivity, which depends on the cytokine concentration, receptor number and intracellular biological variation. However, most antibodies were found to be more potent in blocking IL-22 signaling compared to blocking that of IL-20. The interesting exception was 157A2, which has the same potency to block IL-22 and IL-20.

Example 10 Selection of Lead Antibodies and Germlining

The affinity of the most interesting antibodies (neutralizing IL22 signaling) was further improved by light chain shuffling. During light chain shuffling the VHCH1 of the selected antibody is combined with the library of light chain from the same llama from which the VHCH was found. Several rounds of off-rate phage display selection are then performed to identify the VHCH:VLCL pairs which have the best affinity. In the case of antibody 166G8, several clones with improved binding kinetics were found including 198A1, but unfortunately, this clone lost most of its rhesus cross-reactivity and therefore 166G8 remained the most attractive candidate of family #5 for development. In the case of 157A2 (from family #4), several Fab (e.g. 218A7) were identified with improved affinity as compared to 157A2. The following antibodies were taken forward for further development. These antibodies were selected based on potency, species cross-reactivity and epitope or mode of action.

218A7 (an improved variant of 157A2, family #4)—this antibody was found to have very good potency against IL-22 and IL-20 (sub nM), is cross-reactive with non-human primate IL22R but is not cross-reactive with the murine IL22R. 157A2 was found to have an epitope on IL22R distinct but overlapping with the 280.346.TSY benchmark antibody.

166G8 (family #5)—this antibody was found to have high potency (low pM) and has some species cross reactivity, since it binds to the rhesus IL22R (but not cynomolgus, nor murine IL22R).

The characteristics of the IL22R antibodies taken forward are summarized in Table 13 below.

TABLE 13

Characteristics of the llama IL22R antibodies selected for germlining

| | VH Family | Cross-reactivity | | | | Potency | | Relative potency IL-22 v IL-20 | Epitope IL22R |
|---|---|---|---|---|---|---|---|---|---|
| | | h | cyno | rh | m | IL-22 (pM) | IL-20 (pM) | | |
| 157A2 | 4 | +++ | +++ | +++ | — | 131-570 | 184-545 | 1.09 | D1/D2 |
| 218A7 | 4 | +++ | +++ | +++ | — | 350-360 | nd | — | D1/D2 |
| 166G8 | 5 | +++ | — | ++ | — | 6-84 | 160-170 | 3.67 | D2 |
| 280.346.TSY | | +++ | +++ | +++ | +++ | 22-250 | 280-800 | 7.5 | D1 | h = human;
cyno = cynomolgusl;
rh = rhesus;
m = mouse

Example 11 Germlining of IL-22R Antibodies 218A7 and 166G8

Germlining was carried out as described in International patent application no. WO2011/080350, the contents of which are incorporated herein in their entirety. The CDRs were mutated to remove potential post-translational modifications together with certain other positions, which found to vary in antibodies from the same VH and VL families with identical paring. The VH and VL domains of the germlined antibodies produced from llama antibodies 218A7 and 166G8 were assessed for their identity with human sequences. A comparison was also made with the benchmark antibody 280.346.TSY. The results are shown in Table 14 below.

TABLE 14

Human identity of germlined IL-22R antibodies produced from 218A7 and 166G8

| | Name of the clone | % identity for VH | % identity for VL | % identity for VH + VL | Off-rate for human IL-22R1* | Off-rate for rhesus IL-22R1* |
|---|---|---|---|---|---|---|
| | 166G8 | 88.5 | 84.8 | 86.7 | 1.22E−0.3 | 2.22E−02 |
| 22 | 224C7 | 93.1 | 93.7 | 93.4 | 4.19E−04 | 2.20E−02 |
| 6 | 224C6 | 94.3 | 93.7 | 94.0 | 4.34E−04 | 1.85E−02 |
| 21 | 224A6 | 93.1 | 93.7 | 93.4 | 4.41E−04 | 4.68E−0.3 |
| 14 | 224C4 | 92.0 | 94.9 | 93.5 | 4.50E−04 | 4.51E−0.3 |
| 16 | 224G10 | 92.0 | 94.9 | 93.5 | 4.71E−04 | 3.75E−0.3 |
| 15 | 224E8 | 92.0 | 94.9 | 93.5 | 4.81E−04 | 4.51E−0.3 |
| 1 | 223G5 | 93.1 | 97.4 | 95.3 | 5.29E−04 | 5.84E−0.3 |
| 20 | 223D3 | 93.1 | 93.7 | 93.4 | 5.73E−04 | 2.01E−0.3 |
| 2 | 223C4 | 94.3 | 96.2 | 95.3 | 5.74E−04 | 6.27E−0.3 |
| 11 | 223A6 | 90.8 | 96.2 | 93.5 | 5.79E−04 | 2.58E−0.3 |

TABLE 14-continued

Human identity of germlined IL-22R antibodies produced from 218A7 and 166G8

| | Name of the clone | % identity for VH | % identity for VL | % identity for VH + VL | Off-rate for human IL-22R1* | Off-rate for rhesus IL-22R1* |
|---|---|---|---|---|---|---|
| 13 | 223G1 | 92.0 | 94.9 | 93.5 | 5.96E−04 | 5.05E−0.3 |
| 8 | 226B9 | 95.4 | 92.4 | 93.9 | 7.14E−04 | 4.65E−0.3 |
| 3 | 225A5 | 93.1 | 96.2 | 94.7 | 1.14E−0.3 | 1.55E−02 |
| 5 | 227C5 | 93.1 | 94.9 | 94.0 | 1.25E−0.3 | 4.98E−0.3 |
| 17 | 227G10 | 92.0 | 94.9 | 93.5 | 1.25E−0.3 | 2.73E−0.3 |
| 19 | 225G7 | 92.0 | 94.9 | 93.5 | 1.29E−0.3 | 4.27E−0.3 |
| 18 | 225E5 | 92.0 | 94.9 | 93.5 | 1.35E−0.3 | 1.67E−0.3 |
| 12 | 225A4 | 90.8 | 96.2 | 93.5 | 1.42E−0.3 | 4.21E−0.3 |
| 9 | 225A10 | 95.4 | 92.4 | 93.9 | 1.55E−0.3 | 1.07E−02 |
| 7 | 225D8 | 94.3 | 93.7 | 94.0 | 1.64E−0.3 | 5.11E−0.3 |
| 23 | 225G4 | 93.1 | 93.7 | 93.4 | 1.74E−0.3 | 3.75E−0.3 |
| 10 | 225C6 | 95.3 | 92.4 | 93.9 | 1.76E−0.3 | 2.63E−0.3 |
| 4 | 225B2 | 94.3 | 94.9 | 94.6 | 2.78E−0.3 | 4.55E−0.3 |
| | 218A7 | 95.4 | 91.1 | 95.4 | 8.10E−04 | 9.70E−04 |
| 13 | 230C9 | 100 | 96.2 | 98.1 | 3.52E−04 | 4.36E−04 |
| 10 | 230B7 | 98.9 | 97.5 | 98.2 | 3.77E−04 | 8.17E−04 |
| 19 | 229B4 | 98.9 | 96.2 | 97.6 | 3.81E−04 | 4.79E−04 |
| 1 | 230H2 | 100 | 98.7 | 99.4 | 4.01E−04 | 1.08E−0.3 |
| 18 | 228F9 | 97.7 | 97.5 | 97.6 | 4.01E−04 | 4.34E−04 |
| 14 | 228C9 | 100 | 96.2 | 98.1 | 4.08E−04 | 4.72E−04 |
| 12 | 232G6 | 100 | 96.2 | 98.1 | 4.14E−04 | 1.27E−0.3 |
| 11 | 232F5 | 100 | 96.2 | 98.1 | 4.24E−04 | 1.27E−0.3 |
| 5 | 231C11 | 98.9 | 97.5 | 98.2 | 4.30E−04 | 1.32E−0.3 |
| 6 | 231E12 | 98.9 | 97.5 | 98.2 | 4.35E−04 | 1.33E−0.3 |
| 3 | 228F3 | 97.7 | 98.7 | 98.2 | 4.39E−04 | 1.25E−0.3 |
| 2 | 230D5 | 98.9 | 98.7 | 98.8 | 4.45E−04 | 1.32E−0.3 |
| 4 | 231B11 | 98.9 | 97.5 | 98.2 | 4.55E−04 | 1.32E−0.3 |
| 8 | 229E6 | 98.9 | 97.5 | 98.2 | 4.59E−04 | 5.41E−04 |
| 20 | 229D9 | 100 | 94.9 | 97.5 | 4.69E−04 | 6.84E−04 |
| 16 | 229G1 | 97.7 | 97.5 | 97.6 | 4.77E−04 | 5.08E−0.3 |
| 7 | 231F12 | 98.9 | 97.5 | 98.2 | 5.30E−04 | 1.35E−0.3 |
| 17 | 228A4 | 97.7 | 97.5 | 97.6 | 5.95E−04 | 1.97E−0.3 |
| 15 | 231A8 | 97.7 | 97.5 | 97.6 | 1.48E−0.3 | 2.85E−0.3 |
| 9 | 229G2 | 98.9 | 97.5 | 98.2 | 1.86E−0.3 | 3.30E−0.3 |
| | 280.346.TSY | 88.5% | 100% | 94.3% | — | — |

*Determined for Fab fragments

Antibody 230C9 was selected as a germlined variant of antibody 218A7, and antibody 223G5 was selected as a germlined variant of antibody 166G8. The VH and VL domain sequences of antibodies 218A7, 230C9 and 223G5 are shown in Tables 15-19 below. (The sequences of 166G8 are shown in Tables 4-7 above.)

TABLE 15

Framework regions and CDR sequences for VH domains of 218A7, 230C9 and 223G5

| Clone | FR1 | SEQ ID NO. | CDR1 | SEQ ID NO. | FR2 | SEQ ID NO. | CDR2 | SEQ ID NO. | FR3 | SEQ ID NO. | CDR3 | SEQ ID NO. | FR4 | SEQ ID NO. |
|---|---|---|---|---|---|---|---|---|---|---|---|---|---|---|
| 218A7 | QVQLVESGGGLVQPGGSLRLSCAASGFTFS | 1 | SYDMS | 2 | WVRQAPGKGLEWVS | 3 | SIYNDGSNTAYSDSVKG | 4 | RFTISRDNAKNTLYLQMNSLKSEDTAVYYCAK | 5 | VGFSGTYYSES | 6 | WGQGTQVTVSS | 7 |
| 230C9 | QVQLVESGGGLVQPGGSLRLSCAASGFTFS | 33 | SYDMN | 34 | WVRQAPGKGLEWVS | 35 | SIYNDASNTAYSDSVKG | 36 | RFTISRDNSKNTLYLQMNSLRAEDTAVYYCAK | 37 | VGFSGTYYSES | 6 | WGQGTLVTVSS | 38 |
| 223G5 | QVQLVESGGGLVQPGGSLRLSCAASGFTFS | 39 | SYFMS | 9 | WVRQAPGKGPEWVS | 40 | GIHISGGITYYTDSVKG | 41 | RFTISRDNAKNTLYLQMNSLRAEDTAVYYCVT | 42 | PPGPFKAHYNGAKY | 43 | WGKGTLVTVSS | 44 |

TABLE 16

Framework regions and CDR sequences for VL domains of 218A7, 230C9 and 223G5

| Clone | FR1 | SEQ ID NO. | CDR1 | SEQ ID NO. | FR2 | SEQ ID NO. | CDR2 | SEQ ID NO. | FR3 | SEQ ID NO. | CDR3 | SEQ ID NO. | FR4 | SEQ ID NO. |
|---|---|---|---|---|---|---|---|---|---|---|---|---|---|---|
| 218A7 | LPVLTQPSAVSVSLGQTARITC | 45 | QGGYYAH | 16 | WYQQKPGQAPVLVIY | 46 | GQNNRPS | 47 | NTATLTISGAQAEDEAEYYC | 48 | QSGSSSANAV | 20 | FGGGTKLTVL | 49 |
| 230C9 | SYELTQPSSVSVALGQTARITC | 50 | QGGYYAH | 16 | VVYQQKPGQAPVLVIY | 51 | GQNNRPS | 47 | NTATLTISRAQAEDEADYYC | 53 | QSGSSSSNAV | 54 | FGGGTKLTVL | 55 |
| 223G5 | QSALTQPPSVSGSPGQSVTISC | 56 | TGTSSDIGSYNYVS | 57 | WYQQLPGKAPKLLIY | 58 | EVNKRSS | 59 | NTASLTISGLQAEDEADYYC | 60 | ASYRLYADYV | 27 | FGGGTQLTVL | 61 |

TABLE 17

Variable domain sequences for 218A7, 230C9, 223G5

| Clone | VH | SEQ ID NO. | VL | SEQ ID NO. |
|---|---|---|---|---|
| 218A7 | QVQLVESGGGLVQPGGSLRLSCAASGFTFSSYDMSWVRQAPGKGLEWVSSIYNDGSNTAYSDSVKGRFTISRDNAKNTLYLQMNSLKSEDTAVYYCAKVGFSGTYYSESWGQGTQVTVSS | 29 | LPVLTQPSAVSVSLGQTARITCQGGYYAHWYQQKPGQAPVLVIYGQNNRPSGIPERFSGSGAGNTATLTISGAQAEDEAEYYCQSGSSSANAVFGGGTKLTVL | 62 |
| 230C9 | QVQLVESGGGLVQPGGSLRLSCAASGFTFSSYDMNWVRQAPGKGLEWVSSIYNDASNTAYSDSVKGRFTISRDNSKNTLYLQMNSLRAEDTAVYYCAKVGFSGTYYSESWGQGTLVTVSS | 63 | SYELTQPSSVSVALGQTARITCQGGYYAHWYQQKPGQAPVLVIYGQNNRPSGIPERFSGSGAGNTATLTISRAQAEDEADYYCQSGSSSSNAVFGGGTKLTVL | 64 |
| 223G5 | QVQLVESGGGLVQPGGSLRLSCAASGFTFSSYFMSWVRQAPGKGPEWVSGIHISGGITYYTDSVKGRFTISRDNAKNTLYLQMNSLRAEDTAVYYCVTPPGPFKAHYNGAKYWGKGTLVTVSS | 65 | QSALTQPPSVSGSPGQSVTISCTGTSSDIGSYNYVSWYQQLPGKAPKLLIYEVNKRSSGVPDRFSGSKSGNTASLTISGLQAEDEADYYCASYRLYADYVFGGGTQLTVL | 66 |

TABLE 18

Heavy chain and light chain sequences for 230C9 and 223G5

| Clone | Heavy chain | SEQ ID NO. | Light chain | SEQ ID NO. |
|---|---|---|---|---|
| 230C9 | QVQLVESGGGLVQPGGSLRLSCAASGFTFSSYDMNWVRQAPGKGLEWVSSIYNDASNTAYSDSVKGRFTISRDNSKNTLYLQMNSLRAEDTAVYYCAKVGFSGTYYSESWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYQSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 67 | SYELTQPSSVSVALGQTARITCQGGYYAHWYQQKPGQAPVLVIYGQNNRPSGIPERFSGSGAGNTATLTISRAQAEDEADYYCQSGSSSSNAVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS | 68 |
| 223G5 | QVQLVESGGGLVQPGGSLRLSCAASGFTFSSYFMSWVRQAPGKGPEWVSGIHISGGITYYTDSVKGRFTISRDNAKNTLYLQMNSLRAEDTAVYYCVTPPGPFKAHYNGAKYWGKGTLVTVSSASTKGPSVFPLAPSSKSTSGGTAALGCLVKDYFPEPVTVSWNSGALTSGVHTFPAVLQSSGLYSLSSVVTVPSSSL | 69 | QSALTQPPSVSGSPGQSVTISCTGTSSDIGSYNYVSWYQQLPGKAPKLLIYEVNKRSSGVPDRFSGSKSGNTASLTISGLQAEDEADYYCASYRLYADYVFGGGTQLTVLGQPKAAPSVTLFPPSSEELQANKATLVCLISDFYPGAVTVAWKADSSPVKAGVETTTPSKQSNNKYAASS | 70 |

TABLE 18-continued

Heavy chain and light chain sequences for 230C9 and 223G5

| Clone | Heavy chain | SEQ ID NO. | Light chain | SEQ ID NO. |
|---|---|---|---|---|
| | GTQTYICNVNHKPSNTKVDKKVEPKSCDKTHTCPPCPA PELLGGPSVFLFPPKPKDTLMISRTPEVTCVVVDVSHED PEVKFNWYVDGVEVHNAKTKPREEQYQSTYRVVSVLT VLHQDWLNGKEYKCKVSNKALPAPIEKTISKAKGQPRE PQVYTLPPSRDELTKNQVSLTCLVKGFYPSDIAVEWES NGQPENNYKTTPPVLDSDGSFFLYSKLTVDKSRWQQG NVFSCSVMHEALHNHYTQKSLSLSPGK | | YLSLTPEQWKSHRSYSCQVTHEGSTVEKTVAPTE CS | |

The shaded portions of the sequence represent the constant regions of the heavy and light chains. The "Q" residue shown in bold in the constant region of the heavy chain represents a mutation from "N".

TABLE 19

Polynucleotide sequences encoding the variable domain sequences/heavy chain and light chain sequences for 218A7, 230C9 and 223G5

| Clone | VH domain | SEQ ID NO. | VL domain | SEQ ID NO. |
|---|---|---|---|---|
| 218A7 | CAGGTGCAGCTCGTGGAGTCTGGGGGAGGCTTGGTGCAGC CTGGGGGTTCTCTGAGACTCTCCTGTGCAGCCTCTGGATTCA CCTTCAGTAGCTACGACATGAGCTGGGTCCGCCAGGCTCCA GGGAAGGGGCTGGAGTGGGTGTCCAGTATTTATAATGACG GTAGTAACACAGCCTATTCAGACTCCGTGAAGGGCCGATTC ACCATCTCCAGAGACAACGCCAAGAACACGTTGTATCTGCAA ATGAACAGCTTGAAATCTGAGGACACGGCCGTGTATTACTG TGCAAAAGTTGGCTTTAGTGGTACTTACTACAGTGAATCATG GGGCCAGGGGACCCAGGTCACCGTGTCCTCA | 76 | CTGCCTGTGCTGACTCAGCCCTCCGCGGTGTCCGTGTCT TTGGGACAGACGGCCAGGATCACCTGCCAAGGGGGCT ATTATGCTCACTGGTACCAGCAGAAGCCAGGCCAGGCC CCTGTGCTGGTCATCTATGGACAGAATAATAGGCCCTC AGGGATCCCTGAGCGCTTCTCTGGCTCCGGCGCTGGGA ACACAGCCACCCTGACCATCAGCGGGGCCCAGGCTGA GGACGAGGCTGAGTATTACTGTCAGTCAGGAAGCAGT AGTGCTAATGCTGTGTTCGGCGGAGGGACCAAGCTGA CCGTCCTC | 77 |
| 230C9 | CAGGTGCAGCTCGTGGAGTCTGGGGGAGGCTTGGTGC AGCCTGGGGGTTCTCTGAGACTCTCCTGTGCTGCCTCT GGATTCACCTTCAGTAGCTACGACATGAACTGGGTCC GCCAGGCTCCAGGGAAGGGGCTGGAGTGGGTGTCCAG CATTTATAACGACGCAGTAACACAGCCTATTCAGACT CCGTGAAGGGCCGATTCACCATCTCCAGAGACAACTC AAAGAACACGTTGTATCTGCAAATGAACAGCCTGAGA GCTGAGGACACGGCCGTGTATTACTGTGCGAAAGTTG GCTTTAGTGGTACTTACTACAGTGAATCATGGGGCCAG GGGACCCTCGTCACTGTCTCCTCA | 78 | TCCTACGAACTGACTCAGCCCTCCTCGGTGTCCGT GGCGTTGGGACAGACGGCCAGGATCACCTGCCAA GGAGGCTATTATGCACACTGGTACCAGCAGAAGC CAGGCCAGGCCCCTGTGCTGGTCATCTATGGACA GAATAATAGGCCCTCAGGGATCCCTGAGCGCTTC TCTGGCTCCGGCGCTGGGAACACAGCCACCCTGA CAATCAGCCGCGCCCAGGCTGAGGACGAGGCTGA CTATTACTGTCAGTCAGGAAGCAGTAGTTCTAATG CTGTGTTCGGCGGAGGGACCAAGCTGACCGTCCT C | 79 |
| 223G5 | CAGGTGCAGCTCGTGGAGTCTGGGGGCGGCTTGGT GCAGCCTGGGGATTCTCTGAGACTCTCCTGTGCAGC CTCTGGATTCACCTTCAGTAGCTATTTCATGAGCTGG GTCCGCCAGGCTCCAGGAAAGGGGCCCGAGTGGGT CTCAGGTATTCATATTAGTGGTGGTATTACATACTACA CGGACTCCGTGAAGGGCCGATTCACCATCTCCAGAG ACAACGCAAAGAACACGCTGTATCTGCAAATGAACAG CCTGAGAGCTGAGGACACGGCCGTGTATTATTGTGTA ACACCCCCGGGCCCCTTTAAGGCCCATTACAATGGC GCGAAGTACTGGGGCAAAGGGACCCTGGTCACTGTC TCCTCA | 80 | CAGTCTGCCCTGACTCAGCCTCCCTCCGTGTCTGGATCT CCTGGACAGTCTGTCACCATCTCCTGCACTGGAACCAGT AGTGACATTGGGTCCTATAACTATGTCTCCTGGTATCAA CAGCTCCCAGGAAAGGCCCCCAAACTCCTGATCTATGA GGTCAACAAGCGATCCTCAGGGGTCCCTGATCGCTTCT CTGGCTCCAAGTCAGGCAACACGGCCTCCCTGACCATC TCTGGGCTCCAGGCTGAGGACGAGGCTGATTATTACTG TGCCTCATATAGACTGTACGCCGATTATGTGTTCGGCG AGGGACCCAACTGACCGTCCTC | 81 |

Example 12 Characterisation of the Germlined Antibodies 230C9 and 223G5

12.1 Binding Affinity of Germlined mAbs

The affinity of the 230C9 and 223G5 antibodies was measured using SPR (Biacore 300). In brief, 250RU of human IL22R (Biotechne, 2770-LR) was coated onto a CM5 chip using standard methods (EDC coupling of IL22R at a concentration of 2 µg/ml in acetate buffer pH4.5). Then various concentrations of antibody were injected in HBSEP+ buffer (pH 7.4) for 2 minutes. The binding was monitored also during a 10 min washing (HBSEP+).

The affinities calculated using the BIAevaluation software using a Langmuir 1:1 fitting are shown in Table 20 below.

TABLE 20

Binding affinity of germlined antibodies

| | ka (1/Ms) | kd (1/s) | KD (M) |
|---|---|---|---|
| 223G5 | 6.6E+06 | 1.0E−04 | 1.6E−11 |
| 224C4 | 9.3E+06 | 9.8E−05 | 1.1E−11 |
| 230C9 | 6.8E+05 | 8.9E−05 | 1.3E−10 |
| 280.346.TSY | 4.9E+05 | 3.4E−04 | 6.9E−10 |

The antibodies 223G5 and 224C4 (both germlined variants of 166G8) showed very high affinity for IL-22R (10-20 pM) whilst antibody 230C9 had an affinity of 0.13 nM. All of the germlined antibodies displayed higher affinity than the reference antibody 280.346.TSY (0.69 nM)

Because of the potential avidity effect observed when a bivalent molecule is used as a ligand during affinity measurement, a reverse experimental setup was tested. In this set-up, the antibodies were coated to 250RU using standard methods. Monomeric human IL22R was added at different concentrations, and the affinities calculated using the BIAevaluation software using a Langmuir 1:1 fitting are shown in Table 21 below.

TABLE 21

Binding affinity of 230C9 to human IL-22R

|  |  | ka (1/Ms) | kd (1/s) | KD (M) |
|---|---|---|---|---|
| 230C9 | hIL22R | 9.2E+05 | 2.2E−04 | 2.2E−10 |

Unfortunately the antibody 223G5 was inactivated by the coating process and no affinity could be determined using this setup.

The affinity of 230C9 is consistent independent of the setup of the affinity measurement, showing that the low coating used in both conditions is sufficient to reduce any avidity effect.

12.2 Inhibition of IL-22 and IL-20 Dependent IL-22R1 Activation and Signalling

Antibodies 218A7 (not germlined), and 230C9 (the germlined equivalent) were tested alongside other germlined antibodies for their ability to neutralize IL-22 and IL-20-mediated signalling via IL-22R1. Testing was performed using the cell-based proliferation assays described in Examples 6 and 9.

Figure 9A:
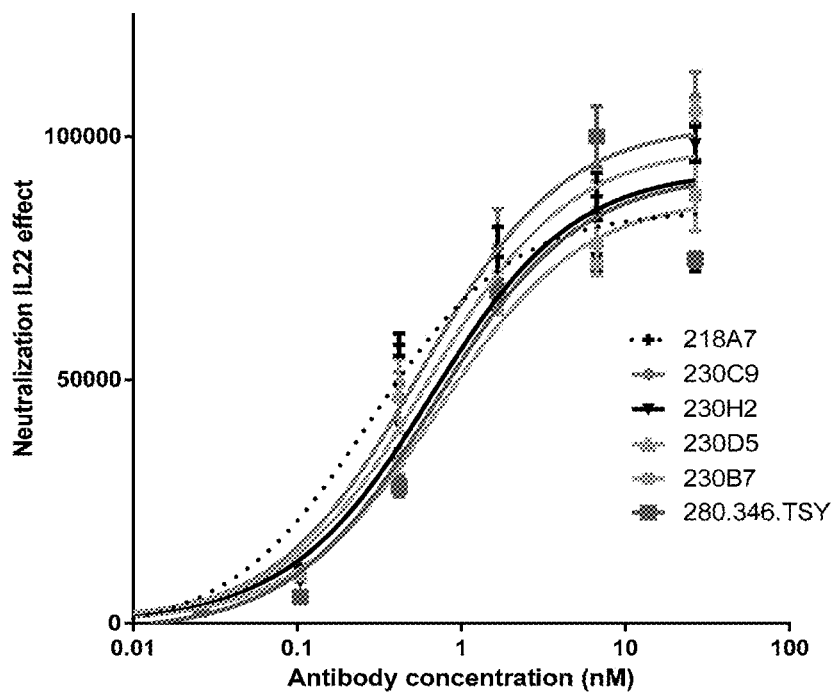
FIG. 9A-9B shows the inhibition of IL-22 and IL-20 mediated signalling via IL-22R in cell-based assays.
Figure 9B:
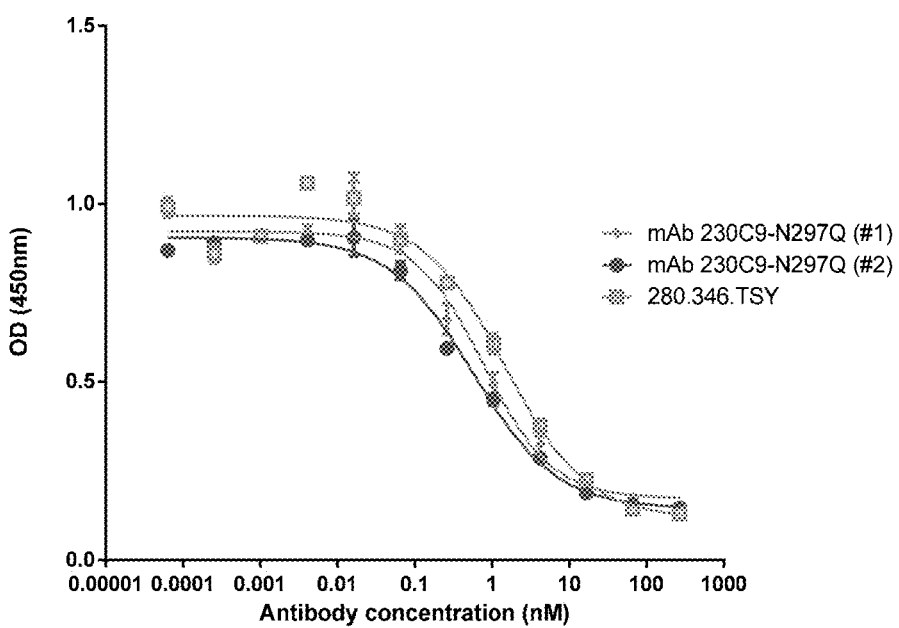

FIG. 9A shows the ability of 218A7 and 230C9 to neutralize IL-22-dependent activation of IL-22R1. FIG. 9B shows the ability of different batches of 230C9 to neutralize IL-20-dependent activation of IL-22R1. The relative potencies of the antibodies tested are shown in Tables 22 and 23 below.

TABLE 22

Potency of the 218A7 and 230C9 antibodies in blocking IL-22 signalling via IL22R (BWhIL22R cell line)

|  | IC50 blocking IL-22 (nM) | Relative potency to 280.346.TSY |
|---|---|---|
| 218A7 | 0.28 | 2.5 |
| 230C9 | 0.56 | 1.2 |
| 230D5 | 0.62 | 1.1 |
| 230H2 | 0.66 | 1.0 |
| 280.346.TSY | 0.69 | 1 |
| 230B7 | 0.73 | 0.95 |

TABLE 23

Potency of the 230C9 antibody in blocking IL-20 signalling via IL22R (Baf3hIL22R/IL20Rb cell line)

|  | IC50 blocking IL-20 (nM) | Relative potency to 280.346.TSY |
|---|---|---|
| 280.346.TSY | 1.487 |  |
| 230C9-N297Q (#1)* | 0.7807 | 1.9 |
| 230C9-N297Q (#2)* | 0.5671 | 2.6 |

*Different purification batches of the 230C9 antibody 12.3 Confirmatory Epitope Mapping Confirmatory epitope mapping for germlined antibodies 230C9 and 223G5 was carried out using FACS analysis, as described in Example 8.2. Antibody 230C9 was found to compete for binding to IL-22R1 with the benchmark antibody 280.346.TSY and also 223G5. Antibody 223G5 did not compete for binding to IL-22R1 with the benchmark antibody 280.346.TSY.

Figure 10:
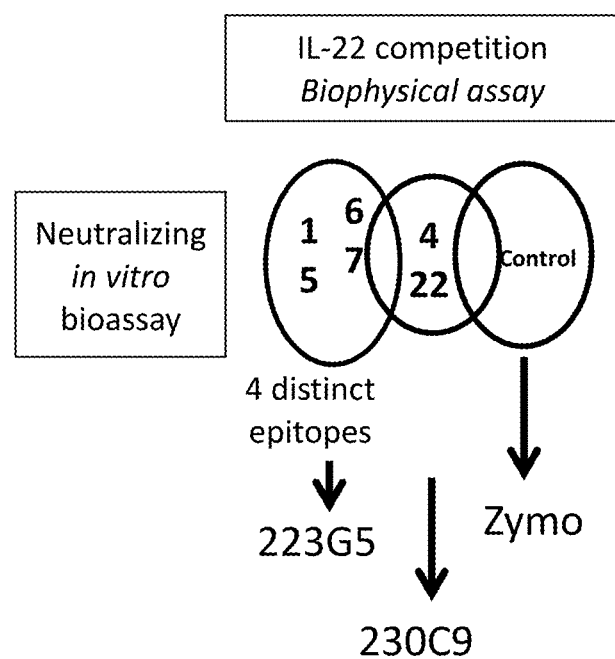
FIG. 10 shows schematically the results of the epitope mapping experiments for the germlined IL-22R antibodies 230C9 and 223G5. NB "Zymo" is equivalent to 280-346-TSY".

The results of the FACS analysis were combined with the results of the proliferation assays described above and the conclusions regarding epitopes are shown in FIG. 10. As indicated, it can be concluded that (i) antibody 230C9 binds to an epitope distinct but overlapping as compared with the epitopes bound by 280.346.TSY; and (ii) antibody 223G5 binds to an epitope distinct from 280.346.TSY.

FACS analysis was also carried out as described in Example 8.2 to study the binding of the germlined antibodies to various IL-22R mutants. The results are shown in Table 24 below.

TABLE 24

Antibody binding to cells expressing IL22R mutants

| BW-hIL-22R mutants | A209D | W208A | Y60A | R112A |
|---|---|---|---|---|
| 280.346.TSY | + | + | X | X |
| 230C9 | + | + | + | +/X |
| 223G5 | X | + | + | + |

+/− = partial recognition of mutant having R112A

These results confirm that antibodies 230C9 and 223G5 bind to an epitope that does not include Y60. The mutation A209D was found to affect binding of 223G5 whereas binding of llama antibody 166G8 was unaffected by this change. This is likely attributable to difficulties in detecting the sensitivity of 166G8 to the A209D mutation (166G8 was tested only once), and possibly attributable to slight changes in the CDR sequences during germlining of 166G8. These data confirm that 280.346.TSY binds to the D1 of IL22R, that 223G5 binds to the D2 of IL22R and that 230C9 has an overlapping but distinct epitope.

12.4 Species Cross-Reactivity of Germlined Antibodies

Antibody 230C9 binds human IL-22R but exhibits no cross-reactivity for IL-22R from mouse, rat and rabbit. This is consistent with 230C9 having a distinct epitope as compared with the benchmark antibody 280.346.TSY—see 12.3 above.

Figure 11:
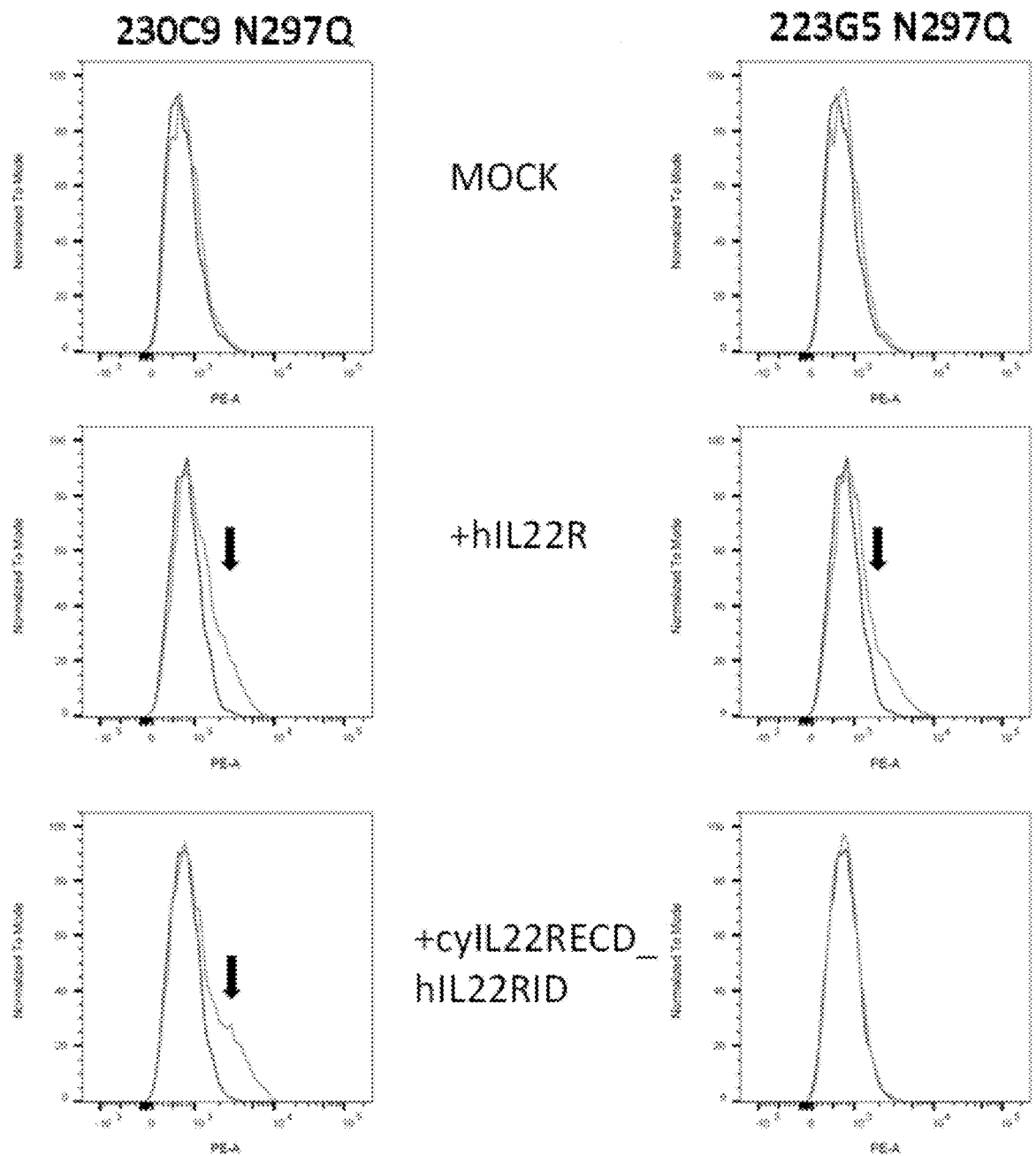
FIG. 11 shows cross-reactivity of the germlined antibodies for human and cynomolgus IL-22R, as determined by FACS analysis. Antibody 230C9 cross-reacts with the human IL-22R and cyno IL-22R (left-hand panels) whereas antibody 223G5 binds to human IL-22R but does not cross-react with cyno IL-22R (right-hand panels).

The capacity of the antibodies to bind cyno-IL22R once expressed on cells was tested by making chimeric constructs of the IL22R extracellular domain (ECD) from the different species fused to the human transmembrane (TM) and human intracellular domains (ID). Although the efficiency of the transient transfection was not large, FACS analysis showed that the 230C9-N297Q antibody, but not the 223G5-N297Q bound to the cynoIL22R_ECD-humanTM_humanICD as observed by the presence of a broader peak on the FACS plot (see FIG. 11 with the arrows indicating the broader peaks).

Furthermore, when the chimeric constructs were also co-transfected with a STAT3-reporter gene into HEK cells, the activity of the IL22R after addition of human IL22 could be measured in the presence or absence of neutralizing antibody. The results presented in Table 25 below show that all the antibodies tested were able to neutralize the human IL22R and that only the primate cross-reactive (230C9 and 280.346.TSY) were able to bind and block the activity of the cyno and rhesus chimeras suggesting that these antibodies will be functional in primate studies.

TABLE 25

| | EC50 (nM) Human ECD | EC50 (nM) Rhesus ECD | EC50 (nM) Cyno ECD |
|---|---|---|---|
| 224C4 | 0.30 | No effect | No effect |
| 230C9 | 0.28 | 0.48 | 0.57 |
| 280.346.TSY | 0.26 | 0.43 | 0.16 |

Cross-reactivity of IL-22R antibodies with human, rhesus and cyno IL-22R 12.5 Immunogenicity Analysis The immunogenicity of the germlined antibodies was assessed using prediction tools. In particular, the presence of potential immunogenic peptides in the variable domains was assessed using the Ionza's Epibase™ platform (DRB-1 score) using the "HLA class II—Caucasian v3.0" settings". This platform analyses the HLA binding specificities of all 10-mer peptides derived from the VH and VL sequences. Profiling was done at the allotype level for 15 DRB1, 6 DRB3/4/5, 12 DQ and 7 DP, i.e. 40 HLA class II receptors in total. Strong and medium binders of DRB1, DRB3/4/5 were identified, as well as the strong binders of DQ and DP epitopes. Epitope counting was done separately for strong and medium affinity DRB1 binders. Peptides binding to multiple allotypes of the same group were counted as one. An approximate score expressing a worst-case immunogenic risk was calculated as follows: Score=Σ (epitope count×allotype frequency). In other words, the number of epitopes affecting a particular HLA allotype is multiplied by the allele frequency of the affected allotype. For a given sequence, the products were summed for all DRB1 allotypes used in the study that are present in 2% or more of the Caucasian population.

The results are shown in Table 26 below.

TABLE 26

DRB1 scores for the germlined IL-22R antibodies as compared with various other commercial antibodies

| | DRB1 Score (VH + VL) | Source |
|---|---|---|
| 230C9 | 555 | Germlined llama |
| 223G5 | 936 | Germlined llama |
| Adalimumab | 830 | Human (phage display) |
| Trastuzumab (Herceptin) | 959 | Humanized |
| Palivizumab (Synagis) | 985 | Humanized |
| Dupilumab | 1124 | Human (Velocimmune) |
| Alemtuzumab (Campath) | 1409 | Humanized |
| Rituximab (Rituxan) | 1769 | Chimeric |
| Infliximab (Remicade) | 1873 | Chimeric |
| Mouse antibody | 3832 | Mouse |

As can be seen from Table 26, antibody 230C9 has a very low DRB1 score, well below other commercial antibodies whilst 223G5 has a low DRB1 score comparable to other commercially available human or humanized antibodies. These data suggest that 230C9 (and 223G5) will have a preferable immunogenicity profile.

Example 13 Pharmacokinetic (PK) Study in Cynomolgus Monkeys of Antibody 230C9-N297Q Pharmacokinetic analysis of antibody clone 230C9 was performed. Two Cynomolgus monkeys were injected intravenously with a single 10 mg/kg dose of antibody for 2 h. Samples were taken at different time points and tested for plasma concentration of mAb by ELISA. Specifically, a microtiterplate (Maxisorb Nunc) was coated with 2 µg/ml recombinant hIL22R (Biotechne; cat 2770-LR) in PBS overnight at 4° C. The plate was washed 3 times with PBS-Tween and blocked for 2 hours with 250 µl PBS-1% casein. After 3 washes with PBS-Tween, the samples were applied. All dilutions were made in 1% pooled plasma (this is a pool from 3 naive cynomolgus monkeys). The samples were allowed to bind for 2 hours at RT. Plates were then washed 5 times with PBS-Tween and goat biotinylated anti-human IgG heavy and light chain monkey adsorbed polyclonal antibodies coupled to HRP were applied at a 50,000-fold dilution (Bethyl, catno: A80-319P) and allowed to bind for 1 hour at RT. Plates were then washed 5 times with PBS-Tween and s(HS)TMB weakener (SDT, #sTMB-VV) was added. The staining was allowed to proceed for 10 minutes and then stopped with 1 N $H_2SO$, after which the Optical Density was measured at 450 nm. The samples were analysed 3 times and 230C9-N297Q (from the same batch that was injected into the animals) was used for a standard curve.

Figure 12:
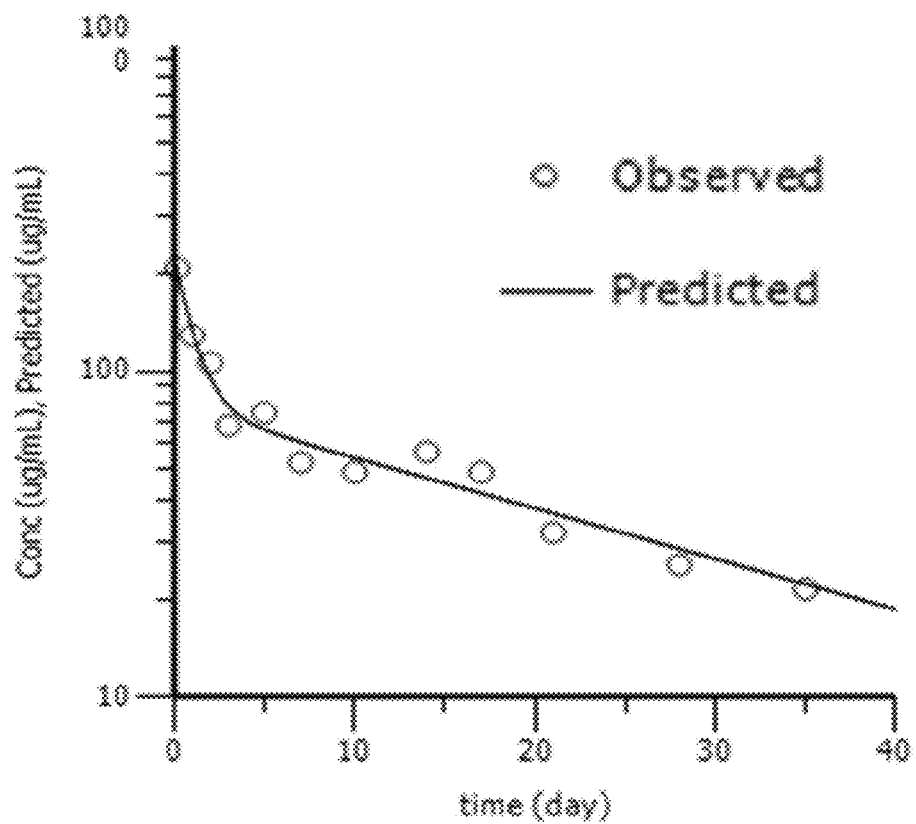
FIG. 12 shows pharmacokinetic data for IL-22R antibody 230C9. Cynomolgus monkeys were injected intravenously with a single 10 mg/kg dose of antibody. Samples were taken at different time points and tested for plasma concentration of antibody by ELISA. Antibody 230C9 was found to have a half-life of about 19.4 days.

The relevant PK parameters for a 2-compartment IV-infusion model analysis are shown in Table 27. The pharmacokinetic profiles for 230C9-N297Q antibody is shown graphically in FIG. 12 (the result shown is the average result of the two monkeys). This data clearly show that the antibody has a long mean residency time (MRT). Interestingly, although the antibody contains a non-glycosylated IgG1 Fc region without any modification to improve the half-life, the half-life of 230C9-N297Q is surprisingly long. Specifically, 230C9-N297Q has a half-life of about 19.4 days. Thus, the extended half-life of the antibodies of the invention appears to be due to the properties of the Fab regions.

TABLE 27

| PK parameters | | | | | | | |
|---|---|---|---|---|---|---|---|
| T½ | MRT | V1 | V2 | CL | K21 | Cmax | C at day 30 |
| 19.4 days | 26.2 days | 45 ml/kg | 68 ml/kg | 4.3 ml/day | 0.35 | 216 µg/ml | ~26 µg/ml |

Figure 13A:
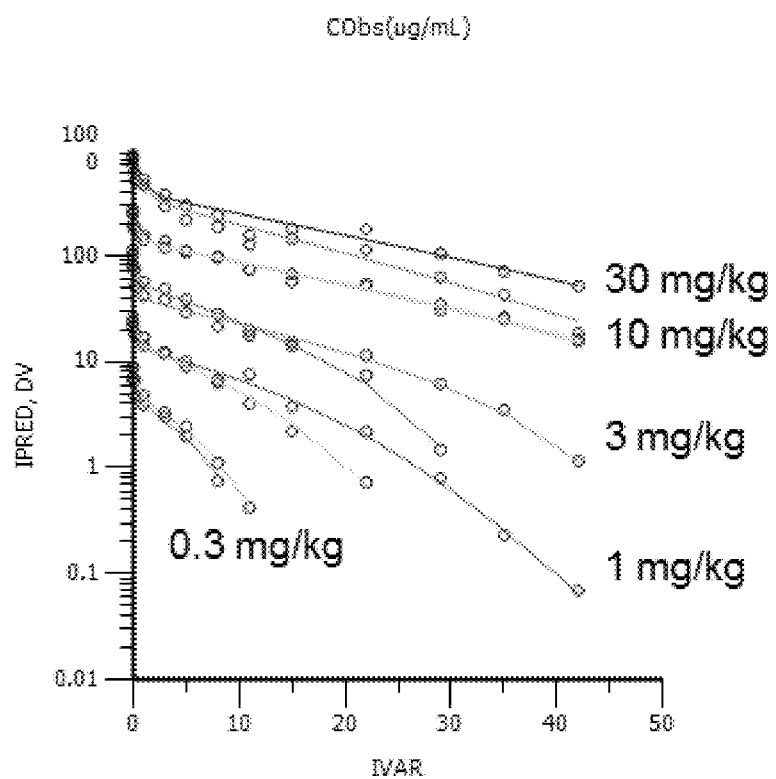
Figure 13B:
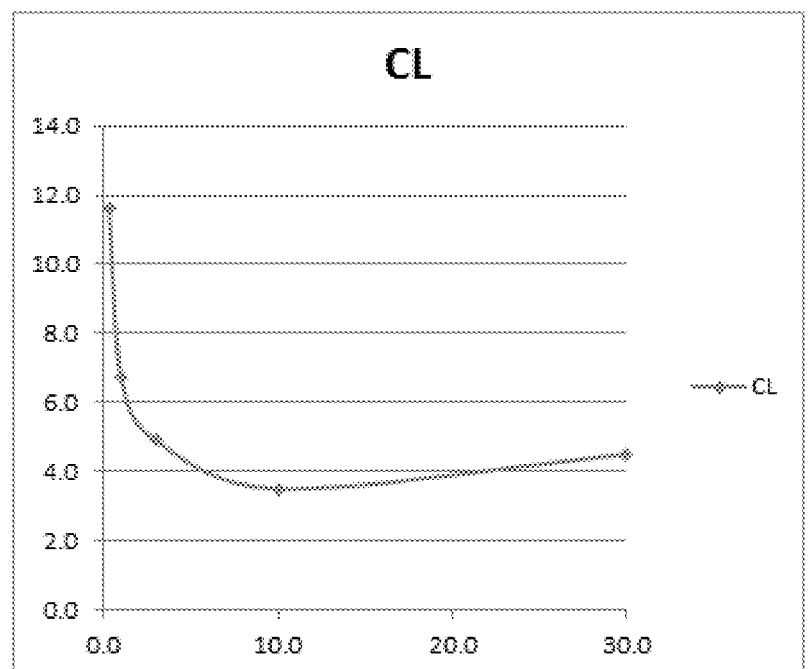

A further PK study was carried out in cynomolgus monkeys, by administering single IV doses (0.1, 1, 3, 10 and 30 mg/kg) of 230C9-N297Q to 10 monkeys in total. The kinetics in cynomolgus monkeys displayed two-compartment non-linear kinetics. At doses lower than 10 mg/kg, clearance (CL) increased with lowering of the dose resulting in a more than dose proportional decrease in exposure (AUC) with decreasing doses. This is a well-known phenomenon for monoclonal antibodies (see Table 28 and FIGS. 13A-13B).

TABLE 28

PK parameters based on 2 monkeys/per dose and 5 dose groups.

| Parameter | Estimate | Units | Stderr | CV % |
|---|---|---|---|---|
| tvV | 39.7 | mL/kg | 2.77 | 7.0 |
| tvCl | 3.60 | mL/(kg*day) | 0.38 | 10.5 |
| tvV2 | 27.7 | mL/kg | 5.40 | 19.5 |
| tvCl2 | 42.1 | mL/(kg*day) | 24.3 | 57.8 |
| tvVmax | 24.9 | µg/(kg*day) | 7.41 | 29.8 |
| tvKm | 1.0 | µg/mL | 0.01 | 9.96 |

Scaling of these parameters in order to predict human pharmacokinetics results in a human profile similar to what can be expected based on empiric findings from other human IgG1 molecules, including a point estimate of human half-life (T½) of about 18 days in agreement with the previous study reported above.

Example 14 Pharmacodynamic (PD) Effects of Antibody 230C9 N297Q in a Cynomolgus Monkey The pharmacodynamic effect of antibody 230C9 N297Q (ARGX-112) was analysed in a cynomolgus monkey by administering to the monkey by IV injection 230C9 at different doses (0.3, 1, 3, 10, 30 mg/kg). A skin section of the monkey was also treated with imiquimod (IMQ) to assess the effects of 230C9 N297Q on skin inflammation. IMQ has been reported to induce skin inflammation in mice (Van Belle et al. 2012, J Immunol. January 1; 188(1):462-9), and one report also demonstrates similar effects in non-human primate (Poirier et al, 2016, Exp Dermatol. March; 25(3): 233-4; Poirier et al, 2016, J Immunol. January 1; 196(1): 274-83), and in human (Vinter et al, 2015, Br J Dermatol. February; 172(2):345-53).

Following 5 days of IMQ treatment, a biopsy was taken from a non-IMQ treated area of skin and the IMQ-treated area of skin to assess the effects of 230C9 N297Q on the IMQ-induced effects. The effects were assessed by comparing epidermal thickness and frequency of proliferating nuclei in the epidermis (Ki67 frequency), and the results are shown in FIGS. 14A-14B. Increasing doses of antibody 230C9 N297Q were able to normalize epidermal thickness (FIG. 14A) and reduce the frequency of Ki67 positive nuclei (FIG. 14B). The $EC_{50}$ was approximately 3 mg/kg.

Example 15 Serum PK and Skin Explant PD Response Relationship after a Single IV Infusion of 230C9 N297Q in Cynomolgus Monkeys Skin target engagement was investigated in cynomolgus monkeys administered a single 15-min intravenous infusion (5 ml/kg) of antibody 230C9 N297Q. Female monkeys were left either untreated or exposed to 1, 5 or 30 mg/kg 230C9 on test day 1 (three animals per group). Blood was collected from all dosed animals (3×150 µL) at different time points with the last sample being withdrawn at day 7. Serum samples (1% v/v) were tested for 230C9 N297Q exposure levels by ELISA.

Skin punch biopsies (3 mm) were sampled at day −1 (pre-dose) and day 7 from each animal and incubated in the presence (day −1, day 7) or absence (day 7) of rhIL-22 for 24 h at 37° C. in humidified air/$CO_2$ (95%/5%) before measuring FLG2 mRNA levels by qPCR. The results are shown in FIG. 15.

Stimulation by rhIL22 resulted in a 5-fold reduction in total skin FLG2 mRNA levels. IL-22-mediated FLG2 transcript repression was significantly restored in 230C9 N297Q-treated animals indicating significant skin exposure in all dose groups.

Example 16 Effect of 230C9 N297Q in Viable Human and Cynomolgus Monkey Ex Vivo Skin Explants Freshly sourced abdominal skin from healthy human donors was used to assess the ability of antibody 230C9 N297Q to inhibit rhIL-22 induced DEFB4 mRNA levels.

Skin punch biopsies (3 mm) were placed in an upright position in 96-well tissue plates and cultured in air liquid interface in 100 µL EpiLife medium supplemented with Human Keratinocyte Growth Supplement (HKGS) without hydrocortisone (Invitrogen).

The samples were incubated with increasing concentrations of antibody 230C9 N297Q for 24 h at 37° C. in humidified air/$CO_2$ (95%/5%) prior to stimulation with 20 ng/ml rhIL-22 (R&D Systems) for an additional 24 h at 37° C. The relative DEFB4 gene expression levels in skin lysates were determined by real-time quantitative PCR (qPCR) using validated gene expression assays (Applied Biosystems) and an ABI PRISM® 7900HT sequence detection system.

FIG. 16 shows a dose dependent reduction of rhIL-22 induced DEFB4 mRNA levels from one representative experiment ($EC_{50}$ [CI95%]=4 nM [0.5-29 nM]; 4 donors). A similar potency was obtained if increasing the 230C9 N297Q pre-incubation time to 48 h suggesting IL-22RA binding equilibrium has been reached. An isotype control antibody had no effect on rhIL-22 mediated increments of DEFB4 mRNA levels.

In freshly isolated skin biopsies (3 mm) from cynomolgus monkeys (*Macaca fascicularis*) the DEFB4 gene was not regulated by rhIL-22. In contrast, both FLG2 and LOR were down-regulated following 24 h incubation with rhIL-22 using the same protocol as described for the human skin explant set-up. These responses were completely blocked by 24 h pre-incubation with antibody 230C9 N297Q ($EC_{50}$=11 nM; both genes) as shown in FIGS. 17A-17B.

Example 17 Efficacy of 230C9 N297Q in Human Keratinocytes

The assay was designed to test the potency of IL-22R antibodies in a functional assay in primary human keratinocytes. The cells were stimulated with a cytokine mixture of IL-4, IL-13, IL-22 (all 10 ng/mL) and IFN-γ, 1 ng/mL for 48 hours and then the level of CCL2 was measured in the culture supernatant using the MSD platform.

The keratinocytes were suspended in EpiLife medium (Life Technologies) with the following growth supplements added: EGF; BPE; Insulin; Transferrin and Gentamicin/Amphotericin. Cells were seeded in 384 well white proxy plates (Perkin Elmer) and incubated for 2 hours at 37° C., 5% $CO_2$/95% air. The cells were then treated with 80 nl antibody (at different concentrations as shown in FIG. 18) or vehicle. Then, 40 µl stimulation mixture (IL-4, IL-13, IL-22 (R&D systems, all 10 ng/mL final concentration) and IFN-γ (R&D systems, 1 ng/mL final concentration)) was added and the plates were incubated at 37° C., 5% $CO_2$/95% air for 2 days. Control wells were treated with a mixture of IL-4 and IL-13 (both 10 ng/mL) and IFN-γ, 1 ng/mL, and defined 100% inhibition of IL-22 signalling. The concentration of CCL2 in the culture supernatant was measured with MSD CCL2 kit (Mesoscale Cat #K151AYB-2). The viability of the cells was measured by PrestoBlue® reagent.

The potency of 230C9 N297Q was tested in 5 experiments and showed dose-dependent inhibition of CCL2 levels with $EC_{50}$ values of 0.10 nM [0.042-0.24 nM]. Representative experimental results from one experiment are shown in FIG. 18.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

The invention claimed is:

1. A method of treating a subject having a skin disorder, comprising administering to the subject a therapeutically effective amount of an antibody or an antigen binding fragment thereof, which binds to human interleukin 22 receptor protein (IL-22R), wherein
the antibody or antigen binding fragment thereof comprises a heavy chain variable domain (VH) and a light chain variable domain (VL), the VH comprising a combination of variable heavy chain CDR sequences: HCDR3 comprising SEQ ID NO: 6; HCDR2 comprising SEQ ID NO: 36; and HCDR1 comprising SEQ ID NO: 34, and the VL comprising a combination of variable light chain CDR sequences: LCDR3 comprising SEQ ID NO: 54; LCDR2 comprising SEQ ID NO: 47; and LCDR1 comprising SEQ ID NO: 16, thereby treating the subject.

2. The method of claim 1, wherein
the antibody or antigen binding fragment thereof comprises a combination of a heavy chain variable domain (VH) and a light chain variable domain (VL) selected from the following: a VH comprising the amino acid sequence of SEQ ID NO: 63 or an amino acid sequence at least 90%, 95%, 97%, 98% or 99% identical thereto and a VL comprising the amino acid sequence of SEQ ID NO: 64 or an amino acid sequence at least 90%, 95%, 97%, 98% or 99% identical thereto.

3. The method of claim 1, wherein the antibody or antigen binding fragment thereof contains a hinge region, a CH2 domain or a CH3 domain of a human IgG.

4. The method of claim 1, wherein the VH domain or the VL domain is a humanised or germlined variant of a camelid-derived VH or VL domain.

5. The method of claim 1, wherein the skin disorder is psoriasis, psoriatic arthritis or atopic dermatitis.

6. The method of claim 1, wherein the skin disorder is atopic dermatitis.

7. The method of claim 1, wherein the VH comprises an amino acid sequence at least 90% identical to the amino acid sequence of SEQ ID NO: 63.

8. The method of claim 1, wherein the VH comprises the amino acid sequence of SEQ ID NO: 63.

9. The method of claim 1, wherein the VL comprises an amino acid sequence at least 90% identical to the amino acid sequence of SEQ ID NO: 64.

10. The method of claim 1, wherein the VL comprises the amino acid sequence of SEQ ID NO: 64.

11. A method of treating a subject having a skin disorder, comprising administering to the subject a therapeutically effective amount of an antibody or an antigen binding fragment thereof, which binds to human interleukin 22 receptor protein (IL-22R), wherein the antibody comprises a heavy chain comprising a heavy chain variable domain (VH) and a light chain comprising a light chain variable domain (VL), the VH comprising the amino acid sequence of SEQ ID NO: 63 and the VL comprising the amino acid sequence of SEQ ID NO: 64, thereby treating the subject.

12. The method of claim 11, the antibody or antigen binding fragment further comprising the hinge region, CH2 domain or CH3 domain of a human IgG1 antibody.

13. The method of claim 11, wherein the heavy chain comprises an amino acid sequence at least 90% identical to the amino acid sequence of SEQ ID NO: 67.

14. The method of claim 11, wherein the heavy chain comprises an amino acid sequence at least 95% identical to the amino acid sequence of SEQ ID NO: 67.

15. The method of claim 11, wherein the heavy chain comprises an amino acid sequence at least 98% identical to the amino acid sequence of SEQ ID NO: 67.

16. The method of claim 11, wherein the heavy chain comprises an amino acid sequence at least 99% identical to the amino acid sequence of SEQ ID NO: 67.

17. The method of claim 11, wherein the heavy chain comprises the amino acid sequence of SEQ ID NO: 67.

18. The method of claim 11, wherein the light chain comprises an amino acid sequence at least 90% identical to the amino acid sequence of SEQ ID NO: 68.

19. The method of claim 11, wherein the light chain comprises an amino acid sequence at least 95% identical to the amino acid sequence of SEQ ID NO: 68.

20. The method of claim 11, wherein the light chain comprises an amino acid sequence at least 98% identical to the amino acid sequence of SEQ ID NO: 68.

21. The method of claim 11, wherein the light chain comprises an amino acid sequence at least 99% identical to the amino acid sequence of SEQ ID NO: 68.

22. The method of claim 11, wherein the light chain comprises the amino acid sequence of SEQ ID NO: 68.

23. The method of claim 11, wherein the heavy chain comprises an amino acid sequence at least 95% identical to the amino acid sequence of SEQ ID NO: 67 and wherein the light chain comprises an amino acid sequence at least 95% identical to the amino acid sequence of SEQ ID NO: 68.

24. The method of claim 11, wherein the skin disorder is psoriasis, psoriatic arthritis or atopic dermatitis.

25. The method of claim 11, wherein the skin disorder is atopic dermatitis.

26. A method of treating a subject having atopic dermatitis, comprising administering to the subject a therapeutically effective amount of an antibody or an antigen binding fragment thereof, which binds to human interleukin 22 receptor protein (IL-22R), wherein the antibody or antigen-binding fragment comprises a heavy chain and a light chain, wherein the heavy chain comprises the amino acid sequence of SEQ ID NO: 67 and wherein the light chain comprises the amino acid sequence of SEQ ID NO: 68, thereby treating the subject.

* * * * *

UNITED STATES PATENT AND TRADEMARK OFFICE
CERTIFICATE OF CORRECTION

| | | |
|---|---|---|
| PATENT NO. | : 11,447,544 B2 | Page 1 of 1 |
| APPLICATION NO. | : 16/661783 | |
| DATED | : September 20, 2022 | |
| INVENTOR(S) | : Blanchetot et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 92 days.

Signed and Sealed this
Seventh Day of January, 2025

Derrick Brent
*Acting Director of the United States Patent and Trademark Office*

SEQUENCE LISTING

<160> NUMBER OF SEQ ID NOS: 101

<210> SEQ ID NO 1
<211> LENGTH: 30
<212> TYPE: PRT
<213> ORGANISM: llama glama

<400> SEQUENCE: 1

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 2
<211> LENGTH: 5
<212> TYPE: PRT
<213> ORGANISM: llama glama

<400> SEQUENCE: 2

Ser Tyr Asp Met Ser
1               5

<210> SEQ ID NO 3
<211> LENGTH: 14
<212> TYPE: PRT
<213> ORGANISM: llama glama

<400> SEQUENCE: 3

Trp Val Arg Gln Ala Pro Gly Lys Gly Leu Glu Trp Val Ser
1               5                   10

<210> SEQ ID NO 4
<211> LENGTH: 17
<212> TYPE: PRT
<213> ORGANISM: llama glama

<400> SEQUENCE: 4

Ser Ile Tyr Asn Asp Gly Ser Asn Thr Ala Tyr Ser Asp Ser Val Lys
1               5                   10                  15

Gly

<210> SEQ ID NO 5
<211> LENGTH: 32
<212> TYPE: PRT
<213> ORGANISM: llama glama

<400> SEQUENCE: 5

Arg Phe Thr Ile Ser Arg Asp Asn Ala Lys Asn Thr Leu Tyr Leu Gln
1               5                   10                  15

Met Asn Ser Leu Lys Ser Glu Asp Thr Ala Val Tyr Tyr Cys Ala Lys
            20                  25                  30

<210> SEQ ID NO 6
<211> LENGTH: 11
<212> TYPE: PRT
<213> ORGANISM: llama glama

<400> SEQUENCE: 6

Val Gly Phe Ser Gly Thr Tyr Tyr Ser Glu Ser

```
<210> SEQ ID NO 7
<211> LENGTH: 11
<212> TYPE: PRT
<213> ORGANISM: llama glama

<400> SEQUENCE: 7

Trp Gly Gln Gly Thr Gln Val Thr Val Ser Ser
1               5                   10

<210> SEQ ID NO 8
<211> LENGTH: 30
<212> TYPE: PRT
<213> ORGANISM: llama glama

<400> SEQUENCE: 8

Gln Val Gln Leu Val Glu Ser Gly Gly Gly Leu Val Gln Pro Gly Asp
1               5                   10                  15

Ser Leu Arg Leu Ser Cys Ala Ala Ser Gly Phe Thr Phe Gly
            20                  25                  30

<210> SEQ ID NO 9
<211> LENGTH: 5
<212> TYPE: PRT
<213> ORGANISM: llama glama

<400> SEQUENCE: 9

Ser Tyr Phe Met Ser
1               5

<210> SEQ ID NO 10
<211> LENGTH: 14
<212> TYPE: PRT
<213> ORGANISM: llama glama

<400> SEQUENCE: 10

Trp Val Arg Gln Ala Pro Gly Lys Gly Pro Glu Trp Val Ser
1               5                   10

<210> SEQ ID NO 11
<211> LENGTH: 17
<212> TYPE: PRT
<213> ORGANISM: llama glama

<400> SEQUENCE: 11

Gly Ile His Ile Ser Gly Gly Ile Thr Tyr Tyr Leu Asp Ser Val Lys
1               5                   10                  15

Gly

<210> SEQ ID NO 12
<211> LENGTH: 32
<212> TYPE: PRT
<213> ORGANISM: llama glama

<400> SEQUENCE: 12

Arg Phe Thr Ile Ser Arg Asp Asn Ala Lys Asn Thr Leu Tyr Leu Gln
1               5                   10                  15

Met Asn Asn Leu Lys Pro Glu Asp Thr Ala Val Tyr Tyr Cys Val Thr
            20                  25                  30

<210> SEQ ID NO 13
<211> LENGTH: 14
```

```
<212> TYPE: PRT
<213> ORGANISM: llama glama

<400> SEQUENCE: 13

Pro Pro Gly Pro Phe Lys Ala His Tyr Asn Gly Met Lys Tyr
1               5                   10

<210> SEQ ID NO 14
<211> LENGTH: 11
<212> TYPE: PRT
<213> ORGANISM: llama glama

<400> SEQUENCE: 14

Trp Gly Lys Gly Thr Leu Val Thr Val Ser Ser
1               5                   10

<210> SEQ ID NO 15
<211> LENGTH: 22
<212> TYPE: PRT
<213> ORGANISM: llama glama

<400> SEQUENCE: 15

Asn Phe Met Leu Thr Gln Pro Ser Ala Val Ser Val Ser Leu Gly Gln
1               5                   10                  15

Thr Ala Lys Ile Thr Cys
            20

<210> SEQ ID NO 16
<211> LENGTH: 7
<212> TYPE: PRT
<213> ORGANISM: llama glama

<400> SEQUENCE: 16

Gln Gly Gly Tyr Tyr Ala His
1               5

<210> SEQ ID NO 17
<211> LENGTH: 15
<212> TYPE: PRT
<213> ORGANISM: llama glama

<400> SEQUENCE: 17

Trp Tyr Gln Gln Lys Pro Gly Gln Ala Pro Val Leu Val Ile Tyr
1               5                   10                  15

<210> SEQ ID NO 18
<211> LENGTH: 7
<212> TYPE: PRT
<213> ORGANISM: llama glama

<400> SEQUENCE: 18

Gly Asn Asn Asn Arg Pro Ser
1               5

<210> SEQ ID NO 19
<211> LENGTH: 20
<212> TYPE: PRT
<213> ORGANISM: llama glama

<400> SEQUENCE: 19

Asn Thr Ala Thr Leu Thr Ile Ser Gly Ala Gln Ala Glu Asp Glu Ala
1               5                   10                  15

Glu Tyr Tyr Cys
            20
```

```
<210> SEQ ID NO 20
<211> LENGTH: 10
<212> TYPE: PRT
<213> ORGANISM: llama glama

<400> SEQUENCE: 20

Gln Ser Gly Ser Ser Ser Ala Asn Ala Val
1               5                   10

<210> SEQ ID NO 21
<211> LENGTH: 10
<212> TYPE: PRT
<213> ORGANISM: llama glama

<400> SEQUENCE: 21

Phe Gly Gly Gly Thr His Leu Thr Val Leu
1               5                   10

<210> SEQ ID NO 22
<211> LENGTH: 22
<212> TYPE: PRT
<213> ORGANISM: llama glama

<400> SEQUENCE: 22

Asn Phe Met Leu Thr Gln Pro Pro Ser Val Ser Gly Thr Leu Gly Lys
1               5                   10                  15

Thr Val Thr Ile Ser Cys
            20

<210> SEQ ID NO 23
<211> LENGTH: 14
<212> TYPE: PRT
<213> ORGANISM: llama glama

<400> SEQUENCE: 23

Thr Gly Thr Ser Arg Asp Ile Gly Asp Tyr Asn Tyr Val Ser
1               5                   10

<210> SEQ ID NO 24
<211> LENGTH: 15
<212> TYPE: PRT
<213> ORGANISM: llama glama

<400> SEQUENCE: 24

Trp Tyr Gln Gln Leu Pro Gly Leu Ala Pro Lys Leu Leu Ile Tyr
1               5                   10                  15

<210> SEQ ID NO 25
<211> LENGTH: 7
<212> TYPE: PRT
<213> ORGANISM: llama glama

<400> SEQUENCE: 25

Lys Val Asn Thr Arg Ser Ser
1               5

<210> SEQ ID NO 26
<211> LENGTH: 20
<212> TYPE: PRT
<213> ORGANISM: llama glama

<400> SEQUENCE: 26

Asn Thr Ala Ser Leu Thr Ile Ser Gly Leu Gln Ser Glu Asp Glu Ala
```

```
                1               5                    10                   15

Asp Tyr Tyr Cys
            20

<210> SEQ ID NO 27
<211> LENGTH: 10
<212> TYPE: PRT
<213> ORGANISM: llama glama

<400> SEQUENCE: 27

Ala Ser Tyr Arg Leu Tyr Ala Asp Tyr Val
1               5                   10

<210> SEQ ID NO 28
<211> LENGTH: 10
<212> TYPE: PRT
<213> ORGANISM: llama glama

<400> SEQUENCE: 28

Phe Gly Gly Gly Thr His Leu Thr Val Leu
1               5                   10

<210> SEQ ID NO 29
<211> LENGTH: 120
<212> TYPE: PRT
<213> ORGANISM: llama glama

<400> SEQUENCE: 29

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ser Ile Tyr Asn Asp Gly Ser Asn Thr Ala Tyr Ser Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Val Gly Phe Ser Gly Thr Tyr Tyr Ser Glu Ser Trp Gly Gln
            100                 105                 110

Gly Thr Gln Val Thr Val Ser Ser
        115                 120

<210> SEQ ID NO 30
<211> LENGTH: 103
<212> TYPE: PRT
<213> ORGANISM: llama glama

<400> SEQUENCE: 30

Asn Phe Met Leu Thr Gln Pro Ser Ala Val Ser Val Ser Leu Gly Gln
1               5                   10                  15

Thr Ala Lys Ile Thr Cys Gln Gly Gly Tyr Tyr Ala His Trp Tyr Gln
            20                  25                  30

Gln Lys Pro Gly Gln Ala Pro Val Leu Val Ile Tyr Gly Asn Asn Asn
        35                  40                  45

Arg Pro Ser Gly Ile Pro Glu Arg Phe Ser Gly Ser Ser Ser Gly Asn
    50                  55                  60
```

```
Thr Ala Thr Leu Thr Ile Ser Gly Ala Gln Ala Glu Asp Glu Ala Glu
 65                  70                  75                  80

Tyr Tyr Cys Gln Ser Gly Ser Ser Ala Asn Ala Val Phe Gly Gly
                 85                  90                  95

Gly Thr His Leu Thr Val Leu
            100

<210> SEQ ID NO 31
<211> LENGTH: 123
<212> TYPE: PRT
<213> ORGANISM: llama glama

<400> SEQUENCE: 31

Gln Val Gln Leu Val Glu Ser Gly Gly Gly Leu Val Gln Pro Gly Asp
  1               5                  10                  15

Ser Leu Arg Leu Ser Cys Ala Ala Ser Gly Phe Thr Phe Gly Ser Tyr
                 20                  25                  30

Phe Met Ser Trp Val Arg Gln Ala Pro Gly Lys Gly Pro Glu Trp Val
             35                  40                  45

Ser Gly Ile His Ile Ser Gly Gly Ile Thr Tyr Tyr Leu Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Asn Leu Lys Pro Glu Asp Thr Ala Val Tyr Tyr Cys
                 85                  90                  95

Val Thr Pro Pro Gly Pro Phe Lys Ala His Tyr Asn Gly Met Lys Tyr
            100                 105                 110

Trp Gly Lys Gly Thr Leu Val Thr Val Ser Ser
            115                 120

<210> SEQ ID NO 32
<211> LENGTH: 110
<212> TYPE: PRT
<213> ORGANISM: llama glama

<400> SEQUENCE: 32

Asn Phe Met Leu Thr Gln Pro Pro Ser Val Ser Gly Thr Leu Gly Lys
  1               5                  10                  15

Thr Val Thr Ile Ser Cys Thr Gly Thr Ser Arg Asp Ile Gly Asp Tyr
                 20                  25                  30

Asn Tyr Val Ser Trp Tyr Gln Gln Leu Pro Gly Leu Ala Pro Lys Leu
             35                  40                  45

Leu Ile Tyr Lys Val Asn Thr Arg Ser Ser Gly Thr Pro Asp Arg Phe
 50                  55                  60

Ser Gly Ser Lys Ser Gly Asn Thr Ala Ser Leu Thr Ile Ser Gly Leu
 65                  70                  75                  80

Gln Ser Glu Asp Glu Ala Asp Tyr Tyr Cys Ala Ser Tyr Arg Leu Tyr
                 85                  90                  95

Ala Asp Tyr Val Phe Gly Gly Gly Thr His Leu Thr Val Leu
            100                 105                 110

<210> SEQ ID NO 33
<211> LENGTH: 30
<212> TYPE: PRT
<213> ORGANISM: llama glama

<400> SEQUENCE: 33

Gln Val Gln Leu Val Glu Ser Gly Gly Gly Leu Val Gln Pro Gly Gly
```

```
               1               5                  10                  15
Ser Leu Arg Leu Ser Cys Ala Ala Ser Gly Phe Thr Phe Ser
               20                  25                  30
```

<210> SEQ ID NO 34
<211> LENGTH: 5
<212> TYPE: PRT
<213> ORGANISM: Artificial Sequence
<220> FEATURE:
<223> OTHER INFORMATION: Germlined antibody fragment

<400> SEQUENCE: 34

```
Ser Tyr Asp Met Asn
1               5
```

<210> SEQ ID NO 35
<211> LENGTH: 14
<212> TYPE: PRT
<213> ORGANISM: llama glama

<400> SEQUENCE: 35

```
Trp Val Arg Gln Ala Pro Gly Lys Gly Leu Glu Trp Val Ser
1               5                  10
```

<210> SEQ ID NO 36
<211> LENGTH: 17
<212> TYPE: PRT
<213> ORGANISM: Artificial Sequence
<220> FEATURE:
<223> OTHER INFORMATION: Germlined antibody sequence

<400> SEQUENCE: 36

```
Ser Ile Tyr Asn Asp Ala Ser Asn Thr Ala Tyr Ser Asp Ser Val Lys
1               5                  10                  15

Gly
```

<210> SEQ ID NO 37
<211> LENGTH: 32
<212> TYPE: PRT
<213> ORGANISM: Artificial Sequence
<220> FEATURE:
<223> OTHER INFORMATION: Germlined antibody sequence

<400> SEQUENCE: 37

```
Arg Phe Thr Ile Ser Arg Asp Asn Ser Lys Asn Thr Leu Tyr Leu Gln
1               5                  10                  15
Met Asn Ser Leu Arg Ala Glu Asp Thr Ala Val Tyr Tyr Cys Ala Lys
               20                  25                  30
```

<210> SEQ ID NO 38
<211> LENGTH: 11
<212> TYPE: PRT
<213> ORGANISM: Artificial Sequence
<220> FEATURE:
<223> OTHER INFORMATION: Germlined antibody sequence

<400> SEQUENCE: 38

```
Trp Gly Gln Gly Thr Leu Val Thr Val Ser Ser
1               5                  10
```

<210> SEQ ID NO 39
<211> LENGTH: 30
<212> TYPE: PRT
<213> ORGANISM: llama glama

<400> SEQUENCE: 39

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 40
<211> LENGTH: 14
<212> TYPE: PRT
<213> ORGANISM: llama glama

<400> SEQUENCE: 40

Trp Val Arg Gln Ala Pro Gly Lys Gly Pro Glu Trp Val Ser
1               5                   10

<210> SEQ ID NO 41
<211> LENGTH: 17
<212> TYPE: PRT
<213> ORGANISM: Artificial Sequence
<220> FEATURE:
<223> OTHER INFORMATION: Germlined antibody sequence

<400> SEQUENCE: 41

Gly Ile His Ile Ser Gly Gly Ile Thr Tyr Tyr Thr Asp Ser Val Lys
1               5                   10                  15

Gly

<210> SEQ ID NO 42
<211> LENGTH: 32
<212> TYPE: PRT
<213> ORGANISM: Artificial Sequence
<220> FEATURE:
<223> OTHER INFORMATION: Germlined antibody sequence

<400> SEQUENCE: 42

Arg Phe Thr Ile Ser Arg Asp Asn Ala Lys Asn Thr Leu Tyr Leu Gln
1               5                   10                  15

Met Asn Ser Leu Arg Ala Glu Asp Thr Ala Val Tyr Tyr Cys Val Thr
            20                  25                  30

<210> SEQ ID NO 43
<211> LENGTH: 14
<212> TYPE: PRT
<213> ORGANISM: Artificial Sequence
<220> FEATURE:
<223> OTHER INFORMATION: Germlined antibody sequence

<400> SEQUENCE: 43

Pro Pro Gly Pro Phe Lys Ala His Tyr Asn Gly Ala Lys Tyr
1               5                   10

<210> SEQ ID NO 44
<211> LENGTH: 11
<212> TYPE: PRT
<213> ORGANISM: llama glama

<400> SEQUENCE: 44

Trp Gly Lys Gly Thr Leu Val Thr Val Ser Ser
1               5                   10

<210> SEQ ID NO 45
<211> LENGTH: 22
<212> TYPE: PRT
<213> ORGANISM: llama glama

<400> SEQUENCE: 45

Leu Pro Val Leu Thr Gln Pro Ser Ala Val Ser Val Ser Leu Gly Gln
1               5                   10                  15

Thr Ala Arg Ile Thr Cys
            20

<210> SEQ ID NO 46
<211> LENGTH: 15
<212> TYPE: PRT
<213> ORGANISM: llama glama

<400> SEQUENCE: 46

Trp Tyr Gln Gln Lys Pro Gly Gln Ala Pro Val Leu Val Ile Tyr
1               5                   10                  15

<210> SEQ ID NO 47
<211> LENGTH: 7
<212> TYPE: PRT
<213> ORGANISM: llama glama

<400> SEQUENCE: 47

Gly Gln Asn Asn Arg Pro Ser
1               5

<210> SEQ ID NO 48
<211> LENGTH: 20
<212> TYPE: PRT
<213> ORGANISM: llama glama

<400> SEQUENCE: 48

Asn Thr Ala Thr Leu Thr Ile Ser Gly Ala Gln Ala Glu Asp Glu Ala
1               5                   10                  15

Glu Tyr Tyr Cys
            20

<210> SEQ ID NO 49
<211> LENGTH: 10
<212> TYPE: PRT
<213> ORGANISM: llama glama

<400> SEQUENCE: 49

Phe Gly Gly Gly Thr Lys Leu Thr Val Leu
1               5                   10

<210> SEQ ID NO 50
<211> LENGTH: 22
<212> TYPE: PRT
<213> ORGANISM: Artificial Sequence
<220> FEATURE:
<223> OTHER INFORMATION: Germlined antibody sequence

<400> SEQUENCE: 50

Ser Tyr Glu Leu Thr Gln Pro Ser Ser Val Ser Val Ala Leu Gly Gln
1               5                   10                  15

Thr Ala Arg Ile Thr Cys
            20

<210> SEQ ID NO 51
<211> LENGTH: 15
<212> TYPE: PRT
<213> ORGANISM: llama glama

<400> SEQUENCE: 51

```
Trp Tyr Gln Gln Lys Pro Gly Gln Ala Pro Val Leu Val Ile Tyr
1               5                   10                  15
```

<210> SEQ ID NO 52
<211> LENGTH: 360
<212> TYPE: PRT
<213> ORGANISM: llama glama

<400> SEQUENCE: 52

```
Cys Ala Gly Gly Thr Gly Cys Ala Gly Cys Thr Cys Gly Thr Gly Gly
1               5                   10                  15

Ala Gly Thr Cys Thr Gly Gly Gly Gly Ala Gly Gly Cys Thr Thr
            20                  25                  30

Gly Gly Thr Gly Cys Ala Gly Cys Cys Thr Gly Gly Gly Gly Gly Thr
            35                  40                  45

Thr Cys Thr Cys Thr Gly Ala Gly Ala Cys Thr Cys Thr Cys Cys Thr
        50                  55                  60

Gly Thr Gly Cys Ala Gly Cys Cys Thr Cys Thr Gly Gly Ala Thr Thr
65                  70                  75                  80

Cys Ala Cys Cys Thr Thr Cys Ala Gly Thr Ala Gly Cys Thr Ala Cys
                85                  90                  95

Gly Ala Cys Ala Thr Gly Ala Gly Cys Thr Gly Gly Gly Thr Cys Cys
                100                 105                 110

Gly Cys Cys Ala Gly Gly Cys Thr Cys Cys Ala Gly Gly Gly Ala Ala
            115                 120                 125

Gly Gly Gly Gly Cys Thr Gly Gly Ala Gly Thr Gly Gly Gly Thr Gly
130                 135                 140

Thr Cys Cys Ala Gly Thr Ala Thr Thr Ala Thr Ala Ala Thr Gly
145                 150                 155                 160

Ala Cys Gly Gly Thr Ala Gly Thr Ala Ala Cys Ala Cys Ala Gly Cys
                165                 170                 175

Cys Thr Ala Thr Thr Cys Ala Gly Ala Cys Thr Cys Cys Gly Thr Gly
                180                 185                 190

Ala Ala Gly Gly Gly Cys Cys Gly Ala Thr Thr Cys Ala Cys Cys Ala
                195                 200                 205

Thr Cys Thr Cys Cys Ala Gly Ala Gly Ala Cys Ala Ala Cys Gly Cys
                210                 215                 220

Cys Ala Ala Gly Ala Ala Cys Ala Cys Gly Thr Gly Thr Ala Thr
225                 230                 235                 240

Cys Thr Gly Cys Ala Ala Ala Thr Gly Ala Ala Cys Ala Gly Cys Thr
                245                 250                 255

Thr Gly Ala Ala Ala Thr Cys Thr Gly Ala Gly Gly Ala Cys Ala Cys
                260                 265                 270

Gly Gly Cys Cys Gly Thr Gly Thr Ala Thr Thr Ala Cys Thr Gly Thr
            275                 280                 285

Gly Cys Ala Ala Ala Gly Thr Thr Gly Gly Cys Thr Thr Ala
            290                 295                 300

Gly Thr Gly Gly Thr Ala Cys Thr Thr Ala Cys Thr Ala Cys Ala Gly
305                 310                 315                 320

Thr Gly Ala Ala Thr Cys Ala Thr Gly Gly Gly Cys Cys Ala Gly
                325                 330                 335

Gly Gly Gly Ala Cys Cys Cys Ala Gly Gly Thr Cys Ala Cys Cys Gly
                340                 345                 350

Thr Gly Thr Cys Cys Thr Cys Ala
```

<210> SEQ ID NO 53
<211> LENGTH: 20
<212> TYPE: PRT
<213> ORGANISM: Artificial Seqence
<220> FEATURE:
<223> OTHER INFORMATION: Germlined antibody sequence

<400> SEQUENCE: 53

Asn Thr Ala Thr Leu Thr Ile Ser Arg Ala Gln Ala Glu Asp Glu Ala
1               5                   10                  15

Asp Tyr Tyr Cys
            20

<210> SEQ ID NO 54
<211> LENGTH: 10
<212> TYPE: PRT
<213> ORGANISM: Artificial Sequence
<220> FEATURE:
<223> OTHER INFORMATION: Germlined antibody sequence

<400> SEQUENCE: 54

Gln Ser Gly Ser Ser Ser Ser Asn Ala Val
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Germlined antibody sequence

<400> SEQUENCE: 55

Phe Gly Gly Gly Thr Lys Leu Thr Val Leu
1               5                   10

<210> SEQ ID NO 56
<211> LENGTH: 22
<212> TYPE: PRT
<213> ORGANISM: Artificial Sequence
<220> FEATURE:
<223> OTHER INFORMATION: Germlined antibody sequence

<400> SEQUENCE: 56

Gln Ser Ala Leu Thr Gln Pro Pro Ser Val Ser Gly Ser Pro Gly Gln
1               5                   10                  15

Ser Val Thr Ile Ser Cys
            20

<210> SEQ ID NO 57
<211> LENGTH: 14
<212> TYPE: PRT
<213> ORGANISM: Artificial Sequence
<220> FEATURE:
<223> OTHER INFORMATION: Germlined antibody sequence

<400> SEQUENCE: 57

Thr Gly Thr Ser Ser Asp Ile Gly Ser Tyr Asn Tyr Val Ser
1               5                   10

<210> SEQ ID NO 58
<211> LENGTH: 15
<212> TYPE: PRT
<213> ORGANISM: Artificial Sequence
<220> FEATURE:

```
<223> OTHER INFORMATION: Germlined antibody sequence

<400> SEQUENCE: 58

Trp Tyr Gln Gln Leu Pro Gly Lys Ala Pro Lys Leu Leu Ile Tyr
1               5                   10                  15

<210> SEQ ID NO 59
<211> LENGTH: 7
<212> TYPE: PRT
<213> ORGANISM: Artificial Sequence
<220> FEATURE:
<223> OTHER INFORMATION: Germlined antibody sequence

<400> SEQUENCE: 59

Glu Val Asn Lys Arg Ser Ser
1               5

<210> SEQ ID NO 60
<211> LENGTH: 20
<212> TYPE: PRT
<213> ORGANISM: Artificial Sequence
<220> FEATURE:
<223> OTHER INFORMATION: Germlined antibody sequence

<400> SEQUENCE: 60

Asn Thr Ala Ser Leu Thr Ile Ser Gly Leu Gln Ala Glu Asp Glu Ala
1               5                   10                  15

Asp Tyr Tyr Cys
            20

<210> SEQ ID NO 61
<211> LENGTH: 10
<212> TYPE: PRT
<213> ORGANISM: llama glama

<400> SEQUENCE: 61

Phe Gly Gly Gly Thr Gln Leu Thr Val Leu
1               5                   10

<210> SEQ ID NO 62
<211> LENGTH: 103
<212> TYPE: PRT
<213> ORGANISM: llama glama

<400> SEQUENCE: 62

Leu Pro Val Leu Thr Gln Pro Ser Ala Val Ser Val Ser Leu Gly Gln
1               5                   10                  15

Thr Ala Arg Ile Thr Cys Gln Gly Gly Tyr Tyr Ala His Trp Tyr Gln
            20                  25                  30

Gln Lys Pro Gly Gln Ala Pro Val Leu Val Ile Tyr Gly Gln Asn Asn
        35                  40                  45

Arg Pro Ser Gly Ile Pro Glu Arg Phe Ser Gly Ser Gly Ala Gly Asn
    50                  55                  60

Thr Ala Thr Leu Thr Ile Ser Gly Ala Gln Ala Glu Asp Glu Ala Glu
65                  70                  75                  80

Tyr Tyr Cys Gln Ser Gly Ser Ser Ser Ala Asn Ala Val Phe Gly Gly
                85                  90                  95

Gly Thr Lys Leu Thr Val Leu
            100

<210> SEQ ID NO 63
<211> LENGTH: 120
```

```
<212> TYPE: PRT
<213> ORGANISM: Artificial Sequence
<220> FEATURE:
<223> OTHER INFORMATION: Germlined antibody sequence

<400> SEQUENCE: 63

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Asn Trp Val Arg Gln Ala Pro Gly Lys Gly Leu Glu Trp Val
        35                  40                  45

Ser Ser Ile Tyr Asn Asp Ala Ser Asn Thr Ala Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Gly Phe Ser Gly Thr Tyr Tyr Ser Glu Ser Trp Gly Gln
            100                 105                 110

Gly Thr Leu Val Thr Val Ser Ser
        115                 120

<210> SEQ ID NO 64
<211> LENGTH: 103
<212> TYPE: PRT
<213> ORGANISM: Artificial Sequence
<220> FEATURE:
<223> OTHER INFORMATION: Germlined antibody sequence

<400> SEQUENCE: 64

Ser Tyr Glu Leu Thr Gln Pro Ser Ser Val Ser Val Ala Leu Gly Gln
1               5                   10                  15

Thr Ala Arg Ile Thr Cys Gln Gly Gly Tyr Tyr Ala His Trp Tyr Gln
            20                  25                  30

Gln Lys Pro Gly Gln Ala Pro Val Leu Val Ile Tyr Gly Gln Asn Asn
        35                  40                  45

Arg Pro Ser Gly Ile Pro Glu Arg Phe Ser Gly Ser Gly Ala Gly Asn
    50                  55                  60

Thr Ala Thr Leu Thr Ile Ser Arg Ala Gln Ala Glu Asp Glu Ala Asp
65                  70                  75                  80

Tyr Tyr Cys Gln Ser Gly Ser Ser Ser Asn Ala Val Phe Gly Gly
                85                  90                  95

Gly Thr Lys Leu Thr Val Leu
            100

<210> SEQ ID NO 65
<211> LENGTH: 123
<212> TYPE: PRT
<213> ORGANISM: Artificial Sequence
<220> FEATURE:
<223> OTHER INFORMATION: Germlined antibody sequence

<400> SEQUENCE: 65

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Phe Met Ser Trp Val Arg Gln Ala Pro Gly Lys Gly Pro Glu Trp Val
```

```
                35                  40                  45
Ser Gly Ile His Ile Ser Gly Gly Ile Thr Tyr Tyr Thr Asp Ser Val
         50                  55                  60
Lys Gly Arg Phe Thr Ile Ser Arg Asp Asn Ala Lys Asn Thr Leu Tyr
 65                  70                  75                  80
Leu Gln Met Asn Ser Leu Arg Ala Glu Asp Thr Ala Val Tyr Tyr Cys
                 85                  90                  95
Val Thr Pro Pro Gly Pro Phe Lys Ala His Tyr Asn Gly Ala Lys Tyr
            100                 105                 110
Trp Gly Lys Gly Thr Leu Val Thr Val Ser Ser
            115                 120
```

<210> SEQ ID NO 66
<211> LENGTH: 110
<212> TYPE: PRT
<213> ORGANISM: Artificial Sequence
<220> FEATURE:
<223> OTHER INFORMATION: Germlined antibody sequence

<400> SEQUENCE: 66

```
Gln Ser Ala Leu Thr Gln Pro Pro Ser Val Ser Gly Ser Pro Gly Gln
 1               5                  10                  15
Ser Val Thr Ile Ser Cys Thr Gly Thr Ser Ser Asp Ile Gly Ser Tyr
                 20                  25                  30
Asn Tyr Val Ser Trp Tyr Gln Gln Leu Pro Gly Lys Ala Pro Lys Leu
             35                  40                  45
Leu Ile Tyr Glu Val Asn Lys Arg Ser Ser Gly Val Pro Asp Arg Phe
 50                  55                  60
Ser Gly Ser Lys Ser Gly Asn Thr Ala Ser Leu Thr Ile Ser Gly Leu
 65                  70                  75                  80
Gln Ala Glu Asp Glu Ala Asp Tyr Tyr Cys Ala Ser Tyr Arg Leu Tyr
                 85                  90                  95
Ala Asp Tyr Val Phe Gly Gly Gly Thr Gln Leu Thr Val Leu
             100                 105                 110
```

<210> SEQ ID NO 67
<211> LENGTH: 450
<212> TYPE: PRT
<213> ORGANISM: Artificial Sequence
<220> FEATURE:
<223> OTHER INFORMATION: Germlined antibody sequence

<400> SEQUENCE: 67

```
Gln Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Tyr
                 20                  25                  30
Asp Met Asn Trp Val Arg Gln Ala Pro Gly Lys Gly Leu Glu Trp Val
             35                  40                  45
Ser Ser Ile Tyr Asn Asp Ala Ser Asn Thr Ala Tyr Ser Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Val Gly Phe Ser Gly Tyr Tyr Ser Glu Ser Trp Gly Gln
             100                 105                 110
```

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gln Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 68
<211> LENGTH: 209
<212> TYPE: PRT
<213> ORGANISM: Artificial Sequence
<220> FEATURE:
<223> OTHER INFORMATION: Germlined antibody sequence

<400> SEQUENCE: 68

Ser Tyr Glu Leu Thr Gln Pro Ser Ser Val Ser Val Ala Leu Gly Gln
1               5                   10                  15

```
Thr Ala Arg Ile Thr Cys Gln Gly Gly Tyr Tyr Ala His Trp Tyr Gln
            20                  25                  30

Gln Lys Pro Gly Gln Ala Pro Val Leu Val Ile Tyr Gly Gln Asn Asn
        35                  40                  45

Arg Pro Ser Gly Ile Pro Glu Arg Phe Ser Gly Ser Gly Ala Gly Asn
    50                  55                  60

Thr Ala Thr Leu Thr Ile Ser Arg Ala Gln Ala Glu Asp Glu Ala Asp
65                  70                  75                  80

Tyr Tyr Cys Gln Ser Gly Ser Ser Ser Asn Ala Val Phe Gly Gly
            85                  90                  95

Gly Thr Lys Leu Thr Val Leu Gly Gln Pro Lys Ala Ala Pro Ser Val
            100                 105                 110

Thr Leu Phe Pro Pro Ser Ser Glu Glu Leu Gln Ala Asn Lys Ala Thr
            115                 120                 125

Leu Val Cys Leu Ile Ser Asp Phe Tyr Pro Gly Ala Val Thr Val Ala
            130                 135                 140

Trp Lys Ala Asp Ser Ser Pro Val Lys Ala Gly Val Glu Thr Thr Thr
145                 150                 155                 160

Pro Ser Lys Gln Ser Asn Asn Lys Tyr Ala Ala Ser Ser Tyr Leu Ser
                165                 170                 175

Leu Thr Pro Glu Gln Trp Lys Ser His Arg Ser Tyr Ser Cys Gln Val
            180                 185                 190

Thr His Glu Gly Ser Thr Val Glu Lys Thr Val Ala Pro Thr Glu Cys
            195                 200                 205

Ser

<210> SEQ ID NO 69
<211> LENGTH: 453
<212> TYPE: PRT
<213> ORGANISM: Artificial Sequence
<220> FEATURE:
<223> OTHER INFORMATION: Germlined antibody sequence

<400> SEQUENCE: 69

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Phe Met Ser Trp Val Arg Gln Ala Pro Gly Lys Gly Pro Glu Trp Val
        35                  40                  45

Ser Gly Ile His Ile Ser Gly Ile Thr Tyr Tyr Thr Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
            85                  90                  95

Val Thr Pro Pro Gly Pro Phe Lys Ala His Tyr Asn Gly Ala Lys Tyr
            100                 105                 110

Trp Gly Lys Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
```

-continued

```
                165                 170                 175
Pro Ala Val Leu Gln Ser Ser Gly Leu Tyr Ser Leu Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Gln Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 70
<211> LENGTH: 216
<212> TYPE: PRT
<213> ORGANISM: Artificial Sequence
<220> FEATURE:
<223> OTHER INFORMATION: Germlined antibody sequence

<400> SEQUENCE: 70

Gln Ser Ala Leu Thr Gln Pro Pro Ser Val Ser Gly Ser Pro Gly Gln
1               5                   10                  15

Ser Val Thr Ile Ser Cys Thr Gly Thr Ser Ser Asp Ile Gly Ser Tyr
            20                  25                  30

Asn Tyr Val Ser Trp Tyr Gln Gln Leu Pro Gly Lys Ala Pro Lys Leu
        35                  40                  45

Leu Ile Tyr Glu Val Asn Lys Arg Ser Ser Gly Val Pro Asp Arg Phe
    50                  55                  60

Ser Gly Ser Lys Ser Gly Asn Thr Ala Ser Leu Thr Ile Ser Gly Leu
```

```
               65                  70                  75                  80
Gln Ala Glu Asp Glu Ala Asp Tyr Tyr Cys Ala Ser Tyr Arg Leu Tyr
                85                  90                  95

Ala Asp Tyr Val Phe Gly Gly Gly Thr Gln Leu Thr Val Leu Gly Gln
                100                 105                 110

Pro Lys Ala Ala Pro Ser Val Thr Leu Phe Pro Pro Ser Ser Glu Glu
                115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
                195                 200                 205

Thr Val Ala Pro Thr Glu Cys Ser
    210                 215

<210> SEQ ID NO 71
<211> LENGTH: 574
<212> TYPE: PRT
<213> ORGANISM: homo sapiens

<400> SEQUENCE: 71

Met Arg Thr Leu Leu Thr Ile Leu Thr Val Gly Ser Leu Ala Ala His
1               5                   10                  15

Ala Pro Glu Asp Pro Ser Asp Leu Leu Gln His Val Lys Phe Gln Ser
                20                  25                  30

Ser Asn Phe Glu Asn Ile Leu Thr Trp Asp Ser Gly Pro Glu Gly Thr
                35                  40                  45

Pro Asp Thr Val Tyr Ser Ile Glu Tyr Lys Thr Tyr Gly Glu Arg Asp
    50                  55                  60

Trp Val Ala Lys Lys Gly Cys Gln Arg Ile Thr Arg Lys Ser Cys Asn
65                  70                  75                  80

Leu Thr Val Glu Thr Gly Asn Leu Thr Glu Leu Tyr Tyr Ala Arg Val
                85                  90                  95

Thr Ala Val Ser Ala Gly Gly Arg Ser Ala Thr Lys Met Thr Asp Arg
                100                 105                 110

Phe Ser Ser Leu Gln His Thr Thr Leu Lys Pro Pro Asp Val Thr Cys
                115                 120                 125

Ile Ser Lys Val Arg Ser Ile Gln Met Ile Val His Pro Thr Pro Thr
    130                 135                 140

Pro Ile Arg Ala Gly Asp Gly His Arg Leu Thr Leu Glu Asp Ile Phe
145                 150                 155                 160

His Asp Leu Phe Tyr His Leu Glu Leu Gln Val Asn Arg Thr Tyr Gln
                165                 170                 175

Met His Leu Gly Gly Lys Gln Arg Glu Tyr Glu Phe Phe Gly Leu Thr
                180                 185                 190

Pro Asp Thr Glu Phe Leu Gly Thr Ile Met Ile Cys Val Pro Thr Trp
                195                 200                 205

Ala Lys Glu Ser Ala Pro Tyr Met Cys Arg Val Lys Thr Leu Pro Asp
    210                 215                 220
```

```
Arg Thr Trp Thr Tyr Ser Phe Ser Gly Ala Phe Leu Phe Ser Met Gly
225                 230                 235                 240

Phe Leu Val Ala Val Leu Cys Tyr Leu Ser Tyr Arg Tyr Val Thr Lys
            245                 250                 255

Pro Pro Ala Pro Pro Asn Ser Leu Asn Val Gln Arg Val Leu Thr Phe
        260                 265                 270

Gln Pro Leu Arg Phe Ile Gln Glu His Val Leu Ile Pro Val Phe Asp
    275                 280                 285

Leu Ser Gly Pro Ser Ser Leu Ala Gln Pro Val Gln Tyr Ser Gln Ile
290                 295                 300

Arg Val Ser Gly Pro Arg Glu Pro Ala Gly Ala Pro Gln Arg His Ser
305                 310                 315                 320

Leu Ser Glu Ile Thr Tyr Leu Gly Gln Pro Asp Ile Ser Ile Leu Gln
            325                 330                 335

Pro Ser Asn Val Pro Pro Pro Gln Ile Leu Ser Pro Leu Ser Tyr Ala
        340                 345                 350

Pro Asn Ala Ala Pro Glu Val Gly Pro Pro Ser Tyr Ala Pro Gln Val
    355                 360                 365

Thr Pro Glu Ala Gln Phe Pro Phe Tyr Ala Pro Gln Ala Ile Ser Lys
370                 375                 380

Val Gln Pro Ser Ser Tyr Ala Pro Gln Ala Thr Pro Asp Ser Trp Pro
385                 390                 395                 400

Pro Ser Tyr Gly Val Cys Met Glu Gly Ser Gly Lys Asp Ser Pro Thr
            405                 410                 415

Gly Thr Leu Ser Ser Pro Lys His Leu Arg Pro Lys Gly Gln Leu Gln
        420                 425                 430

Lys Glu Pro Pro Ala Gly Ser Cys Met Leu Gly Gly Leu Ser Leu Gln
    435                 440                 445

Glu Val Thr Ser Leu Ala Met Glu Glu Ser Gln Glu Ala Lys Ser Leu
450                 455                 460

His Gln Pro Leu Gly Ile Cys Thr Asp Arg Thr Ser Asp Pro Asn Val
465                 470                 475                 480

Leu His Ser Gly Glu Glu Gly Thr Pro Gln Tyr Leu Lys Gly Gln Leu
            485                 490                 495

Pro Leu Leu Ser Ser Val Gln Ile Glu Gly His Pro Met Ser Leu Pro
        500                 505                 510

Leu Gln Pro Pro Ser Arg Pro Cys Ser Pro Ser Asp Gln Gly Pro Ser
    515                 520                 525

Pro Trp Gly Leu Leu Glu Ser Leu Val Cys Pro Lys Asp Glu Ala Lys
530                 535                 540

Ser Pro Ala Pro Glu Thr Ser Asp Leu Glu Gln Pro Thr Glu Leu Asp
545                 550                 555                 560

Ser Leu Phe Arg Gly Leu Ala Leu Thr Val Gln Trp Glu Ser
            565                 570

<210> SEQ ID NO 72
<211> LENGTH: 1725
<212> TYPE: DNA
<213> ORGANISM: homo sapiens

<400> SEQUENCE: 72
atgaggacgc tgctgaccat cttgactgtg ggatccctgg ctgctcacgc ccctgaggac    60
ccctcggatc tgctccagca cgtgaaattc cagtccagca actttgaaaa catcctgacg   120
tgggacagcg ggccggaggg caccccagac acggtctaca gcatcgagta taagacgtac   180
```

-continued

```
ggagagaggg actgggtggc aaagaagggc tgtcagcgga tcacccggaa gtcctgcaac    240
ctgacggtgg agacgggcaa cctcacggag ctctactatg ccagggtcac cgctgtcagt    300
gcgggaggcc ggtcagccac caagatgact gacaggttca gctctctgca gcacactacc    360
ctcaagccac ctgatgtgac ctgtatctcc aaagtgagat cgattcagat gattgttcat    420
cctaccccca cgcccatccg tgcaggcgat ggccaccggc taaccctgga agacatcttc    480
catgacctgt tctaccactt agagctccag gtcaaccgca cctaccaaat gccacttgga    540
gggaagcaga gagaatatga gttcttcggc ctgacccctg acacagagtt ccttggcacc    600
atcatgattt gcgttccac ctgggccaag agagtgcccc ctacatgtg ccgagtgaag    660 acactgccag accggacatg gacctactcc ttctccggag ccttcctgtt ctccatgggc    720
ttcctcgtcg cagtactctg ctacctgagc tacagatatg tcaccaagcc gcctgcacct    780
cccaactccc tgaacgtcca gcgagtcctg actttccagc cgctgcgctt catccaggag    840
cacgtcctga tccctgtctt tgacctcagc ggccccagca gtctggccca gcctgtccag    900
tactcccaga tcagggtgtc tggacccagg gagcctgcag gagctccaca gcggcatagc    960
ctgtccgaga tcacctactt agggcagcca gacatctcca tcctccagcc ctccaacgtg   1020
ccacctcccc agatcctctc cccactgtcc tatgccccaa cgctgccccc tgaggtcggg   1080 ccccccatcct atgcacctca ggtgaccccc gaagctcaat tcccattcta cgccccacag   1140
gccatctcta aggtccagcc ttcctcctat gcccctcaag ccactccgga cagctggcct   1200
ccctcctatg gggtatgcat ggaaggttct ggcaaagact cccccactgg gacactttct   1260
agtcctaaac accttaggcc taaaggtcag cttcagaaag agccaccagc tggaagctgc   1320
atgttaggtg gcctttctct gcaggaggtg acctccttgg ctatggagga atcccaagaa   1380
gcaaaatcat tgcaccagcc cctggggatt tgcagagaca gaacatctga cccaaatgtg   1440
ctacacagtg gggaggaagg gacaccacag tacctaaagg gccagctccc cctcctctcc   1500
tcagtccaga tcgagggcca ccccatgtcc ctcccttttgc aacctccttc ccgtccatgt   1560 tcccctcgg accaaggtcc aagtccctgg ggctgctgg agtcccttgt gtgtcccaag    1620
gatgaagcca agagcccagc ccctgagacc tcagacctgg agcagcccac agaactggat   1680
tctcttttca gaggcctggc cctgactgtg cagtgggagt cctga                   1725
```

<210> SEQ ID NO 73
<211> LENGTH: 309
<212> TYPE: DNA
<213> ORGANISM: llama glama

<400> SEQUENCE: 73

```
aattttatgc tgactcagcc ctccgcggtg tccgtgtctt tgggacagac ggccaagatc     60
acctgccaag ggggctatta tgctcactgg taccagcaga agccaggcca ggcccctgtg    120
ttggtcatct atggaaataa taataggccc tcagggatcc ctgagcgctt ctctggctcc    180
agttctggga acacagccac cctgaccatc agcggggccc aggctgagga cgaggccgag    240
tattactgtc agtcaggaag cagtagtgct aatgctgtgt tcggcggagg gacccatctg    300
accgtcctg                                                            309
```

<210> SEQ ID NO 74
<211> LENGTH: 369
<212> TYPE: DNA
<213> ORGANISM: llama glama

<400> SEQUENCE: 74

```
caggtgcagc tggtggagtc tgggggaggc ttggtgcagc ctggggattc tctgagactc    60
tcctgtgcag cctctggatt caccttcgga agctatttca tgagctgggt ccgccaggct   120
ccaggaaagg ggcccgagtg ggtctcaggt attcatatta gtggtggtat tacatactac   180
ttagactccg tgaagggccg attcaccatc tccagagaca cgccaagaa cacgctgtat    240
ctgcaaatga caacctgaa acctgaggac acggccgtgt attattgtgt aacacccccg    300
ggccccttta aggcccatta caatggcatg aagtactggg gcaaagggac cctggtcacc   360
gtctcctca                                                            369
```

<210> SEQ ID NO 75
<211> LENGTH: 330
<212> TYPE: DNA
<213> ORGANISM: llama glama

<400> SEQUENCE: 75

```
aattttatgc tgactcagcc tccctccgtg tctggaactc tgggaaagac ggtcaccatc    60
tcctgcactg gaaccagtcg tgacattggg gactataact atgtctcctg gtatcaacag   120
ctcccaggat tggcccccaa actcctgatc tataaagtca acactcgatc ctcagggacc   180
cctgatcgct ctctggctc caagtcaggc aacacggcct ccctgaccat ctctgggctc    240
cagtctgagg acgaggctga ttattactgt gcctcatata gactgtacgc cgattatgtg   300
ttcggcggag ggaccatct gaccgtcctg                                     330
```

<210> SEQ ID NO 76
<211> LENGTH: 360
<212> TYPE: DNA
<213> ORGANISM: llama glama

<400> SEQUENCE: 76

```
caggtgcagc tcgtggagtc tgggggaggc ttggtgcagc ctgggggttc tctgagactc    60
tcctgtgcag cctctggatt caccttcagt agctacgaca tgagctgggt ccgccaggct   120
ccagggaagg ggctggagtg ggtgtccagt atttataatg acggtagtaa cacagcctat   180
tcagactccg tgaagggccg attcaccatc tccagagaca cgccaagaa cacgttgtat    240
ctgcaaatga acagcttgaa atctgaggac acggccgtgt attactgtgc aaaagttggc   300
tttagtggta cttactacag tgaatcatgg ggccagggga cccaggtcac cgtgtcctca   360
```

<210> SEQ ID NO 77
<211> LENGTH: 309
<212> TYPE: DNA
<213> ORGANISM: llama glama

<400> SEQUENCE: 77

```
ctgcctgtgc tgactcagcc ctccgcggtg tccgtgtctt tgggacagac ggccaggatc    60
acctgccaag ggggctatta tgctcactgg taccagcaga agccaggcca ggcccctgtg   120
ctggtcatct atggacagaa taataggccc tcagggatcc ctgagcgctt ctctggctcc   180
ggcgctggga acacagccac cctgaccatc agcggggccc aggctgagga cgaggctgag   240
tattactgtc agtcaggaag cagtagtgct aatgctgtgt tcggcggagg gaccaagctg   300
accgtcctc                                                            309
```

<210> SEQ ID NO 78
<211> LENGTH: 360

<212> TYPE: DNA
<213> ORGANISM: Artificial Sequence
<220> FEATURE:
<223> OTHER INFORMATION: Germlined antibody sequence

<400> SEQUENCE: 78

```
caggtgcagc tcgtggagtc tgggggaggc ttggtgcagc ctgggggttc tctgagactc      60
tcctgtgctg cctctggatt caccttcagt agctacgaca tgaactgggt ccgccaggct     120
ccagggaagg ggctggagtg ggtgtccagc atttataacg acgccagtaa cacagcctat     180
tcagactccg tgaagggccg attcaccatc tccagagaca actcaaagaa cacgttgtat     240
ctgcaaatga acagcctgag agctgaggac acggccgtgt attactgtgc gaaagttggc     300
tttagtggta cttactacag tgaatcatgg ggccagggga ccctcgtcac tgtctcctca     360
```

<210> SEQ ID NO 79
<211> LENGTH: 309
<212> TYPE: DNA
<213> ORGANISM: Artificial Sequence
<220> FEATURE:
<223> OTHER INFORMATION: Germlined antibody sequence

<400> SEQUENCE: 79

```
tcctacgaac tgactcagcc ctcctcggtg tccgtggcgt tgggacagac ggccaggatc      60
acctgccaag gaggctatta tgcacactgg taccagcaga agccaggcca ggcccctgtg     120
ctggtcatct atggacagaa taataggccc tcaggatcc ctgagcgctt ctctggctcc      180
ggcgctggga acacagccac cctgacaatc agccgcgccc aggctgagga cgaggctgac     240
tattactgtc agtcaggaag cagtagttct aatgctgtgt tcggcggagg gaccaagctg     300
accgtcctc                                                             309
```

<210> SEQ ID NO 80
<211> LENGTH: 369
<212> TYPE: DNA
<213> ORGANISM: Artificial Sequence
<220> FEATURE:
<223> OTHER INFORMATION: Germlined antibody sequence

<400> SEQUENCE: 80

```
caggtgcagc tcgtggagtc tgggggcggc ttggtgcagc ctggggattc tctgagactc      60
tcctgtgcag cctctggatt caccttcagt agctatttca tgagctgggt ccgccaggct     120
ccaggaaagg ggcccgagtg ggtctcaggt attcatatta gtggtggtat tacatactac     180
acggactccg tgaagggccg attcaccatc tccagagaca acgcaaagaa cacgctgtat     240
ctgcaaatga acagcctgag agctgaggac acggccgtgt attattgtgt aacacccccg     300 ggcccctta aggcccatta caatggcgcg aagtactggg gcaaagggac cctggtcact     360
gtctcctca                                                             369
```

<210> SEQ ID NO 81
<211> LENGTH: 330
<212> TYPE: DNA
<213> ORGANISM: Artificial Sequence
<220> FEATURE:
<223> OTHER INFORMATION: Germlined antibody sequence

<400> SEQUENCE: 81

```
cagtctgccc tgactcagcc tcctccgtg tctggatctc ctggacagtc tgtcaccatc       60
tcctgcactg gaaccagtag tgacattggg tcctataact atgtctcctg gtatcaacag     120
```

```
ctcccaggaa aggccccaa actcctgatc tatgaggtca acaagcgatc ctcaggggtc    180
cctgatcgct tctctggctc caagtcaggc aacacggcct ccctgaccat ctctgggctc    240
caggctgagg acgaggctga ttattactgt gcctcatata gactgtacgc cgattatgtg    300
ttcggcggag ggacccaact gaccgtcctc                                     330
```

<210> SEQ ID NO 82
<211> LENGTH: 10
<212> TYPE: PRT
<213> ORGANISM: homo sapiens

<400> SEQUENCE: 82

Glu Pro Lys Ser Cys Asp Lys Thr His Thr
1               5                   10

<210> SEQ ID NO 83
<211> LENGTH: 5
<212> TYPE: PRT
<213> ORGANISM: homo sapiens

<400> SEQUENCE: 83

Cys Pro Pro Cys Pro
1               5

<210> SEQ ID NO 84
<211> LENGTH: 8
<212> TYPE: PRT
<213> ORGANISM: homo sapiens

<400> SEQUENCE: 84

Ala Pro Glu Leu Leu Gly Gly Pro
1               5

<210> SEQ ID NO 85
<211> LENGTH: 12
<212> TYPE: PRT
<213> ORGANISM: homo sapiens

<400> SEQUENCE: 85

Glu Leu Lys Thr Pro Leu Gly Asp Thr Thr His Thr
1               5                   10

<210> SEQ ID NO 86
<211> LENGTH: 50
<212> TYPE: PRT
<213> ORGANISM: homo sapiens

<400> SEQUENCE: 86

Cys Pro Arg Cys Pro Glu Pro Lys Ser Cys Asp Thr Pro Pro Cys
1               5                   10                  15

Pro Arg Cys Pro Glu Pro Lys Ser Cys Asp Thr Pro Pro Cys Pro
                20                  25                  30

Arg Cys Pro Glu Pro Lys Ser Cys Asp Thr Pro Pro Cys Pro Arg
                35                  40                  45

Cys Pro
    50

<210> SEQ ID NO 87
<211> LENGTH: 8
<212> TYPE: PRT
<213> ORGANISM: homo sapiens

<400> SEQUENCE: 87

```
Ala Pro Glu Leu Leu Gly Gly Pro
1               5

<210> SEQ ID NO 88
<211> LENGTH: 7
<212> TYPE: PRT
<213> ORGANISM: homo sapiens

<400> SEQUENCE: 88

Glu Ser Lys Tyr Gly Pro Pro
1               5

<210> SEQ ID NO 89
<211> LENGTH: 5
<212> TYPE: PRT
<213> ORGANISM: homo sapiens

<400> SEQUENCE: 89

Cys Pro Ser Cys Pro
1               5

<210> SEQ ID NO 90
<211> LENGTH: 8
<212> TYPE: PRT
<213> ORGANISM: homo sapiens

<400> SEQUENCE: 90

Ala Pro Glu Phe Leu Gly Gly Pro
1               5

<210> SEQ ID NO 91
<211> LENGTH: 3
<212> TYPE: PRT
<213> ORGANISM: homo sapiens

<400> SEQUENCE: 91

Glu Arg Lys
1

<210> SEQ ID NO 92
<211> LENGTH: 10
<212> TYPE: PRT
<213> ORGANISM: homo sapiens

<400> SEQUENCE: 92

Cys Cys Val Glu Cys Pro Pro Cys Pro
1               5                   10

<210> SEQ ID NO 93
<211> LENGTH: 7
<212> TYPE: PRT
<213> ORGANISM: homo sapiens

<400> SEQUENCE: 93

Ala Pro Pro Val Ala Gly Pro
1               5

<210> SEQ ID NO 94
<211> LENGTH: 78
<212> TYPE: PRT
<213> ORGANISM: Artificial Sequence
<220> FEATURE:
<223> OTHER INFORMATION: EST sequence

<400> SEQUENCE: 94
```

```
Val Arg Ser Ile Gln Met Ile Val His Pro Thr Pro Thr Pro Ile Arg
1               5                   10                  15

Ala Gly Asp Gly His Arg Leu Thr Leu Glu Asp Ile Phe His Asp Leu
                20                  25                  30

Phe Tyr His Leu Glu Leu Gln Val Asn Arg Thr Tyr Gln Met His Leu
                35                  40                  45

Gly Gly Lys Gln Arg Glu Tyr Glu Phe Phe Gly Leu Thr Pro Asp Thr
            50                  55                  60

Glu Phe Leu Gly Thr Ile Met Ile Cys Val Pro Thr Trp Ala
65                  70                  75
```

<210> SEQ ID NO 95
<211> LENGTH: 78
<212> TYPE: PRT
<213> ORGANISM: macaca mulatta

<400> SEQUENCE: 95

```
Val Arg Ser Ile Gln Met Ile Val His Pro Thr Pro Thr Pro Ile Arg
1               5                   10                  15

Ala Gly Asp Gly His Arg Leu Thr Leu Glu Asp Ile Phe His Asp Leu
                20                  25                  30

Phe Tyr His Leu Glu Leu Gln Val Asn Arg Thr Tyr Gln Met His Leu
                35                  40                  45

Gly Gly Glu Gln Arg Glu Tyr Glu Phe Phe Gly Leu Thr Pro Asp Thr
            50                  55                  60

Glu Phe Leu Gly Thr Ile Met Ile Cys Val Pro Thr Trp Ser
65                  70                  75
```

<210> SEQ ID NO 96
<211> LENGTH: 79
<212> TYPE: PRT
<213> ORGANISM: macaca fascicularis

<400> SEQUENCE: 96

```
Val Arg Ser Ile Gln Met Ile Val His Pro Thr Pro Thr Pro Ile Arg
1               5                   10                  15

Ala Gly Asp Gly His Arg Leu Thr Leu Glu Asp Ile Tyr Asp Leu Ser
                20                  25                  30

Tyr His Leu Glu Leu Gln Val Asn Arg Thr Tyr Gln Met Val Asn His
                35                  40                  45

Leu Gly Gly Lys Gln Arg Glu Tyr Glu Phe Phe Gly Leu Thr Pro Asp
            50                  55                  60

Thr Glu Phe Leu Gly Thr Ile Met Ile Cys Val Pro Thr Trp Ser
65                  70                  75
```

<210> SEQ ID NO 97
<211> LENGTH: 79
<212> TYPE: PRT
<213> ORGANISM: macaca fascicularis

<400> SEQUENCE: 97

```
Val Arg Ser Ile Gln Met Ile Val His Pro Thr Pro Thr Pro Ile Arg
1               5                   10                  15

Ala Gly Asp Gly His Arg Leu Thr Leu Glu Asp Ile Tyr Asp Leu Ser
                20                  25                  30

Tyr His Leu Glu Leu Gln Val Asn Arg Thr Tyr Gln Met Val Asn His
                35                  40                  45
```

Leu Gly Gly Lys Gln Arg Glu Tyr Glu Phe Phe Gly Leu Thr Pro Asp
        50                  55                  60

Thr Glu Phe Leu Gly Thr Ile Met Ile Cys Val Pro Thr Trp Ser
65                  70                  75

<210> SEQ ID NO 98
<211> LENGTH: 77
<212> TYPE: PRT
<213> ORGANISM: macaca fascicularis

<400> SEQUENCE: 98

Val Arg Ser Ile Gln Met Ile Val His Pro Thr Pro Thr Pro Ile Arg
1               5                   10                  15

Ala Gly Asp Gly His Arg Leu Thr Leu Glu Asp Ile Tyr Asp Leu Ser
            20                  25                  30

Tyr His Leu Glu Leu Gln Val Asn Arg Thr Tyr Gln Met His Leu Gly
        35                  40                  45

Gly Lys Gln Arg Glu Tyr Glu Phe Phe Gly Leu Thr Pro Asp Thr Glu
    50                  55                  60

Phe Leu Gly Thr Ile Met Ile Cys Val Pro Thr Trp Ser
65                  70                  75

<210> SEQ ID NO 99
<211> LENGTH: 293
<212> TYPE: PRT
<213> ORGANISM: homo sapiens

<400> SEQUENCE: 99

Leu Arg Leu Glu Tyr Leu Ile Arg Leu Thr Ile Gly Tyr Arg Leu Asn
1               5                   10                  15

Gly Thr Ala Ala Thr Met Gly Trp Ser Cys Ile Ile Leu Phe Leu Val
            20                  25                  30

Ala Thr Ala Thr Gly Val His Ser Pro Glu Asp Pro Ser Asp Leu Leu
        35                  40                  45

Gln His Val Lys Phe Gln Ser Ser Asn Phe Glu Asn Ile Leu Thr Trp
    50                  55                  60

Asp Ser Gly Pro Glu Gly Thr Pro Asp Thr Val Tyr Ser Ile Glu Tyr
65                  70                  75                  80

Lys Thr Tyr Gly Glu Arg Asp Trp Val Ala Lys Lys Gly Cys Gln Arg
            85                  90                  95

Ile Thr Arg Lys Ser Cys Asn Leu Thr Val Glu Thr Gly Asn Leu Thr
        100                 105                 110

Glu Leu Tyr Tyr Ala Arg Val Thr Ala Val Ser Ala Gly Gly Arg Ser
    115                 120                 125

Ala Thr Lys Met Thr Asp Arg Phe Ser Ser Leu Gln His Thr Thr Leu
130                 135                 140

Lys Pro Pro Asp Val Thr Cys Ile Ser Lys Val Arg Ser Ile Gln Met
145                 150                 155                 160

Ile Val His Pro Thr Pro Thr Pro Ile Arg Ala Gly Asp Gly His Arg
            165                 170                 175

Leu Thr Leu Glu Asp Ile Phe His Asp Leu Phe Tyr His Leu Glu Leu
        180                 185                 190

Gln Val Asn Arg Thr Tyr Gln Met His Leu Gly Gly Lys Gln Arg Glu
    195                 200                 205

Tyr Glu Phe Phe Gly Leu Thr Pro Asp Thr Glu Phe Leu Gly Thr Ile
210                 215                 220

```
Met Ile Cys Val Pro Thr Trp Ala Lys Glu Ser Ala Pro Tyr Met Cys
225                 230                 235                 240

Arg Val Lys Thr Leu Pro Asp Arg Thr Trp Thr Ile Glu Gly Arg Asp
                245                 250                 255

Met Asp Pro Lys Ser Cys Asp Lys Thr His Thr Cys Pro Pro Cys Pro
            260                 265                 270

Ala Pro Glu Leu Leu Gly Arg Pro Ser Val Phe Leu Phe Pro Pro Lys
        275                 280                 285

Pro Lys Asp Thr Leu
    290

<210> SEQ ID NO 100
<211> LENGTH: 293
<212> TYPE: PRT
<213> ORGANISM: macaca mulatta

<400> SEQUENCE: 100

Leu Arg Leu Glu Tyr Leu Ile Arg Leu Thr Ile Gly Tyr Arg Leu Asn
1               5                   10                  15

Gly Thr Ala Ala Thr Met Gly Trp Ser Cys Ile Ile Leu Phe Leu Val
            20                  25                  30

Ala Thr Ala Thr Gly Val His Ser Pro Glu Asp Pro Ser Asp Leu Leu
        35                  40                  45

Gln His Val Lys Phe Gln Ser Asn Asn Phe Glu Asn Ile Leu Thr Trp
    50                  55                  60

Asp Ser Gly Pro Glu Gly Thr Pro Asp Thr Val Tyr Ser Ile Glu Tyr
65                  70                  75                  80

Lys Thr Tyr Gly Glu Arg Asp Trp Val Ala Lys Lys Gly Cys Gln Arg
                85                  90                  95

Ile Thr Arg Lys Ser Cys Asn Leu Thr Val Glu Thr Gly Asn His Thr
            100                 105                 110

Glu Leu Tyr Tyr Ala Arg Val Thr Ala Val Ser Ala Gly Gly Arg Ser
        115                 120                 125

Ala Thr Lys Met Thr Asp Arg Phe Asn Ser Leu Gln His Thr Ala Leu
    130                 135                 140

Lys Pro Pro Asp Val Thr Cys Ile Pro Lys Val Arg Ser Ile Gln Met
145                 150                 155                 160

Ile Val His Pro Thr Pro Thr Pro Ile Arg Ala Gly Asp Gly His Arg
                165                 170                 175

Leu Thr Leu Glu Asp Ile Phe His Asp Leu Phe Tyr His Leu Glu Leu
            180                 185                 190

Gln Val Asn Arg Thr Tyr Gln Met His Leu Gly Gly Glu Gln Arg Glu
        195                 200                 205

Tyr Glu Phe Phe Gly Leu Thr Pro Asp Thr Glu Phe Leu Gly Thr Ile
    210                 215                 220

Met Ile Cys Val Pro Thr Trp Ser Lys Lys Ser Ala Pro Tyr Met Cys
225                 230                 235                 240

Arg Val Arg Thr Leu Pro Asp Arg Thr Trp Thr Ile Glu Gly Arg Asp
                245                 250                 255

Met Asp Pro Lys Ser Cys Asp Lys Thr His Thr Cys Pro Pro Cys Pro
            260                 265                 270

Ala Pro Glu Leu Leu Gly Gly Pro Ser Val Phe Leu Phe Pro Pro Lys
        275                 280                 285

Pro Lys Asp Thr Leu
    290
```

<210> SEQ ID NO 101
<211> LENGTH: 292
<212> TYPE: PRT
<213> ORGANISM: macaca fascicularis

<400> SEQUENCE: 101

Leu Arg Leu Glu Tyr Leu Ile Arg Leu Thr Ile Gly Tyr Arg Leu Asn
1               5                   10                  15

Gly Thr Ala Ala Thr Met Gly Trp Ser Cys Ile Ile Leu Phe Leu Val
            20                  25                  30

Ala Thr Ala Thr Gly Val His Ser Pro Glu Asp Pro Ser Asp Leu Leu
            35                  40                  45

Gln His Val Lys Phe Gln Ser Asn Asn Phe Glu Asn Ile Leu Thr Trp
        50                  55                  60

Asp Ser Gly Pro Glu Gly Thr Pro Asp Thr Val Tyr Ser Ile Glu Tyr
65                  70                  75                  80

Lys Thr Tyr Gly Glu Arg Asp Trp Val Ala Lys Lys Gly Cys Gln Arg
                85                  90                  95

Ile Thr Arg Lys Ser Cys Asn Leu Thr Val Glu Thr Gly Asn His Thr
            100                 105                 110

Glu Leu Tyr Tyr Ala Arg Val Thr Ala Val Ser Ala Gly Gly Arg Ser
        115                 120                 125

Ala Thr Lys Met Thr Asp Arg Phe Asn Ser Leu Gln His Thr Ala Leu
        130                 135                 140

Lys Pro Pro Asp Val Thr Cys Ile Pro Lys Val Arg Ser Ile Gln Met
145                 150                 155                 160

Ile Val His Pro Thr Pro Thr Pro Ile Arg Ala Gly Asp Gly His Arg
                165                 170                 175

Leu Thr Leu Glu Asp Ile Tyr Asp Leu Ser Tyr His Leu Glu Leu Gln
            180                 185                 190

Val Asn Arg Thr Tyr Gln Met His Leu Gly Gly Lys Gln Arg Glu Tyr
        195                 200                 205

Glu Phe Phe Gly Leu Thr Pro Asp Thr Glu Phe Leu Gly Thr Ile Met
    210                 215                 220

Ile Cys Val Pro Thr Trp Ser Lys Lys Ser Ala Pro Tyr Met Cys Arg
225                 230                 235                 240

Val Arg Thr Leu Pro Asp Arg Thr Trp Thr Ile Glu Gly Arg Asp Met
                245                 250                 255

Asp Pro Lys Ser Cys Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu
290